United States Patent [19]

Biddlecom et al.

[11] 4,171,331
[45] Oct. 16, 1979

[54] 1 AND 2-SUBSTITUTED ANALOGUES OF CERTAIN PROSTAGLANDINS

[75] Inventors: William G. Biddlecom; Harold C. Kluender; Warren D. Woessner, all of Madison, Wis.

[73] Assignee: Miles Laboratories, Inc., Elkhart, Ind.

[21] Appl. No.: 912,515

[22] Filed: Jun. 5, 1978

[51] Int. Cl.$^2$ .......................... A01N 9/36; C07F 9/40
[52] U.S. Cl. .................. 260/946; 260/563 R; 260/567.6 M; 260/586 R; 260/607 AL; 260/609 E; 260/609 D; 260/953; 260/609 F; 260/607 R; 542/429; 424/214; 424/217; 424/248.57; 424/320; 424/325; 421/329; 421/331; 421/337; 421/343; 544/173
[58] Field of Search .......................... 260/946, 953

[56] References Cited

U.S. PATENT DOCUMENTS

| 3,632,627 | 1/1972 | Gordon et al. ............... 260/953 X |
| 4,105,792 | 8/1978 | Skuballa et al. ............. 260/953 X |

OTHER PUBLICATIONS

Claim 1 of U.S. 4,081,478, Mar. 28, 1978 OG.
Claim 1 of U.S. 4,085,139, Apr. 18, 1978 OG.

Primary Examiner—Anton H. Sutto
Attorney, Agent, or Firm—Jerome L. Jeffers

[57] ABSTRACT

Disclosed are trans 1 & 2-di(loweralkyl)phosphono; 1 & 2-chloro, bromo and iodo; 1 & 2-thio and 1 & 2-amino analogues of $E_1$, $A_1$, $F_{1\alpha}$, $F_{1\beta}$, 11 deoxy $E_1$, 11 deoxy $F_{1\beta}$, and 11 deoxy $F_{1\alpha}$ prostaglandins.

The prostaglandins of this invention are variously useful as antithrombic agents, bronchodilators such as in the treatment of asthma, inhibitors of gastric secretion and as antihypertensive agents. Certain of the prostaglandins disclosed herein are useful as precursors for prostaglandins having one or more of the foregoing utilities.

8 Claims, No Drawings

1 AND 2-SUBSTITUTED ANALOGUES OF CERTAIN PROSTAGLANDINS

BACKGROUND OF THE INVENTION

1. Field of the Invention

The compounds of this invention are analogues of natural prostaglandins.

Natural prostaglandins are alicyclic compounds related to prostanoic acid, the structure of which is:

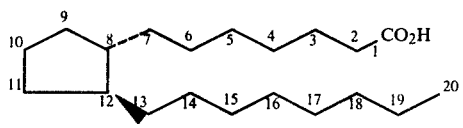

By convention, the carbon atoms of prostanoic acid are numbered sequentially from the carboxylic carbon atom. An important stereochemical feature of the compound is the trans-orientation of the sidechains $C_1$–$C_7$ and $C_{13}$–$C_{20}$, an orientation common to all natural prostaglandins. In prostanoic acid, as elsewhere in this specification, solid lines (—) provide a reference plane (such as the cyclopentyl ring or the bonds among atoms $C_1$–$C_7$ and $C_{13}$–$C_{20}$); a dashed line (---) indicates projection of a covalent bond below such reference plane (alpha-configuration); while a wedged line (◀) represents direction above such plane (beta-configuration). In some structures, however, a swung dash or serpentine line (~) denotes orientation of a covalent bond either above or below a plane of reference (indicated by the Greek letter xi in the nomenclature of such structures).

Natural prostaglandins have the general structure,

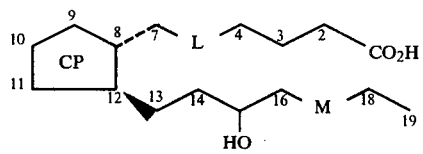

in which: L and M may be ethylene or cis-vinylene radicals; and the cyclopentyl ring

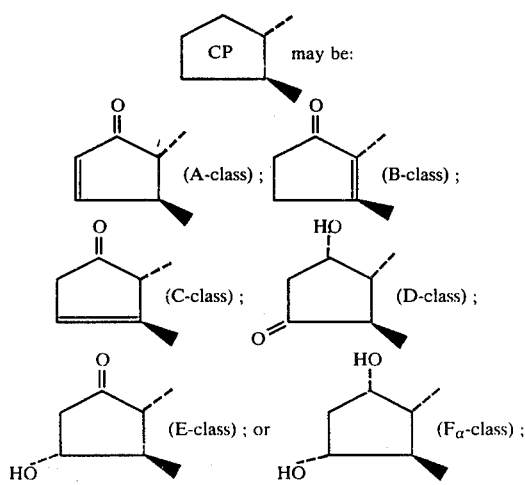

The above formula for natural prostaglandins and all representations of the cyclopentyl moiety depict the natisomer, i.e., the $C_7$–$C_8$ bond in the alpha-configuration and the $C_{12}$–$C_{13}$ bond in the beta-configuration. In the entisomer (which does not occur in nature), the direction of the bonds at $C_7$–$C_8$ and $C_{12}$–$C_{13}$ is reversed.

Prostaglandins are classified according to the functional groups present in the five-membered ring and the presence of double bonds in the ring or chains. Prostaglandins of the A-class (PGA or prostaglandin A) are characterized by an oxo group at $C_9$ and a double bond at $C_{10}$–$C_{11}$ ($\Delta^{10,11}$); those of the B-class (PGB) have an oxo group at $C_9$ and a double bond at $C_8$–$C_{12}$ ($\Delta^{8,12}$); compounds of the C-class (PGC) contain an oxo group at $C_9$ and a double bond at $C_{11}$–$C_{12}$ ($\Delta^{11,12}$); members of the D-class (PGD) have an oxo group at $C_{11}$ and an alpha-oriented hydroxy group at $C_9$; prostaglandins of the E-class (PGE) have an oxo group at $C_9$ and an alpha-oriented hydroxyl group at $C_{11}$; and members of the $F_\alpha$-class (PGF$_\alpha$) have an alpha-directed hydroxyl group at $C_9$ and an alpha-oriented hydroxyl group at $C_{11}$. Within each of the A, B, C, D, E, and F classes of prostaglandins are three subclassifications based upon the presence of double bonds in the side-chains at $C_5$–$C_6$, $C_{13}$–$C_{14}$, or $C_{17}$–$C_{18}$. The presence of a trans-unsaturated bond only at $C_{13}$–$C_{14}$ is indicated by the subscript numeral 1; thus, for example, PGE$_1$ (or prostaglandin E$_1$) denotes a prostaglandin of the E-type (oxo-group at $C_9$ and an alpha-hydroxyl at $C_{11}$) with a trans-double bond at $C_{13}$–$C_{14}$. The presence of both a trans-double bond at $C_{13}$–$C_{14}$ and a cis-double bond at $C_5$–$C_6$ is denoted by the subscript numeral 2; for example, PGE$_2$. Lastly, a trans-double bond at $C_{13}$–$C_{14}$, a cis-double bond at $C_5$–$C_6$ and a cis-double bond at $C_{17}$–$C_{18}$ is indicated by the subscript numeral 3; for example, PGE$_3$. The above notations apply to prostaglandins of the A, B, C, D, and F series as well; however, in the last, the alpha-orientation of the hydroxyl group at $C_9$ is indicated by the subscript Greek letter $\alpha$ after the numerical subscript. When the hydroxyl group at $C_9$ is in the beta-orientation, the $F_1$ series prostaglandin is referred to as $F_{1\beta}$.

Nomenclature of prostaglandins and their analogues deserves note insofar as there are three current systems followed in the scientific and patent literature. One system for convenience referred to as the Nelson system, uses the trivial names of prostaglandins and designates analogues by modifications of the trivial names (see J. Med. Chem., 17; 911 [1974]). Another system follows the rules of the International Union of Pure and Applied Chemistry (IUPAC) and refers to prostaglandins and their analogues as derivatives of heptanoic acid. A third system employs a convention of Chemical Abstracts ("CA") that designates prostaglandins and derivatives thereof as derivatives of prostanoic acid. An example of each system is provided below for the following structure:

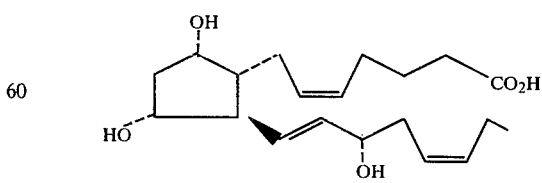

In the Nelson system, the foregoing compound is designated prostaglandin F$_{3\alpha}$ or PGF$_{3\alpha}$ (shortened form); in the IUPAC system, 7-[3R,5S-dihydroxy-2R-(3S-hydroxy-1E,5Z-octadienyl)-cyclopent-1R-yl]-5Z-deptenoic acid; in the CA system (5Z,9α,11α,1-3E,15S,17Z)-9,11,15-trihydroxyprosta-5,13,17-trien-1-oic acid.

It is important to note that in all natural prostaglandins there is a hydroxyl group at $C_{15}$ oriented below the plane in which $C_{15}$ is located. In the Cahn-Ingold-Prelog system of defining stereochemistry, that $C_{15}$ hydroxyl group is in the S-configuration. Inversion of the orientation of the $C_{15}$ hydroxyl group such that the group projects above the plane in which the $C_{15}$ atom is located represents the R-configuration. The Cahn-Ingold-Prelog system is used to define stereochemistry of any asymmetric center outside of the carbocyclic ring in all three systems of nomenclature described above. In some literature, however, $\alpha,\beta$ designations are used for such centers.

Isomerism of a double bond is designated in all three systems by use of conventional prefixes cis- or trans-, or their respective equivalents, Z or E (as suggested in J. Am. Chem. Soc., 59: 509 [1968]).

For details of other conventions utilized in nomenclature of prostaglandins, see: Nelson, N. A., "Prostaglandin Nomenclature", J. Med. Chem., 17: 911 (1974).

Recent research indicates that prostaglandins appear ubiquitously in animal tissues and elicit biochemical and physiological effects in a variety of mammalian systems.

In the endocrine system, for example, experimental evidence indicates prostaglandins influence the hormone synthesis or release of hormones in the secretory glands. In rats, $PGE_1$ and $PGE_2$ increase the release of the growth hormone while $PGA_1$ increases its synthesis. In sheep, $PGE_1$ and $PGE_{1\alpha}$ inhibit ovarian progesterone secretion. In a variety of mammals, $PGF_{1\alpha}$ and $PGF_{2\alpha}$ act as luteolytic factors. In mice, $PGE_1$, $PGE_2$, $PGF_{1\alpha}$ and $PGF_{1\beta}$ increase thyroid activity. In hypophysectomized rats, $PGE_1$, $PGE_2$ and $PGF_{1\alpha}$ stimulate stereoidogenesis in the adrenal glands.

In the mammalian male reproductive system, $PGE_1$ contracts the smooth muscle of the vas deferens. In the female reproductive system, PGE and $PGF_\alpha$ compounds contract uterine smooth muscle. In general, PGE, PGB and PGA compounds relax in vitro human uterine muscle strips, while those of the $PGF_\alpha$ class contract such isolated preparations. PGE compounds, in general, promote fertility in the female reproductive system while $PGF_{2\alpha}$ has contragestational effects. $PGF_{2\alpha}$ also appears to be involved in the mechanism of menstruation. In general, $PGE_2$ produces potent oxytocic effects in inducing labor, while $PGF_{2\alpha}$ induces spontaneous abortions in early pregnancy.

$PGF_\alpha$ and PGE compounds have been isolated from a variety of nervous tissues. $PGE_1$ retards whereas $PGF_{2\alpha}$ facilitates transmission along motor pathways in the central nervous system. $PGE_1$ and $PGE_2$ reportedly inhibit transmitter release from adrenergic nerve endings in the guinea pig.

Prostaglandins stimulate contraction of gastrointestinal smooth muscle in vivo and in vitro. In dogs, $PGA_1$, $PGE_1$, and $PGE_2$ inhibit gastric secretion. $PGA_1$ exhibits similar activity in man. Natural prostaglandins and some of their analogues also protect gastric mucosa from ulceration induced by nonsteroidal antiinflammatory agents.

In most mammalian respiratory tracts, PGE and PGF compounds affect in vitro preparations of tracheal smooth muscle. Specifically, $PGE_1$ and $PGE_2$ relax while $PGF_{2\alpha}$ contracts such smooth muscle. The human lung normally contains PGE and PGF compounds; consequently, some cases of bronchial asthma may involve an imbalance in the production or metabolism of those compounds.

Prostaglandins are involved in certain hematic mechanisms in mammals. $PGE_1$, for example, inhibits aggregation of blood platelets in vitro.

In a variety of mammalian cardiovascular systems, compounds of the PGE and PGA classes are vasodilators whereas those of the $PGF_\alpha$ class are vasoconstrictors, by virtue of their action on vascular smooth muscle.

Prostaglandins naturally appear in the kidney and reverse experimental and clinical renoprival hypertension.

The prostaglandins and their analogues have broad clinical implications. In obstetrics and gynecology, they may find use in fertility control, treatment of menstrual disorders, the induction of labor, and the correction of hormone disorders. In gastroenterology, they may help treat or prevent peptic ulcers and various disorders involving motility, secretion, and absorption in the gastrointestinal tract. They may, in the respiratory area, prove beneficial in the therapy of bronchial asthma and other diseases involving bronchoconstriction. In hematology, they may display utility as anti-clotting agents in diseases such as venous thrombosis, thrombotic coronary occlusion and other diseases involving thrombi. For circulatory diseases, they have therapeutic utility in hypertension, peripheral vasopathies and cardiac disorders.

The following references include a more complete review of the chemical, physiological and pharmacological aspects of the prostaglandins: The Prostaglandins, Vol. I., P. Ramwell, Ed., New York, Plenum Press, 1973; Ann. N.Y. Acad. Sci., 180: 1-568 (1971); Higgins and Braunwald, J. Am. Med. Assn., 53: 92-112 (1972); Osterling, Marozowich, and Roseman, J. Phar. Sci., 61: 1861–1895 (1972); and Nakano, Resident and Staff Phys., 19: 92, 94–99, and 102-106 (1973).

PRIOR ART

Prostaglandin analogues incorporating a dialkylphosphono moiety rather than an ester or an acid moiety in the 1-position have not been reported in either the scientific or the patent literature.

Prostaglandin analogues incorporating the halomethyl moiety rather than an ester or acid moiety in the 1-position have not been reported in either the scientific or the patent literature. Prostaglandin analogues containing polar groups (i.e., halomethyl) in place of the carboxylic acid or ester exhibit biological activity and are hypothesized to be less subject to deactivation by $\beta$-oxidation than the natural prostaglandins and would therefore exhibit longer lasting activity. They can also be used as intermediates in the synthesis of other prostaglandin analogues, e.g., dialkylphosphono, thio and amino derivatives, which can be formed by the displacement of bromine by nucleophiles. Although no prostaglandin analogues have been reported containing halogen at $C_1$, a number of patents and publications have reported halogen-containing prostaglandins. For example: American Cyanamide Company, Australia Patent Application 51081-73;

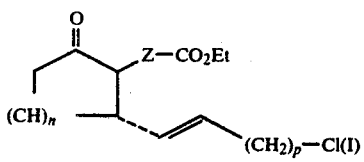

where n=1, 2; Z—(CH$_2$)$_m$—(m=1 to 8);

etc. C. Gandolf et al. reported in Farm. Ed. Sci., 27, 1125 (1972);

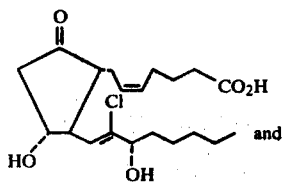

American Cyanamide Co., BE 802678 discloses;

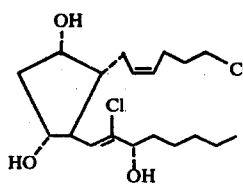

Upjohn, Chem. Abst. 80, 265 (1974); 3674p. reports;

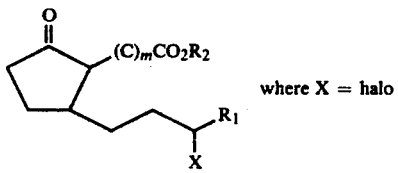

Syntex: FR 2162212, discloses:

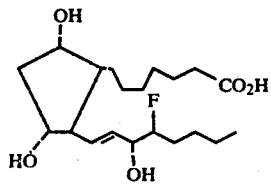

where

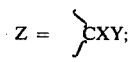

X and Y are H, F or Cl.

Although there are many patents and papers describing prostaglandins incorporating sulfur at various positions, there are relatively few references to analogues incorporating a sulfur atom into the upper sidechain (C$_1$→C$_7$) and no references to 2-alkylthiomethyl analogues. For example: J. Fried, et al. report in J. Amer. Chem. Soc., 96, 6759 (1974);

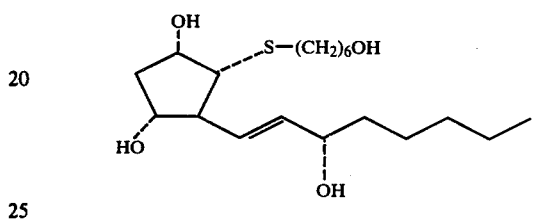

Erba Patent, NL 730522 discloses;

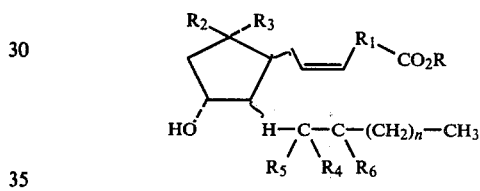

where: R$_1$=—S—CH$_2$-; R$_2$=H, R$_3$=OH (or vice-versa); A=—C=C— or other, R$_6$=H, 1 to 4 C-alkyl and n=3, 4, etc.

The following composition is disclosed in FR 2145601;

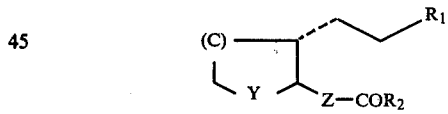

where Z=(C)$_q$SCH$_2$ American Cyanamid discloses a composition of the formula:

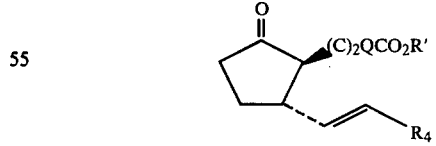

where Q=SCH$_2$ in Chem. Abstracts, 80(11) 327 (1974) (59568 m).

Prostaglandin analogues containing an amine or amine derivative at C-1 have not been reported in the scientific or patent literature. A number of patents, e.g. U.S. Pat. No. 3,927,197, include acid derivatives at C-1 such as amides (I), carboxylate-amine salts (II) and the 2-decarboxy-2-(2,3,4,5-tetrayol-1-yl) derivative (III).

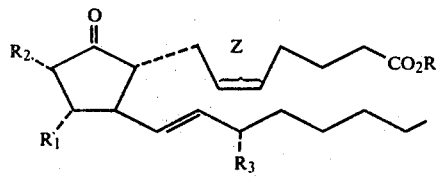

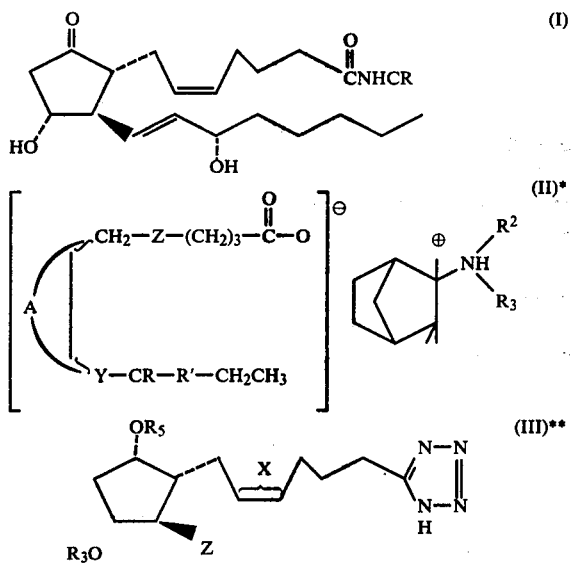

(I)

(II)*

(III)**

*See Aries, Derwent 34719W/21; FR 2240-212; Aires R 06.08.73- FR-028936
**See:
(a) Pfizer, Inc., Derwent 64494V/37, *BE-811-556, Pfizer, Inc. 26.02.73- U.S. 335586;
(b) Pfizer, Inc., Derwent 64494V/37, *BE-811-556, Pfizer, Inc. 26.02.73- U.S. 335586;
(c) Sandoz AG, Derwent 60288V/34, *DT 2405-255, Sandoz AG 16.11.73-CH-016182 (08.02.73-CH-001805);
(d) AKZO NV, Derwent 27925W/17, *DT 2448-392, AKZO NV 12.10.73-NL-014038

SUMMARY OF THE INVENTION

The present invention provides novel, trans, 1&2 di(loweralkyl)phosphono; 1&2-chloro, bromo and iodo; 1&2-thio and 1&2-amino analogues of $E_1$, $A_1$, $F_{1\alpha}$, $F_{1\beta}$, 11 deoxy $E_1$, 11 deoxy $F_{1\beta}$ and 11 deoxy $F_{1\alpha}$ prostaglandins. These compounds are represented by the following general formula:

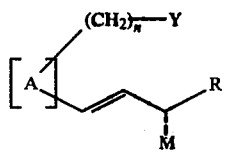

wherein n is 6 or 7; M is H or OH; a is

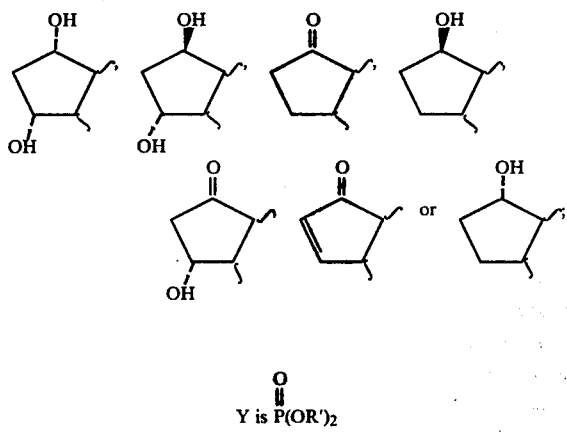

O
‖
Y is P(OR')$_2$ where R' is methyl, ethyl, propyl or butyl; chloro, bromo or iodo;

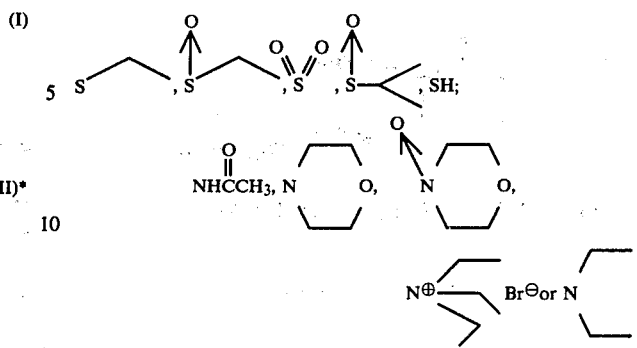

and R is $(CH_2)_3CH_3$, $(CH_2)_4CH_3$, $CH_3$, cyclohexyl, $$C\text{-}(CH_3)_2,$$

$(CH_2)_2CH_3$ or $(CH_2)CH_3$.

DETAILED DESCRIPTION OF THE INVENTION

The compounds of the present invention, various 1- or 2-heteroatom prostaglandin analogues, are prepared as shown in the General Scheme, infra. As shown on this scheme, various starting materials, either commercially available or prepared according to published procedures, are converted via any of several alternate routes to the various 1- or 2-heteroatom prostaglandins.

In one case such starting materials are converted to various 2-(ω-haloalkyl)cyclopent-2-en-1-ones. These reactions are shown in detail in Scheme I, infra. These intermediates are in turn, either converted to 2-(ω-heteroatomalkyl)cyclopent-2-en-1-ones as detailed in Scheme II, infra, or to 1- or 2-haloprostaglandins (1- or 2-halo PG's) as detailed in Scheme III, infra. Then the 2-(ω-heteroatomalkyl)cyclopent-2-en-1-ones are converted to 1- or 2-heteroatom PG's according to Scheme III, or alternately the 1- or 2-halo PG's are converted to the 1- or 2-heteroatom PG's according to Scheme V, infra. Scheme VI, infra, then shows various ways that the 1- or 2-heteroatom PG's may be altered to produce various manipulated 1- or 2-heteroatom PG's.

As a variation to the above routes, the 1- or 2-halo PG's can be prepared directly from known ester PG's according to Scheme IV, infra. Various known ester PG's are used in this invention, or they can be prepared from known 2-(ω-carboalkoxyalkyl)cyclopent-2-en-1-ones as shown in Scheme IV.

The literature references for the various starting materials and the descriptions of the detailed Schemes I-VI are shown below.

According to Scheme I the appropriate lactone 1 wherein (n=5 or 6) is reduced with a reducing agent such as diisobutylaluminum hydride, in an inert solvent such as toluene, under an inert atmosphere such as argon and at an appropriate temperature (−78° for diisobutylaluminum hydride) to yield lactol 2. Starting material 1 wherein n=5 (6-hexanolactone) is available from Aldrich Chemical Company. Lactol 2 is then reacted with N-(cyclopenten-1-yl)morpholine 3(Aldrich) according to the procedure of M. P. L. Caton, et al., Tetrahedron Letters, 773 (1972) by replacing 7-hydroxylheptanal with lactol 2 (n=5) to yield 4 (n=5). Intermediate 4 (n=6) was prepared by the method of M. P. L. Caton, et al.

Intermediate 4 was converted to 6 by treatment with methanesulfonylchloride and pyridine and then 6 was converted to 5 (X=Br) by reaction with potassium bromide in a suitable solvent such as acetone. Intermediate 5 (X=Cl) could be prepared directly from 4 by treatment with $CCl_4$/triphenylphosphine. Intermediate 5 (X=I) could be prepared from 3 by reaction with 7-iodoheptanal 9 in a suitable solvent such as benzene followed by pyrolysis of the resultant intermediate after removal of side products with mineral acid followed by bicarbonate washes.

Intermediate 9 was obtained from 8-iodo-1-octene 8 by treatment of 8 with ozone in a suitable solvent such as methanol at $-78°$ C. and then dimethylsulfide at $-20°$ C. to ambient temperature. 8-Iodo-1-octene 8 was prepared according to the procedure of C. J. Sih, et al., Tetrahedron Letters, 2435 (1972) from commercial 1,7-octadiene.

According to Scheme II - Route A, the intermediate 5 from Scheme I is reacted with a trialkyl phosphite such as trimethylphosphite (available commercially from Aldrich, triethyl-tri-n-propyl, tri-iso-propyl and tri-n-butylphosphite are all also commercially available and can be used in this reaction) at a temperature of from ambient to reflux of the excess phosphite reagent. The excess reagent is removed by evaporation in vacuo and the product 12 is purified by chromatography on silica gel using appropriate solvents such as hexane/ethyl acetate gradients.

Alternately according to Scheme II - Route B, the intermediate 7 from Scheme I is reacted with a secondary amine 13 such as morpholine in an inert solvent such as dimethylformamide at a temperature of between ambient and 100° C. to yield intermediate 14. Compound 14 can in turn be isomerized in the presence of a strong acid such as concentrated hydrochloric acid to yield 2-($\omega$-dialkylaminoalkyl)cyclopent-2-en-1-one, 15.

Either 14 or 15 may be oxidized by treatment with metachloroperbenzoic acid to the N-oxides 17 or 16 respectively. Compound 16 is converted to 17 by treatment with a strong acid as described above for the conversion of 14 to 15.

According to Scheme III the reaction of the appropriate substituted cyclopent-2-en-1-one (either 5, 12, 15 or 17 from Schemes I or II) with the organolithiocuprate of formula 19 in an inert solvent, under an inert atmosphere at a temperature of from $-80°$ to $+10°$ C. for about 0.25 to 3 hours, followed by chemical hydrolysis by treatment with a weakly-acidic water mixture, e.g., acetic acid-water (65:35 v/v) with 10% tetrahydrofuran, at a temperature of about 20° to 45° C. for about 0.5 to 48 hours provides the 1- or 2-halo or heteroatom prostaglandins 20 and 21.

The organolithiocuprates 19 are generally prepared from substituted 1E-iodoalkenes 18. The preparation of various 19 and 18 and their use in the synthesis of prostaglandins is described by C. J. Sih, et al., J. Amer. Chem. Soc., 97: 857 and 865 (1975); E. J. Corey, et al., J. Amer. Chem. Soc., 94: 7210 (1972); and H. C. Arndt, et al., Prostaglandins, 7: 387 (1974).

According to Scheme IV, a number of 1- or 2-halo or 1- or 2-methanesulfonyloxy prostaglandins can be prepared from well-known ester prostaglandins 23 or ester intermediates 22. The Sih, Corey and Arndt references listed above describe many such ester prostaglandin analogues. Following these references, esters 23 are easily prepared from earlier described iodo intermediate 18 and substituted cyclopent-2-en-1-one, 22.

The cyclopentanone function of 23 is reduced with a hydride reducing agent such as sodium borohydride in ethanol and then the resultant hydroxyl group is reacted with dihydropyran in an inert solvent such as ether in the presence of an acid catalyst such as p-toluenesulfonic acid to yield 24. Alternately any number of known PGE ester prostaglandin analogues 25 (See J. S. Bindra and R. Bindra, "Prostaglandin Synthesis," Academic Press, Inc., New York (1977) and references cited therein) can be likewise reduced with sodium borohydride to yield 26 and then reacted with dihydropyran to prepare blocked PGF ester analogue 24. The use of sodium borohydride to reduce a prostaglandin such as 23 or 25 is described by J. E. Pike, et al., J. Org. Chem., 34: 3552 (1969) and the use of dihydropyran is described by P. E. Eaton, et al., J. Org. Chem., 37: 1947 (1972).

Treatment of ester 24 with a reducing agent such as sodium bis(2-methoxyethoxy)aluminum hydride or lithium aluminum hydride or the like in a suitable inert solvent such as ether at a temperature of from 0° to solvent reflux yields alcohol 27.

The primary unblocked alcohol function of 27 is then reacted with methanesulfonylchloride and a suitable base such as triethylamine or pyridine or the like in a suitable inert solvent such as ether or tetrahydrofuran or the like at a temperature of from $-20°$ to solvent reflux to yield methanesulfonate 28.

Treatment of 28 with either lithium bromide or potassium iodide or the like in a suitable polar solvent such as acetone yields blocked 1- or 2-bromo or iodo-prostaglandin F analogue 29. Alternately 29 may be obtained directly from 27 by treatment with a carbontetrachloride/triphenylphosphine mixture as earlier described in the conversion of 4 to 5.

In a different approach, the copper reagent formed from 18 is reacted with substituted cyclopentenone 22 as earlier described, but the reaction mixture is treated with either acetic anhydride or acetyl chloride before an aqueous quench is used. Following this altered process, the product obtained is enolacetate 30 rather than ketone 23.

Reaction of 30 with sodium bis(2-methanoxyethoxy)aluminum hydride in a suitable solvent such as ether or tetrahydrofuran at from $-80°$ to 0° C. yields partially blocked prostaglandin E alcohol 31. Compound 31 is then treated with methanesulfonyl chloride and triethylamine in an inert solvent such as ether or tetrahydrofuran to yield blocked prostaglandin E methanesulfonate 32. Intermediate 32 is then reacted with sodium borohydride in alcohol to yield partially blocked prostaglandin F methanesulfonate 33. The free hydroxyl group of intermediate 33 is then reacted with a blocking agent such as ethyl vinyl ether in the presence of an acid catalyst such as p-toluenesulfonic acid to yield completely blocked prostaglandin F methanesulfonate 34. The blocking agent used in the conversion of 33 to 34 must be removable under conditions in which the tetrahydropyranyl groups of 34 remain intact. This is found to be true of the use of ethyl vinyl ether as a blocking agent (see Scheme V - conversion of 40 to 41).

Scheme V shows the conversion of various 1- or 2-halo or 1- or 2-methanesulfonyloxy prostaglandin intermediates to the herein claimed 1- or 2-heteroatom substituted prostaglandin analogues.

Thus according to Scheme V, 1- or 2-dimethylphosphono prostaglandin F analogues 35 are prepared from either 28 or 29 by initial reaction with trimethylphosphite in the presence of a small amount of potassium carbonate at reflux followed by hydrolysis with a weakly acidic mixture, e.g., acetic acid-water (65:35 v/v) with 10% tetrahydrofuran, at a temperature of about 20° to 45° C. for about 1-48 hours.

When either 28 or 29 is first reacted with a lower alkylmercaptan such as ethylmercaptan in the presence of sodium hydride in a suitable solvent such as tetrahydrofuran, and then the intermediate product is hydrolyzed with a weakly acidic mixture as noted above, the product obtained is the 1- or 2-alkylmercapto prostaglandin F analogue 38.

When either 28 or 29 is first reacted with thiourea in a suitable solvent such as 95% ethanol at reflux, and then the first formed product is reacted with an aqueous base such as aqueous potassium hydroxide at ambient temperature, and then the second formed product is hydrolyzed with either a weakly acidic mixture as noted above or with a strong acid such as aqueous hydrochloric acid the final product obtained is 1- or 2-thiol prostaglandin F analogue 37.

When either 28 or 29 is first reacted with a di(loweralkyl)amine such as diethylamine in a suitable solvent such as dimethylformamide in the presence of potassium carbonate, and then the first formed product is hydrolyzed as noted above with either a strong or a weak acid, the final product obtained is 1- or 2-di(loweralkyl)amino prostaglandin F analogue 36.

11-Deoxy prostaglandin E analogues are prepared as shown from 20 or 21 (from Scheme III). Reaction of 20 or 21 with a tri(loweralkyl)amine such as triethylamine at from ambient temperature to 80° C., followed by hydrolysis (if blocked) with either strong or weak acid as described above yields 1- or 2-tri(loweralkylammonium)prostaglandin E analogue 39 wherein the counterion X is determined by the identity of X of intermediate 20 or 21 or by the identity of the acid used in the hydrolysis, if done; i.e. use of hydrochloric acid in a hydrolysis yields 39 wherein X is chloride and use of hydrobromic acid in either hydrolysis or purification yields 39 wherein X is bromide.

If either 20 or 21 is first reacted with a loweralkylmercaptan such as ethylmercaptan in the presence of sodium hydride in a suitable solvent such as tetrahydrofuran, and the first formed product is hydrolyzed, if necessary, then the isolated product is 1- or 2-loweralkylmercapto prostaglandin E analogue 40.

Prostaglandin E analogues may be prepared from prostaglandin F precursors such as 34 from Scheme IV. A Scheme V continuation shows, for example, the preparation of 1- or 2-acetamido prostaglandin E analogue 44 from 34. The preparation of 1- or 2-acetamido prostaglandin F analogue 42 is also shown. The procedure of T. Mukaiyama, et al., Tetrahedron Letters, 3411 (1970) describes the conversion of alkylmethanesulfonates to primary amines. This process was applied to prostaglandin methanesulfonate 34 to yield an intermediate prostaglandin amine which was in turn reacted with acetic anhydride at 0° C. to yield hydroxylblocked acetamido prostaglandin F analogue 40*. Treatment of intermediate 40* with a weakly acidic mixture consisting of 65:35:10 (v/v) acetic acid-water-tetrahydrofuran for a short time (0.5-4 hours at ambient temperature) resulted in a mixture of partially hydrolyzed products. This mixture is chromatographed on silica gel as usual to yield 41 as a major component with Z' a THP blocked hydroxyl or H. Hydrolysis of 40* for a long time (12 to 48 hours) under similar conditions yields 1- or 2-acetamido prostaglandin F analogue 42. Intermediate compound 41 can be oxidized with a reagent such as Collins reagent (J. C. Collins, et al., Tetrahedron Letters, 3363 [1968]) to yield blocked 1- or 2-acetamido prostaglandin E analogue 43. Finally 43 can be hydrolyzed with a weakly acidic mixture such as acetic acid-water-tetrahydrofuran as used above for the conversion of 41 to 42. The final product is 1- or 2-acetamido prostaglandin E analogue 44.

Scheme VI shows the manipulation of 1- or 2-heteroatom prostaglandin analogues.

Part A shows the conversion of an E analogue 45 to an A analogue 46 by treatment with dilute organic or mineral acid and heat. This process as described by J. E. Pike, et al., J. Org. Chem., 34: 3552 (1969), is well-known to those skilled in the prostaglandin art.

Likewise conversion of a prostaglandin E analogue 47 to a prostaglandin F analogue 48 by treatment with a reducing agent such as sodium borohydride is described by Pike, et al., and is well-known to those skilled in the art.

1- or 2-(loweralkylmercapto)prostaglandin analogues 38 or 40 may be reacted with an oxidizing agent such as sodium periodate in a suitable solvent such as aqueous methanol to yield sulfoxide analogues 49 and 51 respectively. Analogue 38 may be oxidized with m-chloroperbenzoic acid in a suitable solvent such as ether to yield alkylsulfonyl prostaglandin analogue 50.

1- or 2-(diloweralkylamino)prostaglandin analogues such as 20 can be reacted with m-chloroperbenzoic acid in a suitable solvent such as chloroform followed by dilute aqueous acid hydrolysis to yeild N-oxido-1- or 2-(diloweralkylamino)prostaglandin analogues such as 52.

All compounds of this invention can be isolated from reaction mixtures and purified by well-known organic chemistry procedures. For example, the compounds can be isolated by dilution of the reaction mixture with water, extraction with a water-immiscible solvent such as benzene, cyclohexane, ether, ethyl acetate, methylene chloride, toluene and the like; chromatography; distillation or a combination of these procedures. Purification of these compounds can be accomplished by methods which are well-known in the art for the purification of prostaglandins, lipids, fatty acids, and fatty esters. Such methods as reverse phase partition chromatography; counter-current distribution; adsorption chromatography on acid washed magnesium silicate, neutral or acid washed silica gel, alumina or silicic acid; preparative paper chromatography; preparative thin layer chromatography; high pressure liquid-liquid chromatography; gas-liquid chromatography; and combinations thereof can be used to purify the compounds produced by the processes of this invention.

In the following examples, NMR spectra were determined in $CDCl_3$ and infrared (IR) spectra in $CHCl_3$ unless otherwise noted. Analytical thin layer chromatography was performed on 0.2 mm Silica Gel 60 F254 plates and preparative thin-layer chromatography was performed using 2.0 mm Silica Gel F254 plates. "System II" is defined as the organic layer from a mixture of ethyl acetate, acetic acid, isooctane and water in a ratio of 11:2:5:10. Spots were visualized under uv light and/or by ceric sulfate spray reagent (See K. Schreiber, et al., J. Chromatography, 12: 63 [1962]). Column chromatographic separations were performed on 85:15 silicic acid-diatomaceous earth, such as Celite, or silica gel 60 using a benzene-ethyl acetate or hexane-ethyl acetate gradient elution unless otherwise specified.

Mass spectra were determined by WARF, Inc., Madison, Wisconsin or Morgan Schaffer, Inc., Montreal, Canada.
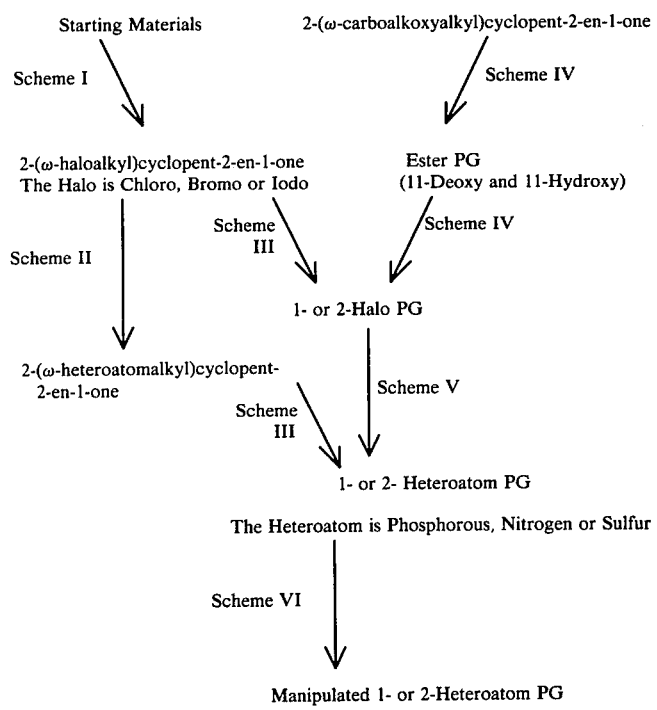
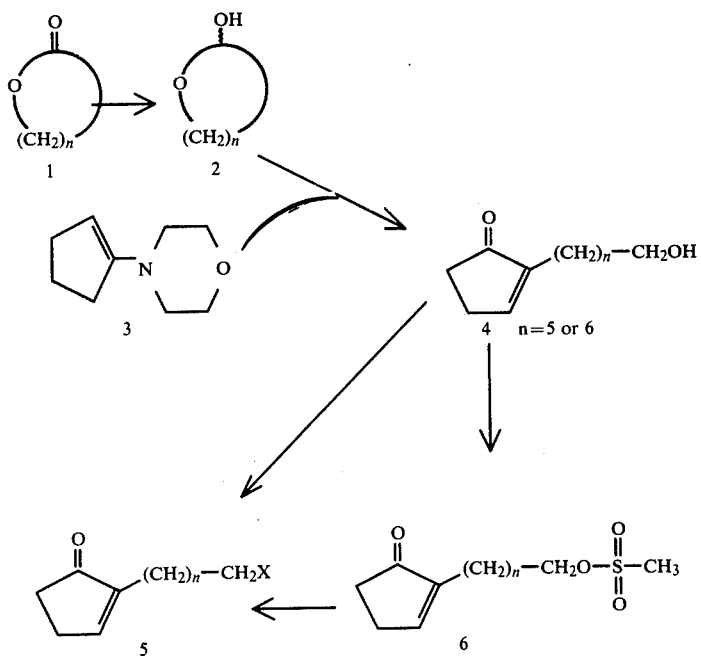
Scheme I
Synthesis of 2-(ω-Haloalkyl)cyclopent-2-en-1-ones

Scheme I
Synthesis of 2-(ω-Haloalkyl)cyclopent-2-en-1-ones
X=Cl, Br, I
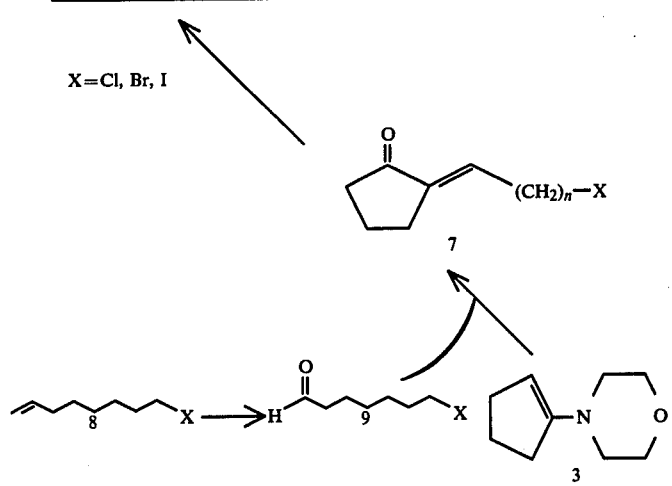
Scheme II
Synthesis of 2-(ω-Heteroatomalkyl)cyclopent-2-en-1-ones
Route A - Endo Precursor
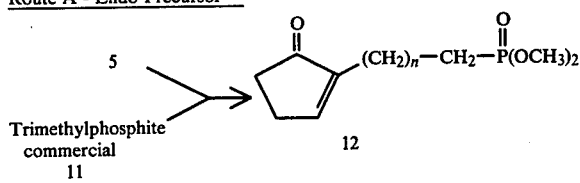
Route B - Exo Precursor
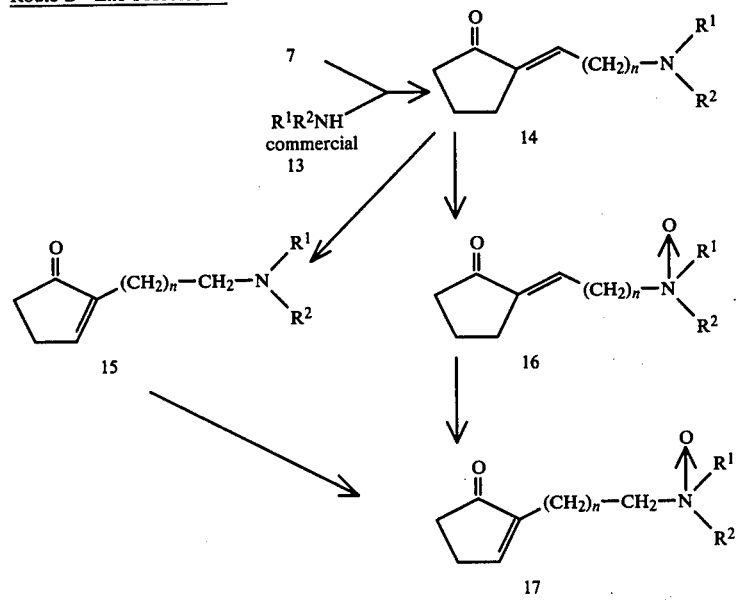
Scheme III
Reaction of 2-(ω-Halo- or ω-Heteroatomalkyl)cyclopent-2-en-1-ones
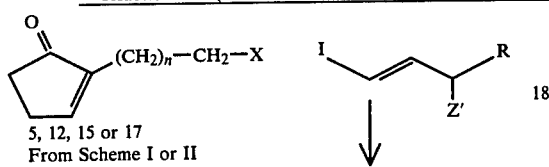
5, 12, 15 or 17
From Scheme I or II Scheme III
Reaction of 2-(ω-Halo- or ω-Heteroatomalkyl)cyclopent-2-en-1-ones
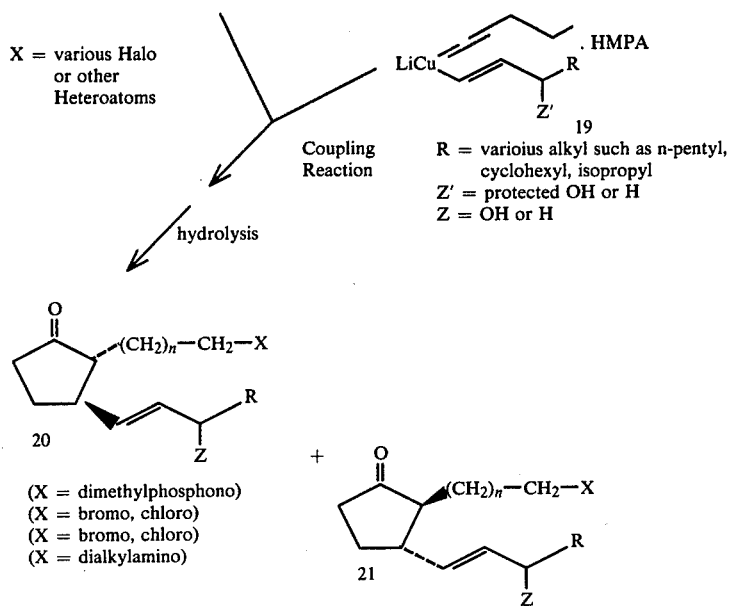
(X = dimethylphosphono)
(X = bromo, chloro)
(X = bromo, chloro)
(X = dialkylamino)

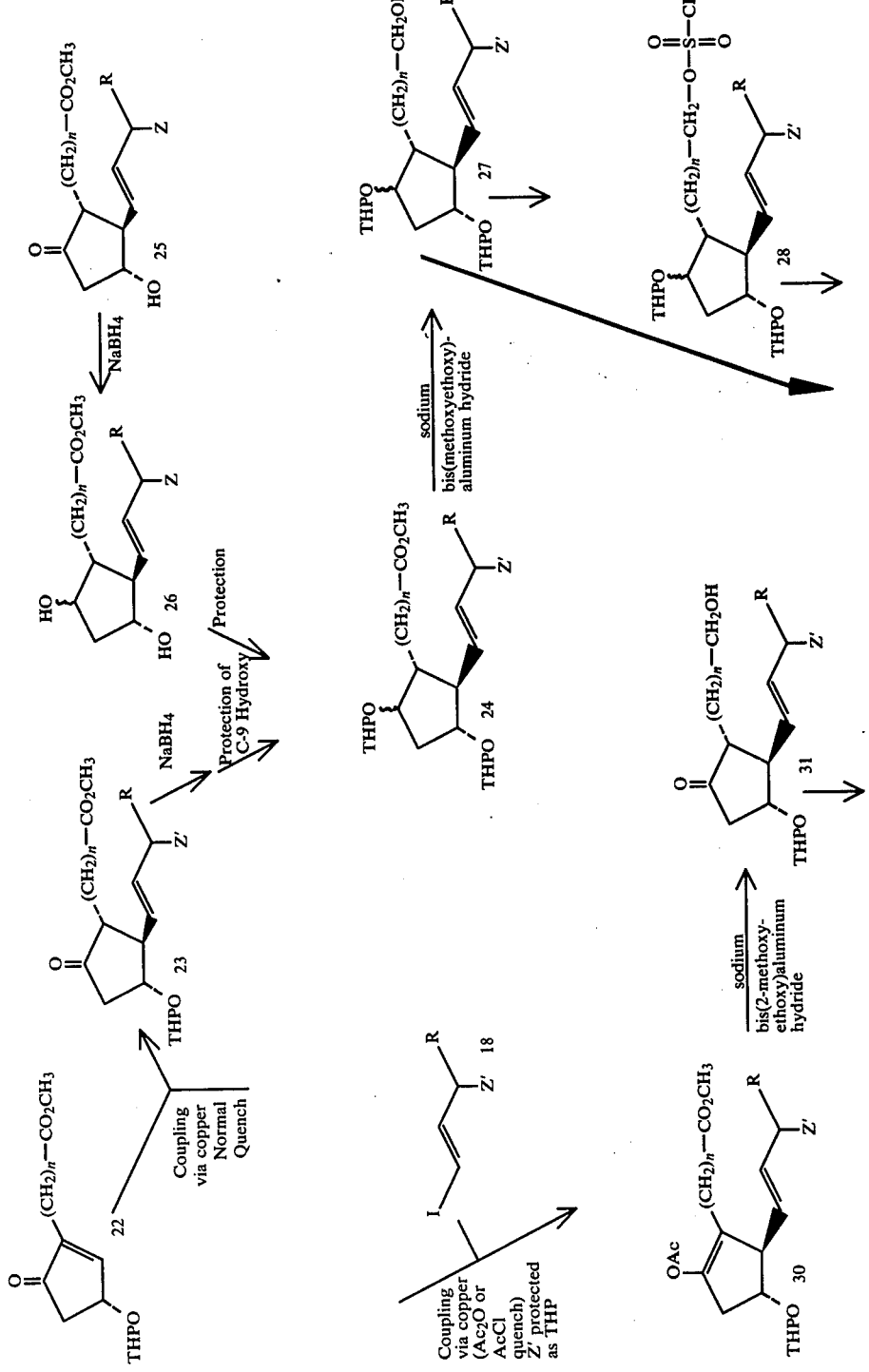

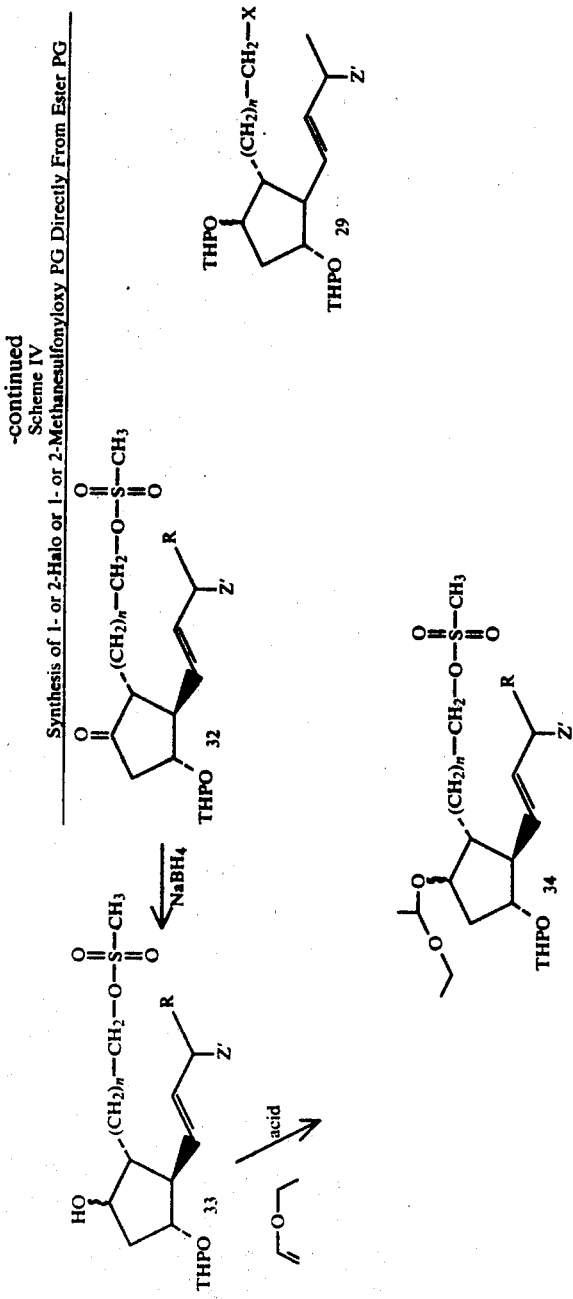

Scheme V
Reaction of 1-Halo or 1-Methanesulfonyloxy PG
F Analogs
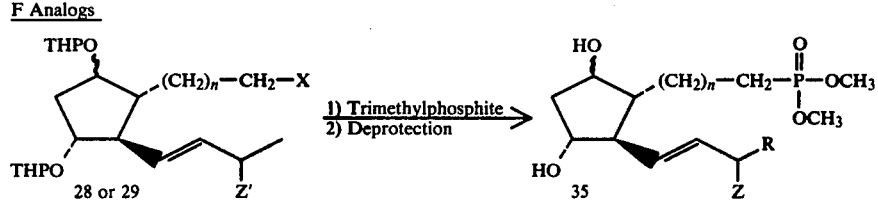
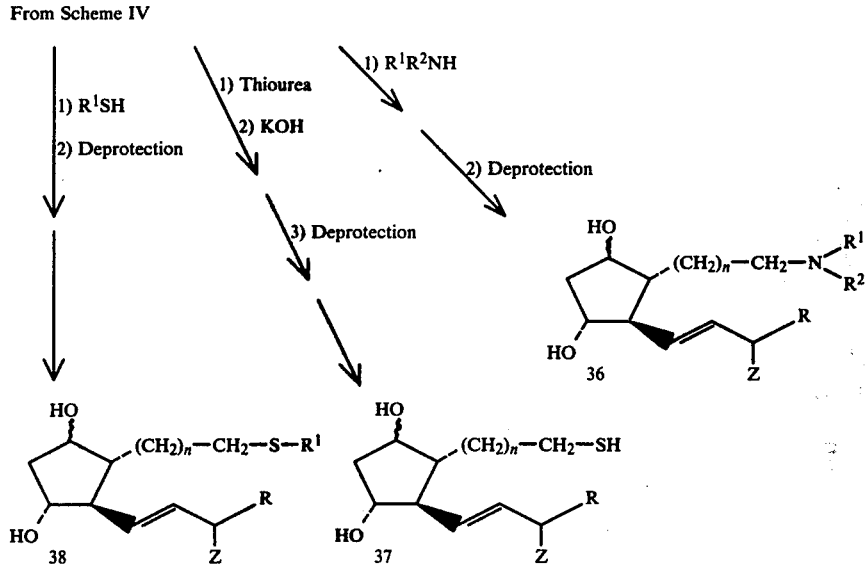
Scheme V
11-Deoxy E Analogs
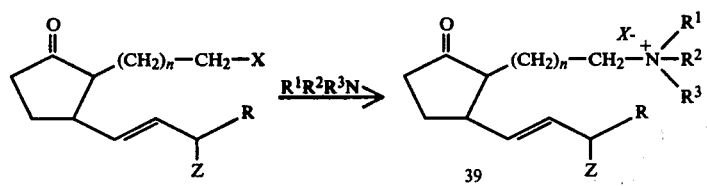
(X=halo, Z optionally protected)
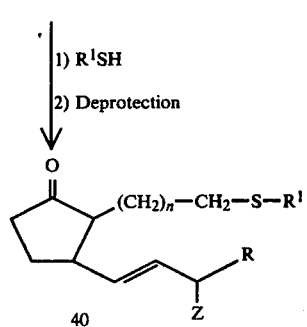
Scheme V
E Analogs from F Precursors -continued
Scheme V
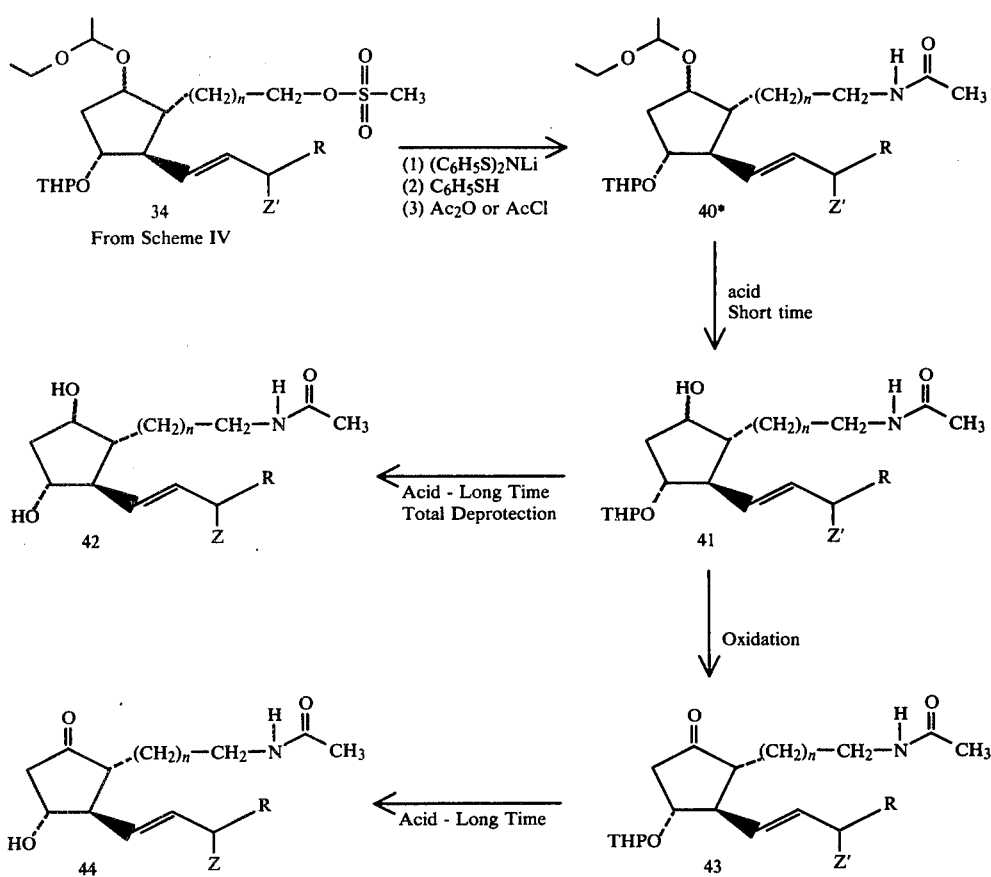
Scheme VI
Manipulation of 1- or 2-Heteroatom PG's
A - Conversion of E to A Analog
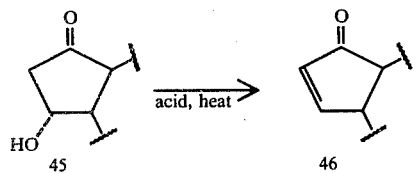
B - Conversion of E to F Analog
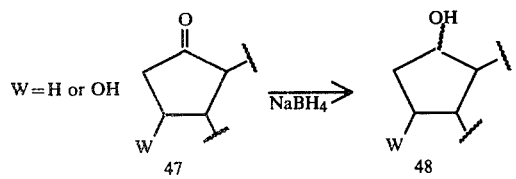
C - Oxidation of Heteroatoms
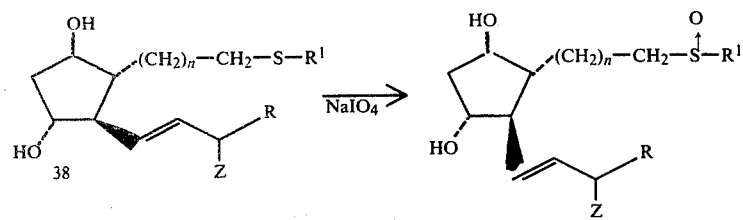

-continued
Scheme VI
Manipulation of 1- or 2-Heteroatom PG's

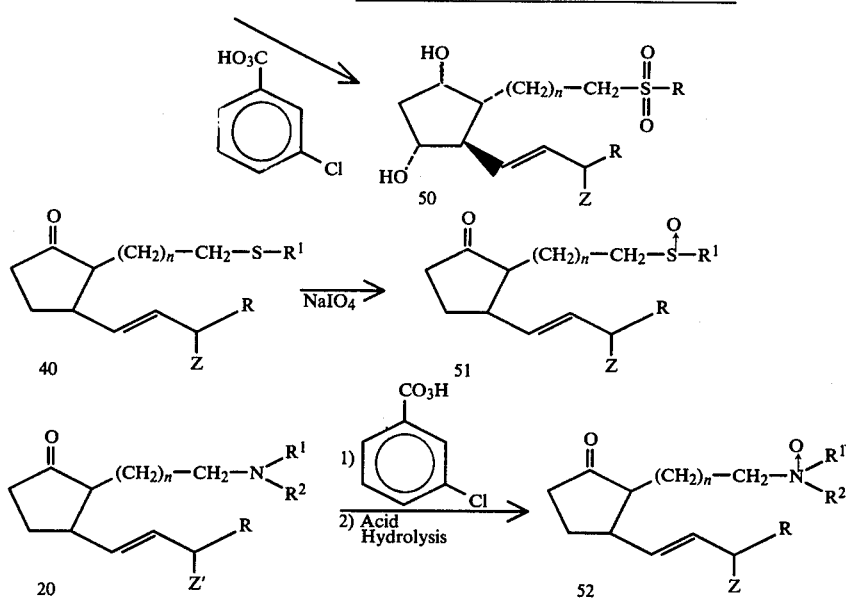

The method of practicing the present invention is more fully illustrated by the following examples in which all temperatures are in °C.

EXAMPLE I

Preparation of 2-(6-Hydroxyhex-1-yl)-2-cyclopentanone.

A one-liter, three-necked round-bottomed flask equipped with a mechanical stirring, argon inlet and addition funnel, was flame-dried while a stream of argon was passed through the apparatus. The flask was charged with 16.5 ml of 6-hexanolactone (0.145 mol) in 140 ml of dry toluene. The stirred solution was cooled to −78°. Diisobutylaluminum hydride (24.9 ml) was added dropwise over 1.75 hours. The reaction mixture was stirred for 3.25 hours at −78° whereupon 6.0 ml methanol in 19.0 ml of toluene was added over 15 minutes at −78°. The reaction mixture was warmed to 0° over 1.25 hours and 60 ml of 10% aqueous hydrochloric acid was added over 10 minutes. The reaction mixture was poured into a separatory funnel and the layers separated. The organic layer was dried ($Na_2SO_4$) and toluene removed in vacuo until the volume of organic material was about 150 ml. A solution of 25.9 gm N-(cyclopenten-1-yl)morpholine in 100 ml dry benzene was added and the reaction mixture was stirred for 16 hours under argon at 110°. The reaction mixture was cooled to 25° and 40 ml of 1:1 hydrochloric acid-water added. The reaction mixture was stirred at 25° for 1 hour, poured into a separatory funnel and the layers separated whereupon the aqueous layer was extracted with benzene. The combined organic layers were washed twice with saturated aqueous sodium bicarbonate. The benzene was removed in vacuo and 200 ml of n-butanol was added, followed by 2.5 ml of concentrated hydrochloric acid. The mixture was refluxed for 1 hour, cooled and poured into ether-water. The layers were separated and the aqueous layer extracted with ether. The combined organic layers were washed with saturated aqueous sodium bicarbonate and brine. They were dried ($MgSO_4$), filtered and evaporated in vacuo to afford 13.4 gm of a red oil. This oil was chromatographed on 85:15 silicic acid-Celite (benzene→ethyl acetate gradient elution) to afford 1.99 gm of the desired compound (I).

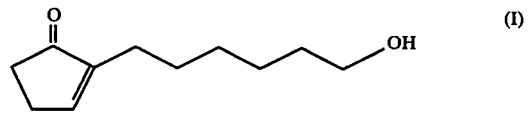

This compound is an orange oil, the structure of which was confirmed by nuclear magnetic resonance and infrared spectroscopy. The material exhibited the following spectral properties:

Analysis-NMR: δ3.63(broad t, $CH_2OH$), 7.32(m, 1, $=CH$-) IR($CHCl_3$) 2.78, 2.92(broad), 5.95, 6.07μ

EXAMPLE II

Preparation of 6-(5-Ketocyclopen-1-yl)hex-1-yl-methane sulfonate.

A solution of 273 mg of the composition prepared in Example I in 10 ml of tetrahydrofuran (THF) was cooled to 0° with stirring under argon. Triethylamine (151 mg, 0.208 ml) was injected, followed by 183 mg of distilled methanesulfonylchloride. The reaction mixture was stirred for 30 minutes at 0°, then poured into ice-water and extracted with ether. The ether extracts were washed three times with cold 5% aqueous hydrochloric acid and three times with cold 5% aqueous sodium carbonate. They were dried ($Na_2SO_4$), filtered and evaporated in vacuo to yield 334 mg of the desired compound (II).

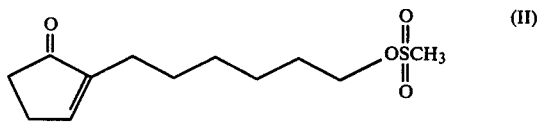

This compound is a light brown oil, the structure of which was confirmed by nuclear magnetic resonance.

Analysis-NMR(CDCl₃): δ2.98(s, 3, C$\underline{H}_3$), 4.2(t, J=6.0, Hz, 2, C$\underline{H}_2$O), 7.31(m, 1, =C$\underline{H}$-).

EXAMPLE III

Preparation of 2-(6-Bromohex-1-yl)-2-Cyclopentenone.

A solution of 332 mg (1.36 mmol) of the composition prepared as described in Example II in 2.5 ml dry acetone was stirred under argon with 600 mg lithium bromide for 17 hours at 25°. The acetone was removed in vacuo and water was added to the residue whereupon the mixture was extracted with ether:hexane (1:20). The organic extracts were washed with 10% aqueous sodium thiosulfate and brine, dried (MgSO₄), filtered and evaporated in vacuo to yield the desired compound (III).

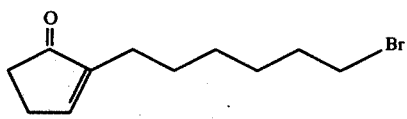
(III)

This compound is an orange oil the structure of which was confirmed by nuclear magnetic resonance and infrared spectroscopy.

Analysis-NMR(CDCl₃); δ3.40(t, J=7.0 Hz,2, CH₂Br), 7.32(m, 1, =C$\underline{H}$—) IR(CHCl₃): 5.92, 6.06μ.

EXAMPLE IV

Preparation of 2-(6-Dimethylphosphonohex-1-yl)-2-cyclopentenone.

A mixture of the composition prepared in Example III (100 mg, 0.409 mmol) and 0.95 ml (8.1 mmol) trimethylphosphite was added and the reaction mixture was refluxed an additional 21.5 hours under argon. The trimethylphosphite was removed in vacuo to afford 156 mg of the desired compound (IV).

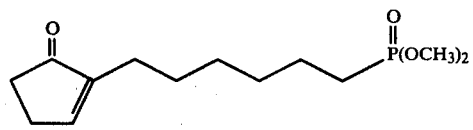
(IV)

This compound is a yellow oil the structure of which was confirmed by nuclear magnetic resonance.

Analysis-NMR(CDCl₃): δ3.80(d, J=11.0 Hz, 6, OC$\underline{H}_3$), 7.38(m, 1, =C$\underline{H}$—).

EXAMPLE V

Preparation of 2-(dimethylphosphono)-1-nor-15S-hydroxyprost13E-en-9-one.

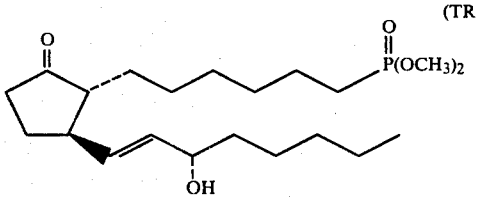
(TR 4177), and 2-(Dimethylphosphono)-1-nor-15S-hydroxy-8,12-iso-prost-13E-en-9-one.

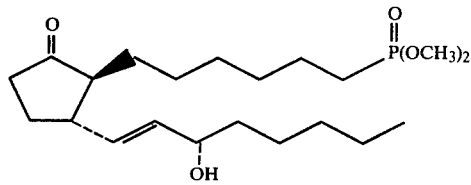
(TR 4178)

A solution of 175 mg of I-Iodo-3S-(1-ethoxyethoxy)-1-trans-octene (prepared and resolved according to the procedure of A. F. Kluge, K. G. Untch and J. H. Fried, J. Amer. Chem. Soc., 94: 7827 [1972]) in 3.5 ml of dry ether was cooled to −78° with stirring under argon. A solution of t-butyllithium in pentane (0.62 ml, 1.7 N) was injected and the reaction mixture was stirred for 2 hours at −78°, whereupon it was transferred into a stirred −78° solution of 62 mg of copper(I)pentyne in 1.6 ml ether (solubilized at 25° with 0.18 ml hexamethylphosphorous triamide). The reaction mixture was stirred 45 minutes at −78° and then a solution of 117 mg of the material prepared in example IV (0.428 mmol) in 1.2 ml THF was slowly injected. The reaction mixture was stirred for 35 minutes at −78°, then warmed to −10° via external application of an ice-salt bath. The temperature of the bath was allowed to rise to 0° over 1.5 hours. At this point, the reaction mixture was stirred for 45 minutes at 0° and 0.5 hour at 25° and then poured into 20% aqueous ammonium sulfate and extracted three times with ether. The ether extracts were washed with 2% V/V sulfuric acid-water, saturated aqueous sodium bicarbonate and brine. They were dried (MgSO₄), filtered and evaporated in vacuo to afford 148 mg of a yellow oil.

The yellow oil was stirred with 4.0 ml of 65:35 acetic acid-water and 0.4 ml THF for 16 hours at 25° under argon. The solvents were removed in vacuo to afford 102 mg of an orange oil. The oil was chromatographed on 85:15 silicic acid-Celite (benzene→ethyl acetate gradient elution) to afford 16.6 mg of the composition previously identified as TR 4177) and 19.4 mg of the composition previously identified as (TR 4178).

The structure of these compounds was confirmed by nuclear magnetic resonance, infrared and mass spectral analysis.

Analysis (TR 4177) NMR(CDCl₃): δ0.82(broad t, 3, pentyl-C$\underline{H}_3$) 3.70(d, J=11 Hz, 6, OC$\underline{H}_3$), 5.60(m, 2, trans-olefinic-H)

IR(CHCl₃): 2.78, 2.84(broad), 5.57, 10.08μ; [α]$_D$+21.5±0.3(c 1.73) Mass Spectrum: m/e 402(M⁺), 384(M⁺—H₂O).

TR 4178) NMR(CDCl₃): δ0.91(broad t, 3, pentyl-C$\underline{H}_3$), 3.78(d, J=1.0 Hz, 6, OC$\underline{H}_3$), 5.64(m, 2, trans-olefinic-$\underline{H}$)

IR(CHCl₃): 2.78, 2.84(broad), 5.57, 10.08μ [α]$_D$−15.8±0.5(c 1.13, CHCl₃)

Mass Spectrum: m/e 402(M⁺), 384(M⁺—H₂O).

EXAMPLE VI

Preparation of 2-(6-Methanesulfonyloxyheptyl)-7-cyclopentenone.

A solution of 1.15 gm of 2-(7-Hydroxyhept-1-yl)-2-cyclopentanone (V)

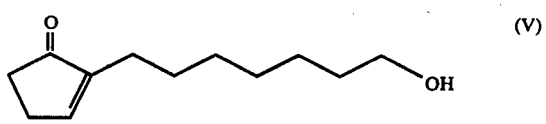

(V)

prepared as described by M. P. L. Caton, et al. in Tet. Let., 773 (1972) in 40 ml of dry THF was cooled to 0° with stirring under argon. Triethylamine (1.06 ml) was added, followed by 0.73 ml distilled methanesulfonyl chloride. The reaction mixture was stirred for 2.5 hours at 0° and then poured into ice-water and extracted with ether. The ether extracts were washed with cold 10% hydrochloric acid and cold 5% aqueous sodium carbonate. They were dried (MgSO₄), filtered and evaporated in vacuo to afford 1.35 gm of a yellow oil. This oil was dissolved in ether and 0.5 ml triethylamine was added, followed by approximately 5.0 ml of methanol. The mixture was shaken and the layers separated whereupon the ether layer was washed with 10% hydrochloric acid, 5% aqueous sodium carbonate and brine. It was dried (MgSO₄), filtered and evaporated in vacuo to afford 988 mg of a yellow oil of the desired composition (VI).

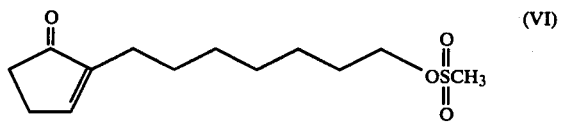

(VI)

The structure of this compound was confirmed by nuclear magnetic resonance.

Analysis—NMR(CDCl₃): δ3.00(s, 3H, C$\underline{H}$₃), 4.23(t, J=6.0 Hz, 2, C$\underline{H}$₂—S), 7.32(m, 1, =C$\underline{H}$—).

EXAMPLE VII

A solution of 988 mg of the material prepared in example (VI) in 7.6 ml of dry acetone was stirred at 25° under argon with 1.80 gm of lithium bromide for 18.25 hours. The acetone was removed in vacuo and the product was isolated as described for the preparation of compound (III) to afford 737 mg of the desired composition (VII) having the following structure:

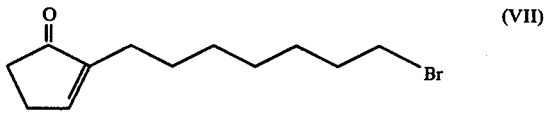

(VII)

The structure of this composition was confirmed by nuclear magnetic resonance and infrared spectroscopy.

Analysis-NMR(CDCl₃): δ3.40 (t, J=7.0 Hz, 2, C$\underline{H}$₂Br), 7.33 (m, 1, =C$\underline{H}$—)
IR(CHCl₃): 5.92, 6.06μ.

EXAMPLE VIII

Preparation of 2-(7-Dimethylphosphonohept-1-yl)-2-cyclopentenone.

A mixture of 300 mg of the composition prepared in Example VII and 2.85 ml of trimethylphosphite were refluxed for 3.5 hours under argon. Another 2.85 ml of trimethylphosphite was added and the reaction mixture was refluxed for an additional 15.5 hours under argon. The trimethylphosphite was removed in vacuo to afford 570 mg of a yellow oil having the following structure (VIII):

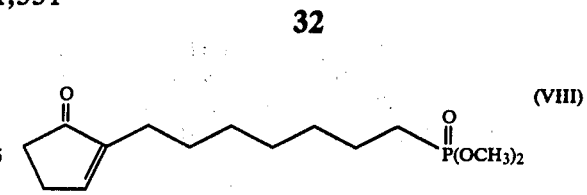

(VIII)

The structure of this composition was confirmed by nuclear magnetic resonance, infrared and mass spectral analysis.

Analysis-NMR(CDCl₃): δ3.73(d, J=11.0 Hz, 6, (CH₃), 7.33 (m, 1, =CH—)

IR(CHCl₃): 5.92, 6.06μ Mass spectrum: m/e 228(M+).

EXAMPLE IX

Preparation of 1-(dimethylphosphono)-15S-hydroxyprost-13E-en-9-one and 1-(Dimethylphosphono)-15S-hydroxy-8,12-iso-prost-13E-en-9-one.

A solution of 410 mg of 3S-(1-ethoxyethoxy)-1-Iodo-trans-1-octene in 8.0 ml dry ether was cooled to −78° with stirring under argon and 1.45 ml of 1.7 N t-butyllithium in pentane was injected. The reaction mixture was stirred for 2 hours at −78°, then transferred into a −78° stirred solution of 145 mg copper(I)pentyne in 3.7 ml dry ether (solubilized at 25° by addition of 0.4 ml hexamethylphosphorous triamide). The resultant complex was stirred 35 minutes at −78°, then a solution of 288 mg 2-(7-dimethylphosphonohept-1-yl)-2-cyclopenten-1-one in 3.0 ml THF was added dropwise over 10 minutes. The reaction mixture was stirred for 20 minutes at −78°, then warmed to −10° via external application of an ice-salt bath. The bath temperature was allowed to rise to 0° over 1.5 hours. The reaction mixture was stirred 0.5 hour at 0° and 0.5 hour at 25°, then poured into 20% aqueous ammonium sulfate and extracted with ether. The ether extracts were washed with 2% V/V sulfuric acid-water, saturated aqueous sodium bicarbonate and brine. They were dried (MgSO₄), filtered and ether evaporated in vacuo to afford 384 mg of a light yellow oil. The oil was stirred with 10 ml 65:35 acetic acid:water and 1.0 ml THF for 16.5 hours at 25° under argon and the solvents removed in vacuo to afford 267 mg of a yellow oil. The oil was chromatographed on 85:15 silicic acid:Celite (benzene→ethyl acetate gradient) to afford respectively 45.8 mg of a composition of the structure:

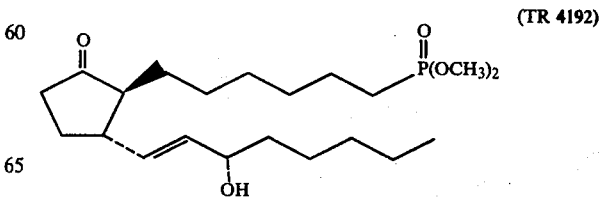

(TR 4192)

and 36.4 mg of a composition of the structure:

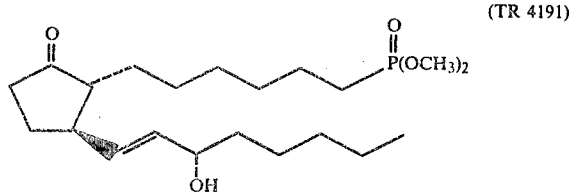
(TR 4191)

The structure of these compositions was confirmed by nuclear magnetic resonance and infrared analysis.

Analysis-(TR 4192) NMR(CDCl₃): δ0.90(broad t, 3, pentyl-C$\underline{H}_3$), 3.65(d, J=11.0 Hz, 6H, C$\underline{H}_3$), 4.06(m, 1H, C$\underline{H}$OH) 5.65(m, 2H, trans-olefinic-$\underline{H}$)

IR(CHCl₃) 2.78, 3.03(broad), 5.75, 10.08μ; $[\alpha]_D$+25.8°±0.5° (c 1.08, CHCl₃); $[\theta]_{296}$+6530°(c 1.35×10⁻⁷M, Methanol), (TR 4191) NMR(CDCl₃) and IR(CHCl₃) identical in essential aspects to spectra of TR 4192.

$[\alpha]_D$ −15.9±0.40 (c 0.98, CHCl₃); $[\theta]_{296}$ −6840° (c 1.20×10⁻⁷M, Methanol).

EXAMPLE X

Preparation of 1-Hydroxy-9β,11α,15S-tetrahydropyranyloxyprost-13E-ene.

Red-Al (70% solution of sodium bis(2-methoxyethoxy)-aluminum hydride, 1 gm, was added to a solution of 9,11,15-tristetrahydropyranyl-PGF₁β-methyl ester (448 mg) in 3 ml of dry tetrahydrofuran which was stirred at −10° under argon. The resultant mixture was stirred for 3 hours at −10° whereupon it was diluted with ether and then washed with 10% aqueous hydrochloric acid and saturated aqueous sodium bicarbonate. The resultant solution was dried (NaSO₄) and evaporated in vacuo to yield 333 mg of prostaglandin alcohol (X) as a clear oil. This material has the structural formula:

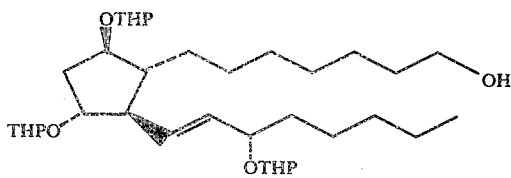
(X)

The structure of this compound was confirmed as follows: tlc (ether) R$_f$ 0.39; IR(film) 810, 870, 970, 1020, 1080, 1130, 2869, 2940, and 32-3600 cm⁻¹(broad); NMR(CDCl₃): δ5.5(2H, m), 4.7(4H, broad s), 3.2-4.4(10H, m) and 0.7-2.4 ppm(45H, m).

EXAMPLE XI

Preparation of 1-Methanesulfonyloxy-9β,11α,15S-tetrahydropyranyloxyprost-13E-one.

A solution of 333 mg (0.53 mmol) of the material prepared as described in Example X in 3 ml of dry tetrahydrofuran was stirred at 0° under nitrogen as first 0.20 ml (2.5 mmol) of triethylamine and then 0.057 ml (0.62 mmol) of methanesulfonylchloride were added slowly via syringe. The resultant mixture was stirred for 1 hour at 0°, then diluted with ether and washed sequentially with 10% aqueous hydrochloric acid, brine and saturated aqueous sodium bicarbonate. The resultant solution was dried (MgSO₄) and evaporated in vacuo to yield 342 mg of an oil having the following structure:

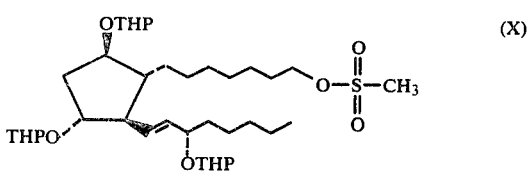
(X)

The structure of XI was confirmed as follows: tlc(ether) R$_f$ 0.49; IR(film) 810, 870, 970, 1020, 1080, 1130, 1170, 2860 and 2940 cm⁻¹; NMR(CDCl₃) same as the alcohol above with added δ3.0 ppm(3H, s).

EXAMPLE XII

Preparation of 1-Bromo-9β,11α,15S-tetrahydropyranyloxyprost-13E-ene.

Anydrous potassium carbonate (5 mg) and lithium bromide (30 mg) were added to a solution of 342 mg of XI in 3 ml of dry acetone. The resultant solution was stirred for 24 hours at room temperature under argon. Solvent was removed by evaporation in vacuo, and the residue was diluted with ether and then washed with water. The resultant extract was dried (Na₂SO₄) and evaporated in vacuo to yield 311 mg of product as an oil (XII) having the structural formula:

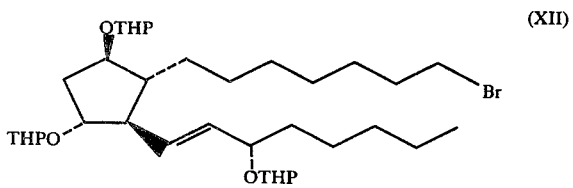
(XII)

The structure of XII was confirmed as follows: tlc(ether) R$_f$ 0.72; IR(film) 810, 870, 970, 1020, 1080, 1120, 1200, 2860 and 2940 cm⁻¹; NMR(CDCl₃) very similar to the compound prepared in Example XI.

EXAMPLE XIII

Preparation of 1-(Dimethylphosphono)prost-13E-ene-9β,11α,15S-triol.

Crude XII (311 mg) was dissolved in 3 ml of trimethylphosphite. A few mg of potassium carbonate was added and the resultant mixture was refluxed under argon. This reaction was monitored by periodically running a tlc(ether) analysis of a small aliquot. After 36 hour most of the starting material R$_f$0.7 was replaced by a major product R$_f$0.09. The solvent was removed by evaporation in vacuo and the residue was purified by chromatography on silica gel (benzene to ethyl acetate gradient elution) to yield 48 mg of a less polar component: tlc(system II) R$_f$ 0.42 and 120 mg of the major product:

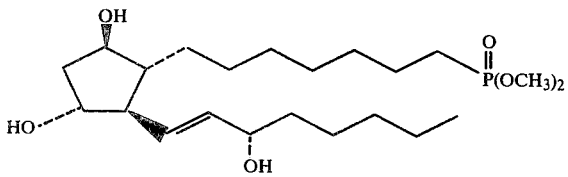
(TR 4235)

The structure of this composition was confirmed as follows: tlc(ether) R$_f$0.09, (system II) R$_f$0.37; IR(film)

810, 870, 1020, 1135, 1200, 1260, 1355, 1460, 1745, 2870 and 2950 cm$^{-1}$; NMR(CDCl$_3$) δ0.7–2.5(45H, m), 3.3–4(10H, m), 3.7(6H, d, J=11 Hz), 4.7(4H, broad s) and 5.5 ppm(2H, m).

The major product was dissolved in ca. 5 ml of acetic acid-water-tetrahydrofuran (65:35:10) and left for 36 hours at room temperature under argon. Solvent was removed by evaporation in vacuo and the residue was dissolved in ethyl acetate-ether (1:1) and washed with saturated aqueous sodium bicarbonate. The resultant solution was dried (NaSO$_4$) and evaporated in vacuo to yield 52 mg of the desired product (TR 4235) as an oily solid. This product did not move off of the baseline on tlc(system II) analysis and was not soluble in several ml of ether or ethyl acetate but was soluble in methanol.

EXAMPLE XIV

Preparation of
1-(Dimethylphosphono)prost-13E-ene-9α,11α,15S-triol.

In a sequence identical to that described in example XIII, 9,11,15-Tristetrahydropyranyl-PGF$_{1α}$-methyl ester (510 mg) was converted to the desired product having the composition:

(TR 4234)

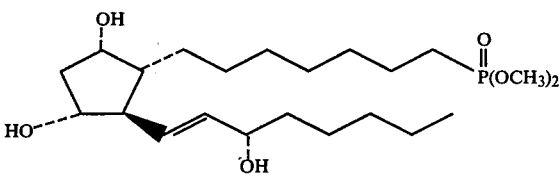

Spectra of all the intermediates were identical to those reported for Example XIII. All of the intermediates were slightly less polar in tlc analysis then in the previous example, however, the final product was very polar and not soluble in many organic solvents except methanol.

EXAMPLE XV

Preparation of
2-(7-Methanesulfonyloxyheptyl)-2-cyclopentenone.

A solution of 1.15 gm of 2-(7-Hydroxyheptyl)-2-cyclopentenone in 40 ml of dry THF was cooled to 0° with stirring under argon. Triethylamine (1.06 ml) was added, followed by 0.73 ml of distilled methanesulfonyl chloride. The reaction mixture was stirred for 2.5 hours at 0°, poured into ice water and extracted with ether. The ether extracts were washed with cold 10% hydrochloric acid and cold 5% aqueous sodium carbonate. They were dried (MgSO$_4$), filtered and evaporated in vacuo to afford 1.35 gm of a yellow oil. This oil was dissolved in ether and 0.5 ml triethylamine was added, followed by approximately 5.0 ml of methanol. The mixture was shaken and the layers separated whereupon the ether layer was washed with 10% hydrochloric acid, 5% aqueous sodium carbonate and brine. It was dried (MgSO$_4$), filtered and evaporated in vacuo to afford 988 mg of a yellow oil having the following structure:

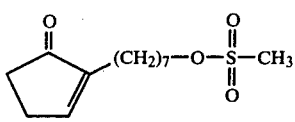

(XIII)

The structure of this composition was confirmed by nuclear magnetic resonance.

Analysis-NMR(CDCl$_3$): δ3.00(s, 3H, C$\underline{H}_3$), 4.23(t, J=6.0 Hz, 2, C$\underline{H}_2$-O), (m, 1, =C$\underline{H}$—).

EXAMPLE XVI

Preparation of 2-(7-Bromoheptyl)-2-cyclopentenone.

A solution of 988 mg of the crude material prepared in Example XV in 7.5 ml dry acetone was stirred at 25° under argon with 1.80 gm lithium bromide for 18.25 hours at 25°. The acetone was removed in vacuo and water added to the residue. The mixture was extracted with 95:5 hexaneether. The extracts were washed with 10% aqueous sodium thiosulfate and brine, dried over MgSO$_4$, filtered and evaporated in vacuo to afford 737 mg of a yellow oil having the following structure:

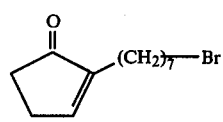

(XIV)

The structure of this composition was confirmed by nuclear magnetic resonance, infrared and mass spectral analysis.

Analysis-NMR(CDCl$_3$) δ3.40(t, J=7.0 Hz, 2, C$\underline{H}_2$Br), 7.33 (m, 1, =C$\underline{H}$—)

IR(CHCl$_3$): 5.92, 6.06μ

Mass Spectrum: m/e 260, 258(M+).

EXAMPLE XVII

Preparation of
dl-1-Bromo-16,20-methanoprost-13E-en-9-one.

A solution of 1.13 gm of 1-iodo-3-cyclohexyl-1-tran-spropene (4.50 mmol) in 22 ml dry ether was cooled to −78° with stirring under argon and treated with 8.60 ml of 1.07 M t-butyllithium in pentane. The reaction mixture was stirred for 2 hours at −78°, and transferred into a stirred, −78° solution of 532 mg of copper(I)pentyne in 12 ml dry ether (solubilized at 25° by addition of 1.50 ml hexamethylphosphorus triamide). The resultant complex was stirred for 0.5 hour at 1.0 gm (3.86 mmol) of the material prepared in Example XVI in 4.5 ml dry ether was injected dropwise over 10 minutes. The reaction mixture was stirred for 0.5 hours at −78°, 1.5 hours at −10° and 0.5 hour at 0°. The reaction mixture was processed as described, infra, in Example XVIII, excluding the treatment with acetic acid/water/THF to yield 1.55 gm of a yellow oil. Chromatography (85:15 silicic acid-Celite, benzene→ethyl acetate gradient elution) afforded 1.19 gm of a yellow oil, R$_f$ (system II) 0.58.

The material had the following composition:

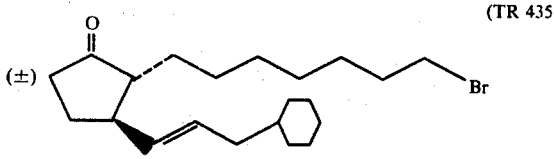

(TR 4353)

The composition of this material was confirmed by nuclear magnetic resonance, infrared and mass spectral analysis.

Analysis-NMR(CDCl₃): δ3.47(t, J=7, 2, C$\underline{H}_2$Br) 5.50(m, 2, trans-olefinic-$\underline{H}$)

IR(CHCl₃): 5.80, 10.40μ

Mass Spectrum: m/e 384, 382(M+), 366, 364(M+-H₂O).

EXAMPLE XVIII

Preparation of dl-1-Bromo-15S-hydroxy-18,19,20-trisnor-8,12-iso-prost-13E-en-9-one and dl-1-Bromo-15S-hydroxy-18,19,20-trisnorprost-13E-en-9-one.

A solution of 404 mg of dl-1-iodo-3-(1-ethoxyethoxy)1-trans-pentene in 6.3 ml of ether was cooled to −78° with stirring under argon whereupon 2.68 ml of 1.06 M t-butyllithium in pentane was injected. The reaction mixture was stirred for 2.0 hours at −78° then transferred into a stirred, −78° solution of 168 mg of copper-(I)pentyne in 3.2 ml of ether (solubilized at 25° by the addition of 0.505 ml of hexamethylphosphorous triamide). The resultant complex was stirred for 0.5 hour at −78° whereupon 315 mg of the material prepared in Example XVI in 3.2 ml of dry ether was injected dropwise. The reaction mass was stirred for 0.5 hour at −78°, 1.5 hours at −10°, 0.5 hour at 0° and 0.5 hour at 25°. The reaction mixture was quenched by the addition of cold 20% aqueous ammonium sulfate after which the layers were separated and the aqueous layer extracted with ether. The ether extracts were washed with cold 2% V/V sulfuric acid-water, saturated aqueous sodium bicarbonate and brine. The extracts were dried (MgSO₄), filtered and ether was removed by evaporation in vacuo to afford 420 mg of a yellow oil. The oil was stirred with 12 ml 65:35 acetic acid-water and 112 ml THF for 20 hours at 25°. The solvents were evaporated in vacuo and water added to the residue whereupon the mixture was extracted with ether. The ether extracts were washed with saturated aqueous sodium bicarbonate and brine, dried, filtered and evaporated to afford 349 mg of a yellow oil. Chromatography on Silica Gel (benzene→ethyl acetate gradient elution) 53 mg of

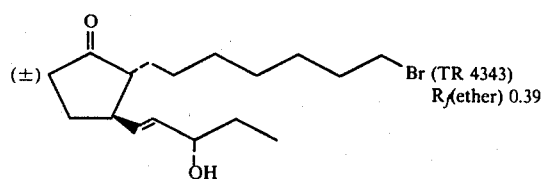

Br (TR 4343)
R_f(ether) 0.39 and 53 mg of

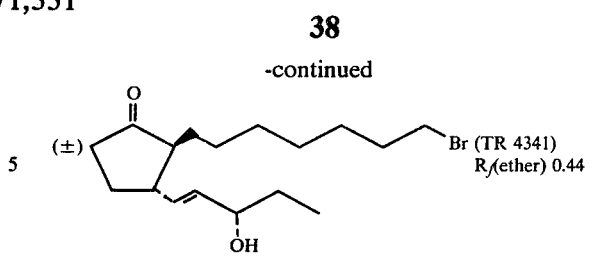

Br (TR 4341)
R_f(ether) 0.44 as clear oils.

The composition of these materials was confirmed by nuclear magnetic resonance, infrared and mass spectral analysis:

Analysis (TR 4343)-NMR(CDCl₃): δ0.92(t, J=7, 3, C$\underline{H}_3$), 3.45(t, J=6; 2, C$\underline{H}_2$Br), 4.10(m, 1, C$\underline{H}$OH), 5.67(m, 2, trans-olefinic-$\underline{H}$)

IR(CHCl₃): 2.78, 2.90 (broad), 5.78, 10.4μ

Mass Spectrum: m/e 346, 344(M+), 328, 326(M+-H₂O).

Analysis (TR 4341)-NMR(CDCl₃): 0.94(t, J=7; 3, C$\underline{H}_3$), 3.48(t, J=6; 2, C$\underline{H}_2$Br), 4.12(m, 1, C$\underline{H}$OH), 5.70(m, 2, trans-olefinic-H)

IR(CHCl₃): 2.78, 2.90(broad), 5.78, 10.4μ

Mass Spectrum: m/e 346, 344(M+), 328, 326(M+—H₂O).

EXAMPLE XIX

Preparation of 1-Bromo-15S-hydroxyprost-13E-en-9-one and 1-Bromo-15S-hydroxy-8,12-iso-prost-13E-en-9-one.

A solution of 642 mg of 1-Iodo-3S-(1-ethoxyethoxy)-trans-1-octene (1.98 mmol) in 13.0 ml of ether was cooled to −78° with stirring under argon whereup 5.20 ml of 1.06 M t-butyllithium in pentane was injected. The reaction mixture was stirred for 2 hours at −78°, then transferred into a stirred, −78° solution of 330 mg of copper(I)pentyne in 6.3 ml of ether (solubilized at 25° with 0.995 ml hexamethylphosphorous triamide). The resultant complex was stirred for 0.5 hour at −78°, then injected with a solution of 622 mg of the material prepared in Example XVI in 5 ml ether. The reaction mixture was stirred for 0.5 hour at −78°, 1.5 hours at −10°, and 0.5 hour at 0°. The reaction mixture was poured into cold 20% aqueous ammonium sulfate, then processed as described in Example XVIII to afford 1.13 gm of a yellow oil. The yellow oil was stirred with 32 ml of 65:35 acetic acid-water and 3.0 ml of THF for 1 hour at 25°, then processed as described in Example XVIII to yield 155 mg of

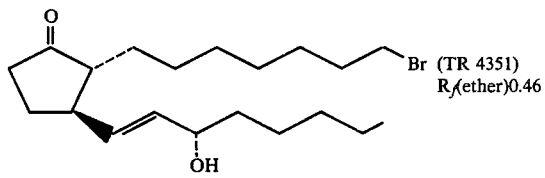

Br (TR 4351)
R_f(ether)0.46 and 232 mg of

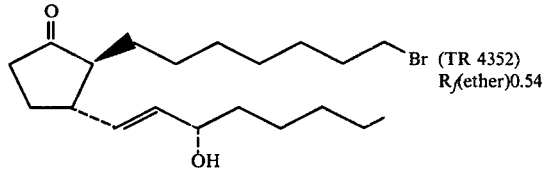

Br (TR 4352)
R_f(ether)0.54 as yellow oils.

The composition of these compounds was confirmed by nuclear magnetic resonance, infrared and mass spectral analysis.

Analysis (TR 4351)-NMR(CDCl₃): 0.90(broad t, 3, CH₃), 3.47(t, J=7; 2, CH₂Br), 4.16(m, 1, CHOH), 5.68(m, 2, trans-olefinic-H)
IR(CHCl₃): 2.78, 2.90(broad), 5.78, 10.40μ; [α]$_D$−43.2°(c 0.99, CHCl₃)
Mass Spectrum m/e 388, 386(M+), 370, 368(M+−H₂O).

Analysis (TR 4352)-NMR(CDCl₃): 0.91(broad t, 3, CH₃), 3.47(t, J=7; 2, CH₂Br), 4.16(m, 1, CHOH), 5.68(m, 2, trans-olefinic-H)
IR(CHCl₃): 2.78, 2.90(broad), 5.78, 10.40μ; [α]$_D$+41.5°(c 0.79, CHCl₃)
Mass Spectrum: m/e 338, 386(M+), 3.70, 3.68(M+−H₂O).

EXAMPLE XX

A solution of 460 mg 1-iodo-3R-(1-ethoxyethoxy)-3-cyclohexyl-1-trans-propene in 10 ml of dry ether was cooled to −78° with stirring under argon and 3.84 ml of 1.06 M t-butyllithium in pentane injected. The reaction mixture was stirred for 2 hours at −78° and transferred to a stirred, −78° solution of 240 mg of copper(I)pentyne in 4.60 ml of ether (solubilized at 25° by addition of 0.72 ml of hexamethylphosphorous triamide). The resultant complex was stirred for 0.5 hour at −78° whereupon a solution of 450 mg of the material prepared in Example XVI in 3.5 ml of ether was added dropwise. The reaction mixture was stirred for 0.5 hour at −78°, 1.5 hours at −10° and 0.5 hour at 0° then quenched and processed as described for the preparation of TR 4343 and TR 4341 to yield 840 mg of yellow oil. The oil was stirred for 1 hour at 25° with 24 ml of 65:35 acetic acid-water and 2.5 ml THF and then processed as described for the preparation of TR 4343 and TR 4341 to yield 93.5 mg of a yellow oil of the following composition:

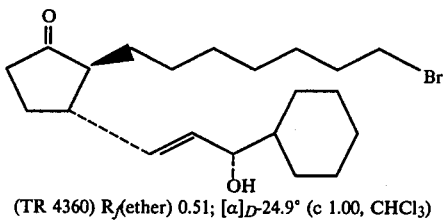

(TR 4360) R$_f$(ether) 0.51; [α]$_D$-24.9° (c 1.00, CHCl₃)

The remainder of the material was further purified by preparative thin layer chromatography (Silica Gel 60 F254, ether eluate, chloroform bond extraction) to afford 56.9 mg of a yellow oil having the following composition:

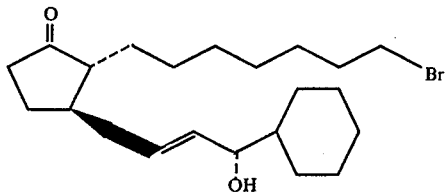

(TR 4361) R$_f$(ether) 0.59; [α]$_D$ +29.1° (c 1.00, CHCl₃)

The structure of these compositions was confirmed by nuclear magnetic resonance, infrared and mass spectral analysis.

Analysis (TR 4360)-NMR(CDCl₃): δ3.46(t, J=7; 2, CH₂Br), 3.95(m, 1, CHOH), 5.70(m, 2, trans-olefinic-H)
IR(CHCl₂): 2.78, 2.90(broad), 5.78, 10.4μ
Mass Spectrum: m/e 400, 398(M+), 382, 380(M+−H₂O).

Analysis (TR 4361)-NMR(CDCl₃): δ3.50(t, J=7; 2, CH₂Br), 3.96(m, 1, CHOH), 3.70(m, 2, trans-olefinic-H)
IR(CHCl₃): 2.78, 2.90, 5.78, 10.40μ
Mass Spectrum: m/e 400, 398(M+), 382, 380(M+−H₂O).

EXAMPLE XXI

Preparation of
1-Bromo-15R-hydroxy-16-methyl-18,19,20-trisnor-prost-13E-en-9-one and
1-Bromo-15R-hydroxy-16-methyl-18,19,20-trisnor-8,12-iso-prost-13E-en-9-one A solution of 585 mg of 1-iodo-3S-(1-ethoxyethoxy)-4-methyl-1-trans-pentene in 13.0 ml of ether was cooled to −78° with stirring under argon and injected with 5.28 ml of 1.06 M t-butyllithium in pentane. The reaction mixture was stirred at −78° for 2 hours and transferred into a stirred, −78° solution of 330 mg of copper-(I)pentyne in 6.3 ml of ether (solubilized at 25° by addition of 0.99 ml hexamethylphosphorous triamide). The resultant complex was stirred for 0.5 hour at −78°, whereupon a solution of 622 mg of the material prepared in Example XVI was added dropwise. The reaction mixture was stirred for 0.5 hour at −78°, 1.5 hours at −10° and 0.5 hour at 0° then quenched and processed as described for the preparation of TR 4343 and TR 4341 to yield 1.0 gm of an orange oil. The oil was stirred for 1 hour at 25° with 28 ml of 65:35 acetic acid-water and 2.8 ml THF. The reaction mixture was processed as described for the preparation of TR 4343 and TR 4341 to provide 148 mg of:

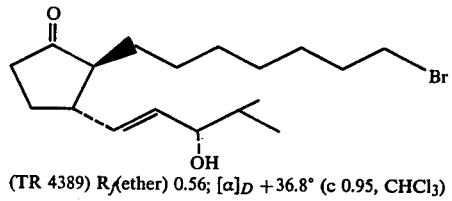

(TR 4389) R$_f$(ether) 0.56; [α]$_D$ +36.8° (c 0.95, CHCl₃)

and 177 mg of

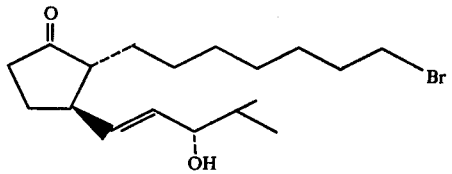

(TR 4384) R$_f$(ether) 0.49; [α]$_D$-80.6° (c 0.98, CHCl₃)

as yellow oils. The structure of these compositions was confirmed by nuclear magnetic resonance, infrared and mass spectral analysis.

Analysis (TR 4389)-NMR(CDCl₃): δ0.94(pair of overlapping doublets, 6, CH₃), 3.47(t, J=7; 2, CH₂Br), 3.92(m, 1, CHOH), 5.69 (m, 2, trans-olefinic-H)
IR(CHCl₃): 2.78, 2.90(broad), 5.78, 10.4μ
Mass Spectrum: m/e 360, 358(M+), 342, 340(M+−H₂O), 317, 315.

Analysis (TR 4384)-NMR(CDCl₃): δ0.92(overlapping pair of doublets, 6, CH₃), 3.49(t, J=7; 2, CH₂Br), 3.96(m, 1, CHOH), 5.72(m, 2, trans-olefinic-H)
IR(CHCl₃): 2.78, 2.90(broad), 5.78, 10.4μ

Mass Spectrum: m/e 360, 358(M+), 317, 315(M+−C$_3$H$_7$).

EXAMPLE XXII

Preparation of 1-Bromo-8,12-prost-13E-ene-9β,15S-diol and 1-Bromo-8,12-iso-prost-13E-ene-9β,15S-diol A solution of 81 mg of TR 4352 in 6.6 ml of methanol was cooled to 0° with stirring under argon. A solution of 226 mg of sodium borohydride in 22 ml of cold methanol was added dropwise over 5 minutes. The reaction mixture was stirred for 20 minutes and for 1 hour at 25° whereupon the methanol was evaporated in vacuo and water added to the residue. The mixture was extracted with 1:1 ethyl acetateether whereupon the extracts were washed with brine, dried (MgSO$_4$) and filtered. Solvents were removed in vacuo to yield 85.6 mg of a clear oil. To insure that the reaction had gone to completion, the crude product was resubmitted to the above-described reaction conditions and processed as previously described to yield 79.4 mg of crude product as a clear oil. Chromatography of this material (85:15 silicic acid-Celite, benzene → ethyl acetate gradient elution) allowed isolation of 12.0 mg of:

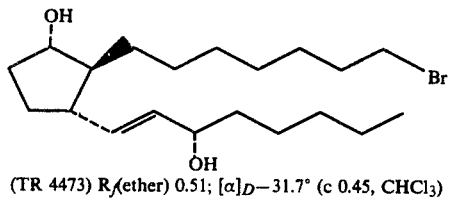

(TR 4473) R$_f$(ether) 0.51; [α]$_D$ −31.7° (c 0.45, CHCl$_3$)

and 36.3 mg of

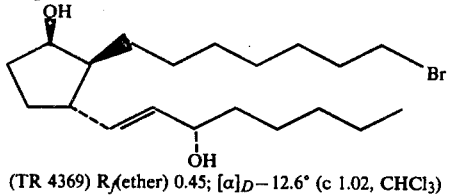

(TR 4369) R$_f$(ether) 0.45; [α]$_D$ −12.6° (c 1.02, CHCl$_3$)

as clear oils, respectively.

The structure of these compositions was confirmed by nuclear magnetic resonance, infrared and mass spectral analysis.

Analysis (TR 4473)-NMR(CDCl$_3$): δ0.90(broad, t, 3, CH$_3$), 3.48(t, J=7; 2, CH$_2$Br), 4.29(m, 2, CHOH), 5.45(dd, J=6, 16 Hz, C$_{13}$-H) 5.90(dd, J=8, 16 Hz, C$_{14}$-H)

IR(CDCl$_3$): 2.88, 2.90(broad), 10.40μ

Mass Spectrum: m/e 372, 370(M+−H$_2$O), 301, 299(M+−H$_2$O−C$_5$H$_{11}$).

Analysis (TR 4369)-NMR(CDCl$_3$): δ0.90(broad t, 3, CH$_3$), 3.48(t, J=7 Hz, 2, CH$_2$Br), 4.10(m, 2, CHOH), 5.63(m, 2, trans-olefinic-H)

IR(CDCl$_3$): 2.28, 2.90(broad), 10.40μ

Mass Spectrum: m/e 372, 370(M+−H$_2$O), 301, 299(M+−H$_2$O−C$_5$H$_{11}$).

EXAMPLE XXIII

Preparation of 1-Bromoprost-13E-en-9RS,15S-diol

A solution of 55.7 mg of TR 4351 in 4.5 ml of methanol was cooled to 0° with stirring under argon. A solution of 155 mg of sodium borohydride in 75 ml cold methanol was added dropwise whereupon the reaction mixture was stirred for 20 minutes at 0° and for 1 hour at 25°. The methanol was evaporated in vacuo and water was added to the residue at which point the mixture was extracted with 1:1 ethyl acetate-ether. The extracts were washed with brine, dried (MgSO$_4$), filtered and the solvents removed in vacuo to afford 56.9 mg of a clear oil. The tlc (ether, silica gel 60 plates) of the mixture showed a slight difference in polarity (α, R$_f$ 0.435; β, R$_f$0.38) but column chromatography afforded no separation. The mixture of compounds (11-deoxy-PGF$_{1α}$ and 11-deoxy-PGF$_{1β}$) prepared as described in this Example is represented by the formula:

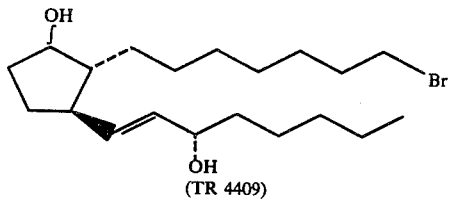

(TR 4409)

The structure of this material was confirmed by nuclear magnetic resonance, mass spectral and infrared analysis.

Analysis-NMR(CDCl$_3$): δ0.91(broad t, 3, CH$_3$), 3.46(t, 2, J=7.0 Hz, CH$_2$Br), 4.06(m, 2, CHOH), 5.60(m, 2, trans-olefinic-H)

IR(CHCl$_3$): 2.78, 2.90(broad), 10.40μ.

EXAMPLE XXIV

Preparation of 2-Decarboxy-2-methanesulfonylmethyl-15-depentyl-15-cyclohexyl-PGF$_{1α}$-9,11,15-tris-tetrahydropyran-2-yl ether A solution of 311 mg 15-Depentyl-15-cyclohexyl-PGF$_{1α}$-methyl ester prepared as in Example XXXVIII, infra, in 6.5 ml of ether was stirred under argon and 0.125 ml dihydropyran (DHP) was added, followed by a small spatula of p-toluenesulfonic acid. Additional DHP was added after 1.0 hour (0.1 ml) and 1.5 hours (0.1 ml). The reaction mixture was diluted with ether and shaken with saturated aqueous sodium bicarbonate and brine. The ether layer was dried (MgSO$_4$) and the ether was removed by evaporation in vacuo to afford 521 mg of 15-Depentyl-15-cyclohexyl-PGF$_{1α}$-methyl ester-9,11,15-tris-tetrahydropyranyl ether as a yellow oil; R$_f$(ether, Silica Gel 60 plates) 0.62.

A solution of 521 mg of crude product in 3.0 ml THF was added dropwise to a stirred, −10° solution of 0.9 ml Red-AL (70% in benzene) in 1.2 ml THF. The reaction mixture was stirred for 2.0 hours at 0° and for 0.5 hour at 25°0 whereupon the reaction mixture was poured slowly into cold 10% hydrochloric acid (HCl) and diluted with ether. The ether layer was shaken with saturated aqueous sodium bicarbonate (NaHCO$_3$), brine, then dried (MgSO$_4$), filtered and ether removed in vacuo to yield 429 mg of crude 2-Decarboxy-2-hydroxymethyl-15-depentyl-15-cyclohexyl-PGF$_{1α}$-9,11,15-tristetrahydropyranyl ether as a light yellow oil, R$_f$(ether) 0.38.

A solution of 274 mg crude product in 1.6 ml dry THF was cooled to 0° with stirring under argon. Triethylamine (0.16) was added followed by 0.055 ml of methanesulfonyl chloride. The reaction mixture was stirred for 1.5 hours at 0°, then diluted with ether whereupon the solution was washed with 10% HCl, saturated aqueous NaHCO$_3$ and brine. The solution was dried (MgSO$_4$), then filtered and evaporated in vacuo to yield 570 mg of the desired composition having the following structural formula:

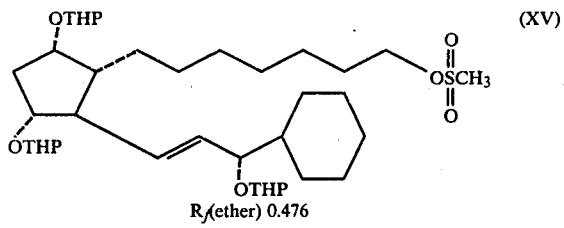

R_f(ether) 0.476

The structure of this material was confirmed by nuclear magnetic resonance.

Analysis-NMR(CDCl$_3$): δ3.05(s, 3, C$\underline{H}_3$), 4.76(m, 3, OC$\underline{H}$O), 5.52(m, 2, trans-olefinic-$\underline{H}$).

EXAMPLE XXV

Preparation of
2-Decarboxy-2-bromoethyl-15-depentyl-15-cyclohexyl-PGF$_{1\alpha}$-9,11,15-tris-tetrahydropyranyl ether A solution of 286 mg of the crude material prepared in Example XXIV in 3.0 ml of dry acetone was stirred at 25° under argon and 5 mg of anhydrous potassium carbonate was added, followed by 87 mg of lithium bromide. The reaction mixture was stirred for 18 hours at 25° under argon. The acetone was evaporated in vacuo and water added to the residue whereupon the mixture was extracted with 1:1 etherhexane. The extracts were washed with 10% aqueous sodium thiosulfate and brine, then dried (MgSO$_4$), filtered and evaporated in vacuo to afford 238 mg of a yellow oil. A nmr spectrum indicated that the reaction had not gone to completion, so the crude product was resubmitted to the above reaction conditions and processed (as above) after 16 hours at 25° to afford 218 mg of a yellow oil. A nmr spectrum indicated approximately a 30% loss of the tetrahydropropyranl ether moieties. The crude product was dissolved in 5.0 ml ether and reprotected by stirring with 0.20 ml of dihydropyran and a small spatula of p-toluene-sulfonic acid for 18 hours at 25°. The reaction mixture was processed as described for the preparation of the material prepared in Example XXXX, infra, to yield 259 mg of an orange oil of the following structure:

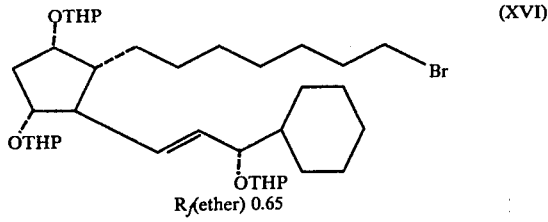

R_f(ether) 0.65

The structure of this material was confirmed by nuclear magnetic resonance.

Analysis-NMR(CDCl$_3$): δ3.51(t, J=7.0 Hz, 2, C$\underline{H}_2$Br), 4.80 (m, 3, OC$\underline{H}$O), 5.52(m, 2, trans-olefinic-$\underline{H}$).

EXAMPLE XXVI

Preparation of
2-Decarboxy-2-ethylthiomethyl-15-depentyl-15-cyclohexyl-PGF$_{1\alpha}$-9,11,15-tris-tetrahydropyranyl ether Ethyl mercaptan (0.1 ml, 1.3 mmol) was injected dropwise into a stirred, 25° slurry of 62.5 mg of sodium hydride (50% in oil) in 1.5 ml dry THF. The reaction mixture was stirred for 1 hour at 25°, then a solution of 259 mg of the material prepared in Example XXV in 1.0 ml THF was injected dropwise. The reaction mixture was stirred for 3 hours at 25°, then diluted with water and extracted twice with chloroform. The chloroform extracts were washed with brine, then dried (Na$_2$SO$_4$), filtered and evaporated in vacuo to yield 220 mg of an orange oil having the following structure:

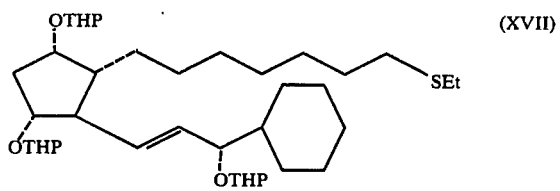

The structure of this material was confirmed by nuclear magnetic resonance.

Analysis-NMR(CDCl$_3$): δ1.58(t and q overlapping, 4, C$\underline{H}_2$SC$\underline{H}_2$), 4.76(m, 3, OC$\underline{H}$O), 5.46(m, 2, trans-olefinic-$\underline{H}$).

EXAMPLE XXVII

Preparation of
1-(Ethylthio)-16,20-methanoprost-13E-ene-9α,1-1α,15R-triol

The crude material prepared in Example XXIV (220 mg) was stirred with 12.0 ml 65:35:10 acetic acid-water-THF for 17.5 hours under argon and for 24 hours at 33°. The solvents were removed by evaporation in vacuo and water was added to the residue. The mixture was extracted with ether whereupon the ether extracts were washed with saturated aqueous sodium bicarbonate and brine, then dried (MgSO$_4$), filtered and evaporated in vacuo to yield 148 mg of a yellow oil. The oil was chromatographed on 85:15 silicic acid-Celite (benzene ethyl acetate gradient elution) to afford 50 mg of an oily white solid of the following structure:

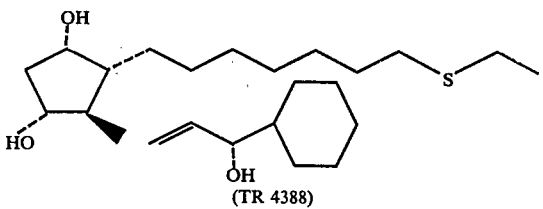

(TR 4388)

The structure of this material was confirmed by nuclear magnetic resonance, mass spectral and infrared analysis.

Analysis-NMR(CDCl$_3$): δ2.56(m, 7, C$\underline{H}_2$SC$\underline{H}_2$, OH), 5.56(m, 2, trans-olefinic-$\underline{H}$), 4.28(m, 1, C$_9$-$\underline{H}$), 3.90(m, 2, C$_{11}$-$\underline{H}$, C$_{15}$-$\underline{H}$)

IR(CHCl$_3$): 2.78, 2.95(broad), 6.85, 10.40μ

Mass Spectrum: m/e 398(M+), 380(M+—H$_2$O), 362(M+—2H$_2$O), 344(M+—3H$_2$).

EXAMPLE XXVIII

Preparation of
2-Decarboxy-2-hydroxymethyl-15-depentyl-15-cyclohexyl-PGF$_{1\beta}$-9,11,15-tris-tetrahydropyranyl ether A solution of 380 mg of 15-Depentyl-15-cyclohexyl-PGF$_{1\beta}$-methyl ester as prepared in Example XXXVIII, infra, in 7.5 ml of dry ether was stirred at 25° under argon and 0.15 ml dihydropyran was injected, followed by a small spatula of p-toluenesulfonic acid. After 1 hour at 25°, 0.2 ml additional dihydropyran was added whereupon the reaction mixture was stirred an additional 5.25 hours at 25°, then processed as described in Example XXXX, infra, to afford 652 mg of 15-Depentyl-15-cyclohexyl-PGF$_{1\beta}$-methyl ester-9,11,15-tris-tetrahydropyranyl ether as a yellow oil, R$_f$(ether) 0.63.

A solution of 652 mg crude product in 4.0 ml dry THF was added dropwise to a −10°, stirred solution of 1.10 ml Red-AL (70% in benzene) in 1.5 ml THF. The reaction mixture was stirred for 2.0 hours at 0° and for 0.5 hour at 25° under argon, then processed as described for the preparation of 2-decarboxy-2-hydroxymethyl-15-depentyl-15-cyclohexyl-PGF$_{1\alpha}$-9,11,15-tristetrahydropyranyl ether to afford 561 mg of a clear oil having the following structure:

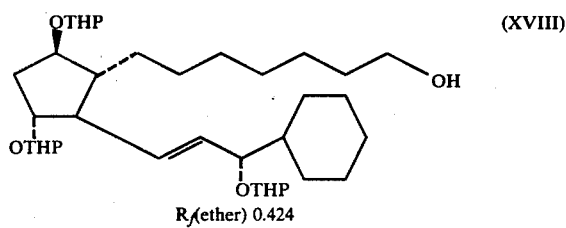

R$_f$(ether) 0.424

The structure of this material was confirmed by nuclear magentic resonance.

Analysis-NMR: δ7.42(m, 3, OC$\underline{H}$O), 5.56(m, 2, trans-olefinic-$\underline{H}$) no δ3.66 signal observed.

EXAMPLE XXIX

Preparation of 2-Decarboxy-2-ethylthiomethyl-15-depentyl-15-cyclohexyl-PGF$_{1\beta}$-tris-tetrahydropyranyl ether A solution of 394 mg of the material prepared in Example XXVIII in 2.5 ml dry THF was cooled to 0° with stirring under argon. Triethylamine (0.23 ml) was injected, followed by 0.08 ml of mesyl chloride whereupon the reaction mixture was stirred for 1 hour at 0° and then processed as described for the preparation in Example XXIV, supra, to yield 416 mg of 1-Decarboxy-1-methanesulfonyloxymethyl-15-depentyl-15-cyclohexyl-PGF$_{1\beta}$-tris-tetrahydropyranyl ether as a clear oil.

A solution of 416 mg product in 5.5 ml dry acetone was stirred at 25° under argon with potassium carbonate (80 mg) followed by 305 mg of lithium bromide being added. The reaction mixture was stirred for 18 hours at 25°, and then processed as described in Example XXV, supra, to yield 365 mg of 1-Decarboxy-1-Bromomethyl-15-depentyl-15-cyclohexyl-PGF$_{1\beta}$-tristetrahydropyranyl ether as a clear oil, R$_f$(ether) 0.66.

Ethyl mercaptan (0.14 ml) was injected dropwise into a 25°, stirred slurry of 88 mg of sodium hydride (50% in oil) in 2.0 ml of dry THF under nitrogen. After stirring for 1 hour at 25°, a solution of 365 mg of product in 1.5 ml THF was injected. The reaction mixture was stirred for 3 hours at 25°, then processed as described for the preparation in Example XXVI to yield 345 mg of a yellow oil having the following structure:

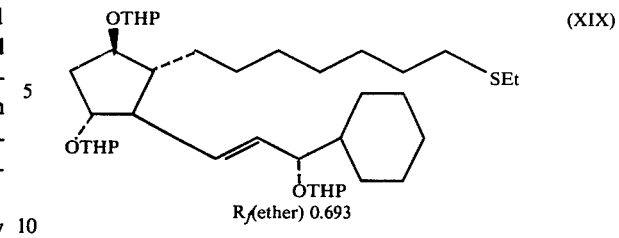

R$_f$(ether) 0.693

The structure of this material was confirmed by nuclear magnetic resonance.

Analysis-NMR(CDCl$_3$): δ2.60(m, 4, C$\underline{H_2}$SC$\underline{H_2}$), 4.76(m, 3, OC$\underline{H}$O), 5.58(m, 2, trans-olefinic-$\underline{H}$).

EXAMPLE XXX

Preparation of 2-Decarboxy-2-ethylthiomethyl-15-depentyl-15-cyclohexyl-PGF$_{1\beta}$.

The crude material prepared in Example XXIV (345 mg) was stirred with 20 ml 65:35:10 (V/V) acetic acid-water-THF for 72 hours at 25°. The reaction mixture was processed as described in Example XXVII to yield 43 mg of a white solid (mp 126°–129°) having the following structure:

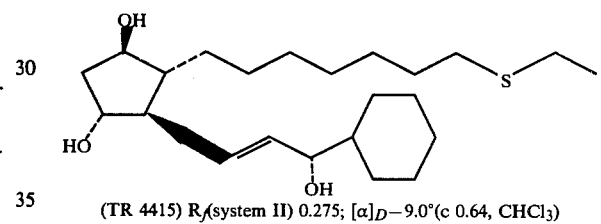

(TR 4415) R$_f$(system II) 0.275; [α]$_D$ −9.0°(c 0.64, CHCl$_3$)

The structure of this material was confirmed by nuclear magnetic resonance, mass spectral and infrared analysis.

Analysis-NMR(CDCl$_3$): δ2.56(t overlapping q, 4, C$\underline{H_2}$SC$\underline{H_2}$), 1.16(t, J=7.0 Hz, SCH$_2$C$\underline{H_3}$), 5.54(m, 2, trans-olefinic-$\underline{H}$).

IR(CHCl$_3$): 2.78, 2.95(broad), 10.40μ.

EXAMPLE XXXI

Preparation of 2-Decarboxy-2-ethylthiomethyl-15-deoxy-PGF$_{1\alpha}$-bis-9,11-tetrahydropyranyl ether.

A solution of 325 mg of 15-Deoxy-PGF$_{1\alpha}$-methyl ester was dissolved in 8.5 ml ether and stirred at 25° under argon. Dihydropyran (1.1 ml) was added, followed by a small spatula of p-toluenesulfonic acid. The reaction mixture was stirred for 1.25 hours at 25°, then processed as described in Example XXXX, infra, to afford 550 mg of the 9,11-bistetrahydropyranyl ether of 15-Deoxy-PGF$_{1\alpha}$ methyl ester as a clear oil, R$_f$(ether) 0.642. A solution of 550 mg of protected 15-Deoxy-PGF$_{1\alpha}$ methyl ester in 3.5 ml THF was added dropwise to 1.05 ml Red-AL (70% in benzene) and 1.5 ml THF at −10° under argon whereupon the reaction mixture was stirred for 2.0 hours at 0° and for 0.5 hour at 25° and diluted with ether and processed as described for the preparation in Example XXIV to afford 441 mg of crude 2-Decarboxy-2-hydroxymethyl-15-deoxy-PGF$_{1\alpha}$-9,11-bis-tetrahydropyranyloxy ether as a clear oil, R$_f$(ether) 0.415.

A solution of 441 mg of the crude alcohol in 3.5 ml of dry THF was cooled to 0° under argon and 0.34 ml of triethylamine was added, followed by 0.11 ml methanesulfonyl chloride whereupon the reaction mixture was stirred for 1 hour at 0° and processed as described in Example XXIV to afford 454 mg of crude mesylate; R_f(ether) 0.492. The mesylate was dissolved in 7.5 ml dry acetone and stirred under argon with 105 mg anhydrous potassium carbonate and 410 mg of lithium bromide whereupon the reaction mixture was stirred for 18 hours at 25° and processed as described in Example XXV to yield 420 mg of crude bromide as a yellow oil, R_f(ether) 0.66.

Ethyl mercaptan (0.20 ml) was injected dropwise into a 25°, stirred slurry of 125 mg of sodium hydride 950% in oil) in 3.0 ml THF. The reaction mixture was stirred for 1.0 hour at 25° and a solution of 420 mg of the crude bromide in 2.0 ml THF was injected. The reaction mixture was stirred for 3.0 hours at 25° and processed as described in Example XXVI to yield 438 mg of a clear oil having the following composition:

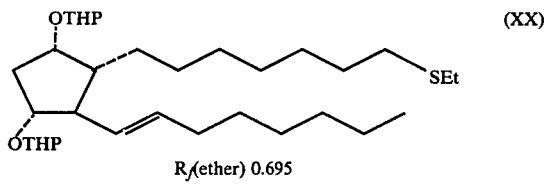

R_f(ether) 0.695

The structure of this material was confirmed by nuclear magnetic resonance.

Analysis-NMR(CDCl_3): δ0.88(broad t, 3, C$\underline{H}_3$), 2.56(m, 4, C$\underline{H}_2$SC$\underline{H}_2$), 4.69(m, 2, OC$\underline{H}$O), 5.42(m, 2, trans-olefinic-$\underline{H}$).

EXAMPLE XXXII

Preparation of 1-(Ethylsulfoxy)prost-13E-en-9α,11α-diol.

A solution of 68 mg of the material prepared in Example XXXXIII, infra, was dissolved in 1.5 ml of methanol was added dropwise to a solution of 41.3 mg of sodium metaperiodate in 3.5 ml of water (cooled with an ice-bath). The reaction mixture was stirred for 3 hours at 0° and for 16 hours at 25° whereupon the reaction mixture was filtered and the filtrate was extracted twice with methylene chloride. The extracts were dried (Na_2SO_4), filtered and evaporated in vacuo to afford 59 mg of a clear oil. Thin-layer chromatography (Silica Gel 60 plates, "system II" eluent) showed a spot corresponding to the desired product as well as starting material. The crude product was dissolved in 1.5 ml of methanol and added dropwise to a chilled solution of 20 mg of sodium-meta-periodate in 3.0 ml of water. The reaction mixture was stirred for 2.0 hours at 0° and for 1 hour at 25° whereupon the mixture was processed as described above to yield 55.7 mg of the crude product as a clear oil. The crude product was dissolved in a minimum amount of chloroform and streaked onto a 2.0 mm Silical Gel 60 F254 preparative tlc plate. The plate was eluted with system II and the most polar bond was extracted with distilled acetone to afford 30.2 mg of a clear oil of the following composition:

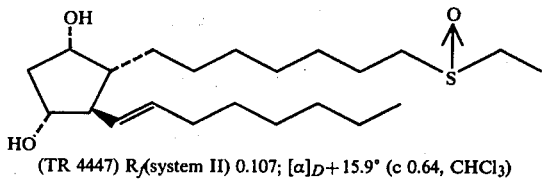

(TR 4447) R_f(system II) 0.107; [α]_D+15.9° (c 0.64, CHCl_3)

The structure of this material was confirmed by nuclear magnetic resonance, mass spectral and infrared analysis.

Analysis-NMR(CDCl_3): δ0.90(broad t, 3, pentyl-C$\underline{H}_3$), 2.74 (m, 4, C$\underline{H}_2$SC$\underline{H}_2$), 3.03(broad s, 2, O$\underline{H}$), 3.97(m, 1, C_{11}-$\underline{H}$), 4.20(m, 1, C_9-$\underline{H}$)

IR(CHCl_3): 2.78, 2.90(broad), 10.40μ Mass Spectrum: m/e 386(M+), 369(M+-OH), 369(M+-H_2O).

EXAMPLE XXXIII

Preparation of 1-(Ethylsulfonyl)prost-13E-ene-9α,11α-diol.

A solution of 49.4 mg of the material prepared in Example XXXXIII, infra, in 1.2 ml dry ether was cooled to 0° with stirring under argon. A solution of 54.5 mg of 85% meta-chloroperbenzoic acid in 1.0 ml ether was added dropwise. The reaction mixture was stirred for 2.0 hours at 0° and then poured into 1:1 saturated aqueous NaHCO_3-1:1 etherethyl acetate. The layers were separated whereupon the organic layer was washed twice with saturated aqueous NaHCO_3, brine, then dried (MgSO_4), filtered and evaporated in vacuo to afford 60.4 mg of crude product as a clear oil. The crude product was purified by preparative tlc as described in Example XXXII to afford 31.4 mg of a clear oil having the following structure:

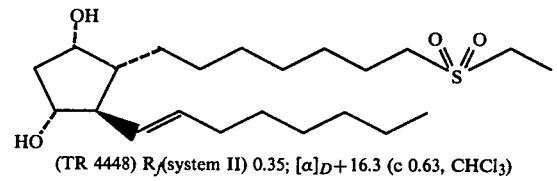

(TR 4448) R_f(system II) 0.35; [α]_D+16.3 (c 0.63, CHCl_3)

The structure of this material was confirmed by nuclear magnetic resonance, mass spectral and infrared analysis.

Analysis-NMR(CDCl_3): δ0.90(broad t, 3, pentyl-C$\underline{H}_3$), 2.56 (broad s, 2, O$\underline{H}$), 3.02(m, 4, C$\underline{H}_2$SC$\underline{H}_2$), 4.0(m, 1, C_{11}-$\underline{H}$), 4.26(m, 1, C_9-$\underline{H}$), 5.46(pair of dd, 2, trans-olefinic-$\underline{H}$)

IR(CHCl_3): 2.78, 2.90(broad), 7.65, 8.90, 10.40μ Mass Spectrum: m/e 385(M+-OH), 384(M+-H_2O), 367(M+), 366(M+-2H_2O).

EXAMPLE XXXIV

Preparation of dl-1-(ethylthio)-16,20-methanoprost-13E-en-9-one.

Ethyl mercaptan (0.1 ml) was injected dropwise into a slurry of 1.0 ml THF and 62.5 mg of sodium hydride (50% in oil). The resultant slurry was stirred for 1.0 hour at 25° whereupon a solution of 167 mg 1-Bromo-16,20-methanoprost-13E-en-9-one in 1.0 ml of THF was injected and the reaction mixture was stirred for 3.0 hours at 25°. The reaction mixture was quenched by the addition of 10% aqueous HCl and extracted twice with chloroform. The chloroform extracts were washed with saturated aqueous NaHCO_3 and then brine. They were dried (Na_2SO_4), filtered and evaporated in vacuo to yield 135 mg of an orange oil. The oil was chromatographed (85:15 silicic acid-Celite, benzene-ethyl acetate gradient elution) to afford 70.1 mg of a clear oil having the following structure:

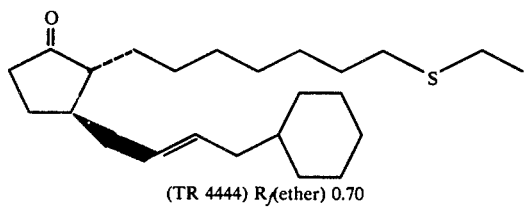

(TR 4444) R_f(ether) 0.70

The structure of this material was confirmed by nuclear magnetic resonance and mass spectral analysis.

Analysis-NMR(CDCl₃): δ0.92(t, J=7.0 Hz, CH₃), 2.56(m, 4, CH₂SCH₂), 5.52(pair of dd, 2, trans-olefinic-H).

EXAMPLE XXXV

Preparation of
1-(Ethylthio)-15R-hydroxy-16-methyl-18,19,20-trisnor-prost-13E-en-9-one and
1-(Ethylthio)-15R-hydroxy-16-methyl-18,19,20-trisnor-8,12-isoprost-13E-en-9-one.

A solution of 585 mg of 1-iodo-3R-(1-ethoxyethoxy)-4-methyl-1-trans-pentene (1.97 mmol) in 13.0 ml of dry ether was cooled to −78° with stirring under argon and treated with 5.40 ml of 1.06M t-butyllithium in pentane. The reaction mixture was stirred for 2.0 hours at −78°, then transferred into a stirred, −78° solution of 265 mg of copper(I)pentyne in 6.30 ml ether (solubilized at 25° with 0.725 ml of hexamethylphosphorous triamide). The resultant complex was stirred for 0.5 hour at −78°, then a solution of 480 mg of 2-(7-bromoheptyl)-2-cyclopenten-1-one (2.70 mmol) in 5.0 ml of ether was added whereupon the reaction mixture was stirred for 15 minutes at −78°, 1.5 hours at −10°, 0.75 hour at 0° and 0.5 hour at 25°. The reaction was quenched by the addition of 20% aqueous ammonium sulfate and extracted with ether at which point the ether extracts were washed with 2% V/V sulfuric acid-water, saturated aqueous NaHCO₃ and brine. The ether solution was dried (MgSO₄), filtered and evaporated in vacuo to yield 686 mg of a crude mixture of 1-Bromo-15R-(1-ethoxyethoxy)-16-methyl-18,19,20-trisnorprost-13E-en-9-one and 1-Bromo-15R-(1-ethoxyethoxy)-16-methyl-18,19,20-trisnor-8,12-diiso-prost-13E-en-9-one as a yellow oil.

Ethyl mercaptan (0.41 ml) was injected dropwise into an ice-cooled slurry of 257 mg of sodium hydride (50% in oil) in 4.0 ml dry THF. The resultant slurry was stirred for 1 hour at 25° whereupon a solution of 686 mg of the crude product named above in 4.0 ml of THF was injected. The reaction mixture was stirred for 3.0 hours at 25°, then quenched and processed as described in Example XXIX and protected as in Example XXX to afford 91.0 mg of a yellow oil having the following structure:

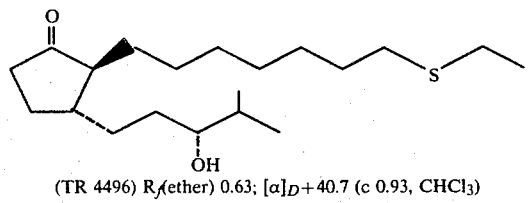

(TR 4496) R_f(ether) 0.63; [α]_D+40.7 (c 0.93, CHCl₃)

and 98.2 of a yellow oil having the structure:

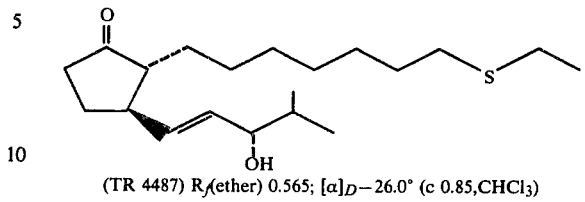

(TR 4487) R_f(ether) 0.565; [α]_D−26.0° (c 0.85,CHCl₃)

The structure of these products was confirmed by nuclear magnetic resonance, mass spectral and infrared analysis.

Analysis TR 4496 -
NMR(CDCl₃): δ0.91(pair of d, 6, i-propyl-CH₃), 2.56(m, 4, CH₂SCH₂), 1.25(t, 3, CH₂CH₃), 3.92(m, 1, CHOH), 5.70(m, 2, trans-olefinic-H)
IR(CHCl₃): 2.78, 2.90(broad), 5.75, 10.40µ Mass Spectrum: m/e 340(M+)(weak), 322(M+-H₂O), 297(M+-C₃H₇).

Analysis TR 4487 -
NMR(CDCl₃): δ0.92(pair of d, 6, i-propyl-CH₃), 2.60(m, 4, CH₂SCH₂), 3.91(m, 1, CHOH), 1.26(t, 3, J=6 Hz, 3, CH₂CH₃), 5.67(m, 2, trans-olefinic-H)
IR(CHCl₃): 2.78, 2.90(broad), 5.75, 10.40µ Mass Spectrum: m/e 340(M+), 322(M+-H₂O), 297(M+-C₃H₇).

EXAMPLE XXXVI

Preparation of
dl-1-(Isopropylsulfoxy)-16,20-methanoprost-13E-en-9-one.

Isopropyl mercaptan (0.12 ml, 63 mmol) was injected dropwise into a slurry of 1.0 ml THF and 62.5 mg of sodium hydride (50% in oil). The reaction mixture was stirred for 1 hour at 25% whereupon a solution of 167 mg of 1-Bromo-16,20-methanoprost-13E-en-9-one in 1.0 ml THF was injected. The reaction mixture was stirred for 3 hours at 25° and then processed as described in Example XXXIV to yield, after chromatography, 52.0 mg of dl-1-Isopropylthio-16,20-methanoprost-13E-en-9-one as a clear oil, mass spectrum m/e 378(M+), 360(M+-H₂O), 335 (M+-C₃H₇).

A solution of this oil in 1.0 ml of methanol was added dropwise to a stirred, chilled solution of 28 mg of sodium meta-periodate in 0.35 ml of water whereupon the reaction mixture was stirred for 3.0 hours. The reaction mixture was processed as described for the preparation in Example XXXII to afford 24 mg of a clear oil having the following composition:

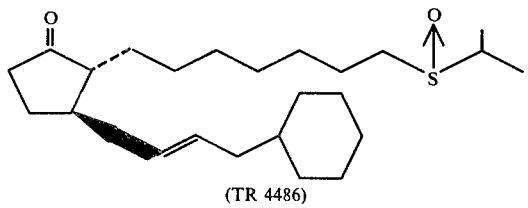

(TR 4486)

The structure of this material was confirmed by nuclear magnetic resonance, mass spectral and infrared analysis.

Analysis-NMR(CDCl₃): δ1.30(pair of d, 6, CH₃), 5.50(m, 2, =CH)

IR(CHCl₃) 5.76, 10.40μ Mass Spectrum: m/e 394(M+), 377(M+-OH), 352(M+-C₃H₆), 334.

EXAMPLE XXXVII

Preparation of 15-Depentyl-15-cyclohexyl-PGE₁-methyl ester.

A solution of 545 mg (1.61 mmol) trans-1-iodo-3R-(1-ethoxyethoxy)-3-cyclohexyl-1-propene in 10.0 ml dry ether was stirred and cooled to −78° under argon. The reaction mixture was injected with 1.74 ml of 1.85 N t-butyllithium in hexane (3.22 mmol), stirred for 2.0 hours at −78°, and added to a stirred, −78° solution of 274 mg (0.70 mmol) of tri-n-butylphosphine copper(I)iodide in 2.0 ml ether under argon. The resultant complex was stirred for 30 minutes at −78° and then treated with a solution of 227 mg (0.70 mmol) of 2-(6-carbomethoxyhexyl)-4α-tetrapyranyloxy-2-cyclopentenone in 2.0 ml of ether. The reaction mixture was stirred for 30 minutes at −78°, 1.5 hours at −20°, 0.5 hour at 0° and 15 minutes at 25°. The reaction mixture was poured into 20% aqueous ammonium chloride (adjusted to pH ~ 8.5 by addition of ammonium hydroxide), ether was added and the layers were separated. The ether layer was shaken with portions of aqueous basic ammonium chloride until the aqueous layers remained clear whereupon the combined aqueous layers were back-extracted with ether and the combined ether layers were washed with saturated aqueous sodium chloride, dried over anhydrous magnesium sulfate, filtered and evaporated in vacuo to afford 722 mg of a yellow oil. The protecting groups were cleaved by stirring the oil with 13.0 ml of 65:35 acetic acid-water and 1.3 ml dry THF for 22 hours. The reaction mixture was evaporated in vacuo whereupon the residue was dissolved in ethyl acetate, washed with saturated aqueous sodium bicarbonate and then dried (MgSO₄) and evaporated to afford 430 mg of a red oil. Chromatography of this material on 85:15 silicic acid-Celite afforded 51.3 mg of product as white oily needles having the following structure:

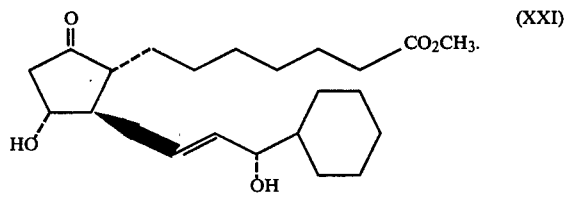

(XXI)

The structure of this material was confirmed by nuclear magnetic resonance, infrared and mass spectral analysis.

Analysis-NMR(CDCl₃): δ3.67(s, 3H, CO₂CH₃), 5.60(m, 2H, trans-olefinic-H)

IR(CHCl₃): 2.78, 2.98, 5.75, 10.40μ Mass Spectrum: $[\alpha]_D$ −44.3° (c 1.02, CHCl₃).

EXAMPLE XXXVIII

Preparation of 15-Depentyl-15-cyclohexyl-PGF₁α-methyl ester and 15-Depentyl-15-cyclohexyl-PGF₁β-methyl ester.

A solution of 109 mg of 15-depentyl-15-cyclohexyl-PGE₁-methyl ester in 10 ml methanol was cooled to 0° with stirring under argon and treated with 305 mg of sodium borohydride in 31 ml of cold methanol over 2–3 minutes. The reaction mixture was stirred for 20 minutes at 0° and for 1 hour at 25° whereupon methanol was removed in vacuo and water was added to the residue and the mixture was extracted with ether. The ether extracts were washed with saturated aqueous sodium chloride, dried over anhydrous magnesium sulfate, filtered and evaporated in vacuo to afford 62.0 mg of a yellow oil which was chromatographed on 85:15 silicic acid-Celite (elution with ethyl acetate) to afford, respectively, 15.8 mg of 15-Depentyl-15-cyclohexyl-PGF₁α-methyl ester as an oily yellow solid having the following structure:

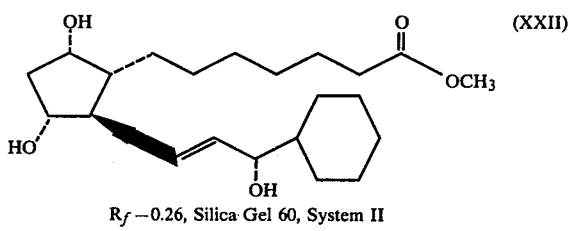

$R_f$ —0.26, Silica Gel 60, System II and, 16.0 mg of 15-Depentyl-15-cyclohexyl-PGF₁β-methyl ester as a white solid, mp 97°–98° ($R_f$=0.20) having the following structure:

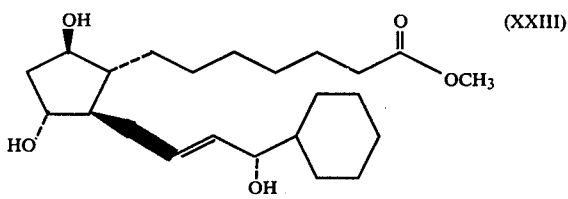

The structure of these materials was confirmed by nuclear magnetic resonance, infrared and mass spectral analysis.

Analysis-(XXII) NMR and IR identical in essential aspects to those of XXIII; $[\alpha]_D$ +15°±0.3° (c 1.58, CHCl₃) Mass Spectrum: m/e 364, 346.

Analysis-(XXIII) NMR(CDCl₃): δ3.67(s, 3H, CO₂CH₃); 5.50(m, 2H, trans-olefinic-H), 3.92(broad m, C₉-H, C₁₁-H, C₁₅-H)

IR $\lambda_{max}^{CHCl_3}$: 2.78, 2.92(broad), 5.79, 10.40μ Mass Spectrum: m/e 364(M+-H₂O), 346, 333, 315, 292, 281.

The preparation of the left-hand piece, i.e.

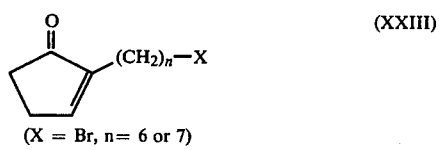

(X = Br, n= 6 or 7)

has been previously described in earlier examples. All analogues were prepared in a two-step procedure involving the reaction of XXIII with a lithiocuprate, followed by hydrolysis of the C₁₅-OH protecting group with aqueous acetic acid at 25° as described by E. J. Corey, et al. in J. Amer. Chem. Soc., 92, 397(1970). The copper-catalyzed conjugate addition of an alkenyllithium to an α,β-unsaturated ketone in the presence of an alkyl bromide was described in Example XVIII. The resultant analogue mixtures, i.e.

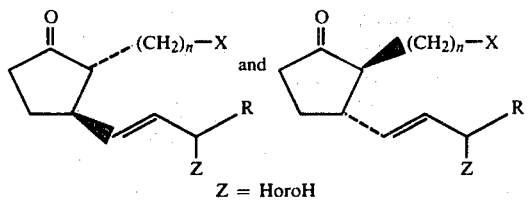

Z = HoroH were found to be moderately unstable when separation-purification was attempted on columns packed with 85:15 silicic acid-Celite, but chromatography on Silica Gel 60 was executed successfully. The reduction of the $C_1$-ketone of 11-deoxyprostaglandins with sodium borohydride is a well-known reaction, cf.: F. S. Alvarey et al., Tetrahedron Letters, 569 (1971) and references therein.

EXAMPLE XXXIX

Preparation of 1-Acetamido-11α,15R-bis(tetrahydropyran-2-yloxy)-prost-13E-en-9αβ-ol.

The following procedure was followed as described in Example LVIII. To solution 1 was added 1.68 gm (2.54 mmol) of the material prepared in Example LVII. After processing in the manner described in Example LVIII the above captioned material was obtained as an orange oil.

Analysis-NMR(CDCl$_3$): δ0.9(3H, t), 1.0–2.2936H, m), 2.0(3H, s, NHAc), 2.7(1H, m), 3.0–4.2(9H, m) 4.7(2H, m), 5.5(2H, m), 5.7(1H, m).

IR(CHCl$_3$): 3600(sharp), 3450(sharp), 3550–3250 (broad), 3000, 2930, 2850, 1660, 1520, 1465, 1450, 1440, 1375, 1260, 965 cm$^{-1}$.

EXAMPLE XXXX

Preparation of 1-Acetamido-11α,15S-bis(tetrahydropyran-2-yloxy)-prost-13E-en-9-one.

The material obtained in Example XXXIX (66 mg) was oxidized and processed as described in Example LX to yield the above-captioned material (56 mg, 84%) as a pale yellow oily solid. R$_f$(system II) 0.37.

EXAMPLE XXXXI

Preparation of 2-(7-Chloroheptyl)-2-cyclopentenone.

The following procedure was adopted from H. Hayaski et al., J. Amer. Chem. Soc., 95, 8749 (1972): To a solution containing 643 mg (3.28 mmol) of 2-(7-hydroxyheptyl)-2-cyclopentenone in 0.47 ml carbon tetrachloride at 35° (temperature of the external water bath), under argon, was added, dropwise over 1 hour, a solution containing 860 mg (3.28 mmol) triphenylphosphine in 3 ml of anhydrous methylene chloride. The yellow solution was stirred for an additional 4.0 hours at ca. 35° and overnight at reflux. The resultant brown residue was taken up in hot hexane and filtered through a sintered glass funnel containing a pad of Celite whereupon the filtrate was reduced in volume and column chromatographed using an 80% silicic acid-20% Celite column and benzene to 80% benzene-20% ethyl acetate in a gradient elution (5 ml fractions). Thus 2-(7-chloroheptyl)-2-cyclopentenone was obtained (20.2 mg) as a pale orange oil.

Analysis - NMR(CDCl$_3$): δ1.2–2.8 (16H, m), 3.46 (2.0H, t, J=6Hz), 7.45 (1.0H, bs)

IR(CHCl$_3$): 3000, 2940, 2855, 1690, 1635 and 995 cm$^{-1}$

Mass Spectrum (no parent ion): 197, 196 (p-H$_2$O), 195, 179 (base peak, p-Cl$^{35}$), 178 (p-HCl$^{35}$), 177, 161, 160, 151, 150, 137, 135, 123, 121, 109, 97, 95, 81, 79.

EXAMPLE XXXXII

Preparation of 2-(7-iodoheptyl)-2-cyclopentenone.

A solution containing 918 mg (6.0 mmol) of 1-morpholino-1-cyclopentene, 1.20 gm (5.0 mmol) of 7-iodoheptanal and 11 ml benzene, under argon, was refluxed overnight (15 hours). To the cooled solution was added 3 ml of 1:1 (V/V) hydrochloric acid-water and the mixture stirred for 1.25 hours at room temperature. The layers were separated and the aqueous layer was extracted with 1×10 ml of benzene. The combined benzene solutions were successively washed with saturated aqueous sodium bicarbonate, saturated aqueous brine and dried (MgSO$_4$). The solvent was removed by evaporation in vacuo to yield 1.1 gm of a yellow oil. The material was vacuum distilled (bulb to bulb) to yield two portions. Fraction one, 127°–140° (0.2 tor) contained 351 mg of an orange oil which was identified by its NMR spectrum as a 1:1 mixture of 2-(7-iodoheptyl)-2-cyclopentenone and 2-(anti-7-iodo-1-heptenyl)cyclopentanone. Fraction 2, 150°–160° (0.2 tor), contained 283 mg (14%) of an orange oil identified by its NMR spectrum to be 2-(7-iodoheptyl)-2-cyclopentenone. An analytical sample of this fraction was purified by preparative thin layer chromatography (F 254 silica gel, ether as eluent) to yield 140 mg of 2-(7-iodoheptyl)-2-cyclopentenone as a yellow oil.

Analysis-NMR(CDCl$_3$): δ1.1–2.8(16H, complex m), 3.1 (2H, t, J=7Hz), 7.5 (1H, bs)

IR(CHCl$_3$): 3000, 2930, 2850, 1690, 1635, 1440, 1000, 920 cm$^{-1}$; $UV\lambda_{228}^{MeOH}$ 10,290

Mass Spectrum (70 eV): m/e 306 (parent), 210, 179 (p$^+$-I$^{127}$), 161 (p$^+$-I-H$_2$O), 155, 144.89 m), 137, 135, 133, 127, 123, 121, 97 (base peak).

EXAMPLE XXXXIII

Preparation of 2-Decarboxy-2-ethylthiomethyl-15-deoxy-PGF$_{1\alpha}$.

438 mg crude XX was stirred with 24.0 ml 65:35:10 acetic acid-water-THF for 17.0 hours at 25° under argon. The solvents were evaporated and the mixture processed as described in Example XXVII to yield 121 mg of product (TR 4414) as a clear oil.

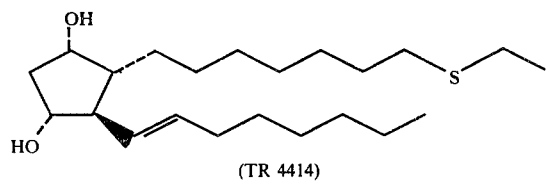

(TR 4414)

Analysis-Mass Spectrum: m/e 370 (M$^+$), 372 (M$^+$-H$_2$O), 334 (m$^+$-2H$_2$O), 323 (352-Et), 305 (323-H$_2$O)

NMR(CDCl$_3$): δ0.90 (t, 3), 3.0 (broad s, 2), 3.8–4.3 (complex, 2), 5.36 (complex, 2)

IR(CHCl$_3$): 2.78, 2.90, 7.25, 10.40μ.

EXAMPLE XXXXIV

Preparation of 1-Mecapto-16,20-methanoprost-13E-ene-9β,11α,15R-triol (TR 4615).

A solution of 480 mg XV in 7.0 ml dry acetone was stirred with 260 mg potassium carbonate and 580 mg anhydrous lithium iodide for 18.0 hours at 25°. The reaction mixture was processed as described in Example XII to yield 312 mg crude iodide as a yellow oil, R$_f$(ether) 0.69.

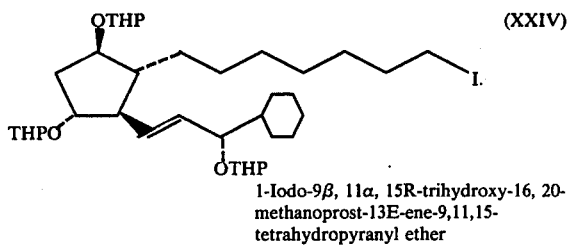

1-Iodo-9β, 11α, 15R-trihydroxy-16, 20-methanoprost-13E-ene-9,11,15-tetrahydropyranyl ether A solution of 227 mg of iodide in 1.0 ml of 95% ethanol was refluxed with 25 mg of thiourea for 45 minutes under argon. The reaction mixture was cooled and 2.2 ml of anhydrous methanol added, followed by 0.32 ml of 26% aqueous potassium hydroxide. The reaction mixture was allowed to stand for 23 hours at 25°. The reaction mixture was poured into water and acidified with 6 N hydrochloric acid. The aqueous layer was extracted with ether. The ether was shaken with saturated aqueous sodium bicarbonate and brine, then dried (MgSO$_4$), filtered and evaporated in vacuo to yield 121 mg of a yellow oil. The crude product was purified by column chromatography to afford 28 mg of TR 4615 as a white oily solid having the following structural formula:

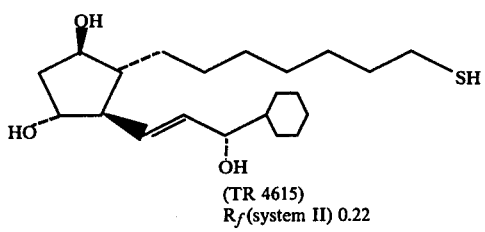

(TR 4615)
R$_f$(system II) 0.22

Analysis-Mass Spectrum: m/e 370 (M+), 352 (M+-H$_2$O), 335 (M+-2H$_2$)

NMR(CDCl$_2$): δ2.5–3.3 (6, OH, CH$_2$SH), 3.6–4.4 (m 3, CHOH), 5.60 (m, 2, =CH)

IR (CHCl$_3$): 2.78, 2.94 (broad), 6.90, 9.7, 9.8, 10.4μ.

The following examples are directed to the preparation of amino analogues of certain prostaglandins.

EXAMPLE XXXXV

Preparation of 2-(anti-7-morpholinoheptylidene)cyclopentanone.

A solution containing 2.16 gm (14.1 mmol) of 1-morpholinocyclopentene and 3.08 gm (17.8 mmol) of 7-iodoheptanal in 25 ml anhydrous benzene were heated at reflux under argon for 39 hours. The resulting red solution containing a black precipitate was evaporated to near dryness (rotoevaporator). The residue was dissolved in 7.01 ml dimethyl formamide (DMF-anhydrous-stored over molecular sieve 4A followed by storing over alumina activity I).

This solution was added, over a half hour period, to a mixture containing 1.82 gm (13.2 mmol) potassium carbonate, 4.4 gm (50.0 mmol) morpholine and 14 ml anhydrous DMF at 50° under argon. The viscous mixture was stirred for an additional 0.75 hour at 50° and then cooled to room temperature. Water (50 ml) was added and the solution extracted 3×50 ml 5:1 (V/V) ethel ether-hexane. The combined organic phases were washed with 20 ml water and reduced in volume (rotoevaporator). To the red oily residue was added 20 ml benzene followed by 10 ml of a 1:1 (V/V) hydrochloric acid-water solution. The mixture was stirred at room temperature for 1.25 hours whereupon the layers were separated and the benzene layer was back-washed with an equal volume of water. The organic layer was rejected and the combined aqueous layers were diluted with ether and basified (pH 9) with 1.25 M aqueous sodium hydroxide. The layers were separated and the aqueous layer back-extracted two times with 1:1 (V/V) ether-ethyl acetate. The combined organic layers were washed with saturated aqueous brine solution and dried (MgSO$_4$). The filtrate was evaporated in vacuo to yield 2.66 gm of a dark orange oil. This oil was column chromatographed on base washed (ammonium hydroxide) silica gel 60, using ethyl acetate as eluant to yield 1.09 gm (35%) of 2-(anti-7-morpholinoheptylidene)cyclopentanone as an orange oil.

Analytical Data-NMR (CDCl$_3$): δ1.2–3.0 (22H, complex m), 3.8 (4H, t, J=6Hz), 6.6 (1H, bt, J=7Hz)

IR (CHCl$_3$): 3000, 2935, 2850, 2805, 1710, 1640, 1450, 1110, 860 cm$^{-1}$; UVλ$_{240}$ mm$^{isoctane}$ (ε 8.50)

Mass Spectrum (70 e/v): m/e 265 (parent.), 237, 220, 209, 208, 182.

EXAMPLE XXXXVI

Preparation of 2-(anti-7-morpholinoheptylidene)cyclopentanone N-oxide.

To a solution containing 3.0 gm (11.3 mmol) 2-(anti-7-morpholinoheptylidine)cyclopentanone in 10 ml of chloroform was added, under argon at 0°, a solution containing 85% meta-chloroperbenzoic acid 2.25 gm, (13.0 mmol) in 20 ml chloroform over a 15 minute period. After addition the solution was stirred for 1.25 hours at 0° whereupon it was quenched with the addition of 10% aqueous sodium bisulfite solution. The organic layer was separated and the aqueous layer back-extracted two times with equal volumes of chloroform. The combined organic layers were washed with saturated aqueous sodium bicarbonate (two times) and dried (MgSO$_4$). The chloroform solution was evaporated in vacuo to yield 4.1 gm of a viscous red-orange oil. This material was column chromatographed (silica gel) using ethyl acetate to 80% ethyl acetate-20% methanol (V/V) gradient elution. In this manner 302 mg of 2-(anti-7-morpholinoheptylidene)cyclopentanone N-oxide was obtained as an orange oil.

Analysis-NMR (CDCl$_3$): δ1.1–2.9 (16H, complex m), 3.2 (4H, m), 3.8 (2H, bd, J=11, 4Hz), 4.5 (4H, ttt, J=11, 7, 4Hz), 6.7 (1H, m)

IR (CHCl$_3$): 3000, 2935, 2850, 1715, 1640, 1460, 1100, 900, 860 cm$^{-1}$.

EXAMPLE XXXXVII

Preparation of
2-(7-morpholinoheptyl)-2-cyclopenten-1-one.

To 12.3 gm (46.4 mmol) of 2-(anti-7-morpholinoheptylidene)cyclopentanone as prepared in Example XXXXVI in 45 ml n-butanol was added 4.5 ml (12 M) hydrochloric acid and the solution heated at reflux, under argon, for 2.5 hours. The soluton was allowed to cool to room temperature, diluted with ether and carefully basified (to pH 8) with saturated aqueous sodium bicarbonate. The aqueous layer was back extracted (2X) with ether and the combined organic layers were washed with saturated aqueous brine and dried (MgSO$_4$).

After evaporation of solvents in vacuo the crude product (9.2 gm of a red-orange oil) was dry column chromatographed on silica gel-60 using a gradient of ethyl acetate to 8:2 (V/V) ethyl acetate-methanol as eluant. In this manner 6.86 gm of almost pure product was obtained. This material was vacuum distilled (bp 141°–143°, 0.2 tor) to yield 2.85 gm (23%) of the desired product.

Analysis-NMR (CDCl$_3$): δ1.2–2.0 (10H, m), ca. 2.5 (12H, bt), 3.8 (4H, t), 7.45 (1H, m)

IR (CHCl$_3$): 3000, 2925, 2860, 2810, 1695, 1623, 1460, 1360, 1115, 1000, 855 cm$^{-1}$

Mass Spectrum: 265 (p$^+$), 249, 234 (p$^+$-CH$_2$OH, 220 (p$^+$-C$_2$H$_4$OH), 198, 185, 184, 171, 170, 156, 149 (p$^+$-C$_5$H$_{14}$NO), 129, 126, 114, 112 and others below 100; U.V. λ$_{220\ mm}$$^{isooctane}$ (ε10,600), R$_f$ (1:1 ethyl acetate-methanol V/V) 0.48.

EXAMPLE XXXXVIII

Preparation of
1-hydroxy-16,20-methano-11α,15R-bis(tetrahydropyran-2-yloxy)prost-13E-en-9-one To 3.54 gm of 1-iodo-3-cyclohexyl-3R-(tetrahydropyran-2-yloxy)-1E-propene in 27 ml anhydrous ether, at −78°, under argon, was added dropwise 14.0 ml of 1.44 M t-butyllithium (alpha in n-pentane). The resultant solution was stirred for 2.0 hours at −78°. To a dispersion of 1.31 gm cuprous 1-pentyne in 50 ml anhydrous ether at room temperature under argon was added 2.9 ml of hexamethylphosphrous triamide. The resultant solution was transferred via syringe to the alkenyl lithium solution.

After stirring for 10 minutes at −78° a solution of 2.86 gm of methyl 7[4R-(tetrahydropyran-2-yloxy)-5-oxocyclopent-1-enyl]heptanoate in 8 ml anhydrous toluene was added dropwise via syringe. The resultant orange dispersion was stirred for 15 minutes at −78° and gradually warmed to −20° over a 2 hour period. The reaction mixture was then quenched at −78° with 4.8 ml anhydrous acetic ahydride. The mixture was stirred at −78° for 5 minutes, and the mixture poured onto a mixture of 20% ammonium chloride (pH 8 by addition of ammonium hydroxide) and crushed ice. The layers were separated and the organic layer successively washed with 10% aqueous sodium bicarbonate (two times), water, saturated aqueous brine and dried (anhydrous K$_2$CO$_3$). After evaporation of solvents, in vacuo, its orange oily residue was dissolved in 40 ml anhydrous THF and cooled to −78°. To this solution was added, dropwise, 18 ml of a 20% benzene solution of red-Al over a 20 minute period. The solution was then warmed to −10° over a 1.0 hour period and stirred for an additional 1.0 hour at −10°. The reaction mixture was quenched by transferring, via a ¼" O.D. polyethylene tube, under positive nitrogen pressure, into a large beaker containing a stirred mixture of wet ice and 20% aqueous ammonium chloride solution. The mixture was diluted with 50% ether-ethyl acetate and the layers separated. (Note: vacuum filtration-sintered glass funnel, pad of Celite-may be necessary at this point to remove aluminum salts). The aqueous layer was back-extracted (2X) with the ether-ethyl acetate mixture and the combined organic layers were successively washed with 2% aqueous sulfuric acid, saturated aqueous sodium bicarbonate, saturated aqueous brine and dried (MgSO$_4$). After evaporation of solvents, in vacuo, 3.60 gm (90%) of crude 1-hydroxy-16,20-methano-11α,15R-bis(tetrahydropyran-2-yloxy)prost-13E-en-9-one was obtained as an orange oil. This material was used in subsequent reactions.

Analysis-NMR (CDCl$_3$): δ1.1–2.9 (40 H, m) 3.4–4.2 (10H, m)

4.8 (2H, bs), 5.75 (2H, m); R$_f$(ether) 0.41.

EXAMPLE XXXXIX

Preparation of
1-hydroxy-11α,15S-bis(tetrahydropyran-2-yloxy)prost-13E-en-9-one.

Repeating in a similar manner the procedures of Example XXXXVIII, but replacing 1-iodo-3-cyclohexyl-3R-(tetrahydropyran-2-yloxy)-1E-propane with 1-iodo-3S-(tetrahydropyran-2-yloxy)-1E-octene yields 1-hydroxy-11α,15S-bis(tetrahydropyran-2-yloxy)prost-13E-en-9-one.

Analysis-NMR (CDCl$_3$): δ0.9 (3H, t, J=6 Hz), 1.2–2.3 (32H, m), 2.3–2.9 (4H, m) 3.4–4.3 (6H, m), 4.8 (2H, m)

IR (CHCl$_3$): 3600(sharp), 3350(broad), 2925, 1730, 1460, 1120, 1065, 1010, 965 cm$^{-1}$; R$_f$(system II) 0.70.

EXAMPLE L

Preparation of
16,16-dimethyl-1-hydroxy-11α,15RS-bis(tetrahydropyran-2-yloxy)prost-13E-en-9-one.

Repeating in a similar manner the procedures of example XXXXIX, but replacing 1-iodo-3-cyclohexyl-3S-(tetrahydropyran-2-yloxy)-1E-propene with 1-iodo-4,4-dimethyl-3RS-(tetrahydropyran-2-yloxy)-1E-octene yields 16,16-dimethyl-1-hydroxy-11α,15RS-bis(tetrahydropyran-2-yloxy)prost-13E-en-9-one.

Analysis-NMR (CDCl$_3$): δ0.9 (9H, bs), 1.0–3.0 (35H, m), 3.4–4.2 (6H, m), 4.65 (2H, bs), 5.7 (2H, m); R$_f$(ether) 0.42.

EXAMPLE LI

Preparation of
1-Methanesulfonyoxy-11α,15R-bis(tetrahydropyran-2-yl-oxy)prost-13E-en-9-one.

To 2.026 gm (3.90 mmol) of the material prepared in Example XXXXVIII in 8 ml of anhydrous tetrahydrofuran (THF) at 0°, under argon, was injected 0.84 ml triethylamine followed by dropwise addition of 0.42 ml freshly distilled methanesulfonylchloride. The reaction mixture was stirred for 40 minutes at 0°, diluted with ether and filtered. The filtrate was washed with 2% aqueous sulfuric acid, 10% aqueous sodium bicarbonate and dried (Na$_2$SO$_4$). The aqueous layers were back-extracted (2X) with ether and the combined organic layers evaporated in vacuo to yield 2.067 gm (89%) of the desired product as a yellow oil.

Analysis-NMR (CDCl$_3$): δ1.0–2.3 (37H, m), 2.6 (2H, t), 3.0 (3H, s), 3.3–4.0 (6H, m), 4.1 (2H, m), 4.8 (2H, m), 5.5 (2H, m); R$_f$ (95:5, chloroform-acetone) 0.30; R$_f$ (ether) 0.34.

EXAMPLE LII

1-Methanesulfonyloxy-11α,15S-bis(tetrahydropyran-2-yloxy)prost-13E-en-9-one.

In a similar manner as described in Example LI, the material prepared in Example XXXXIX (1.70 gm) was converted to the desired product (2.05 gm, 99%) as a yellow oil.

Analysis-NMR (CDCl$_3$): δ0.9 (3H, t), 1.1–2.5 (34H, m), 2.7 (2H, t), 3.1 (3H, s), 3.3–4.0 (6H, m), 4.3 (2H, m), 4.8 (2H, m), 5.7 (2H, m)

IR (CHCl$_3$): 3000, 2935, 2850, 1730, 1460, 1370, 1350, 1330, 1245, 1165, 1125, 1070, 1025, 965 cm$^{-1}$; R$_f$ (8:2 V/V chloroform-acetone) 0.85, R$_f$(ether) 0.43.

EXAMPLE LIII

1-Methanesulfonyloxy-16,16-dimethyl-11α,15RS-bis(-tetrahydropyran-2-yloxy)-prost-13E-en-9-one.

In a manner similar to that described in Example LII the material prepared in Example L (227 mg) was converted to the desired product as a pale orange oil.

Analysis - NMR (CDCl$_3$): δ0.9 (9H, bs), 1.1–2.3 (34H, m), 2.6 (2H, t), 3.1 (3H, s), 3.3–4.0 (6H, m), 4.3 (4H, dd), 4.8 (2H, m), 5.7 (2H, m)

IR (CHCl$_3$): 3000, 2935, 2950, 1730, 1600, 1470, 1450, 1440, 1380, 1360, 1340, 1260, 1170, 1130, 1110, 1070, 1025, 965 cm$^{-1}$; R$_f$ (9:1 (V/V) chloroform-acetone) 0.75.

EXAMPLE LIV

Preparation of 16,20-methano-1-methanesulfonyloxy-11α,15R-bis(tetrahydropyran-2-yloxy)-prost-13E-en-9-ol.

To 2.06 gm of the material prepared in Example LI in 8.0 ml of absolute ethanol at −10°, under argon, was added proportionwise 190 mg of sodium borohydride. The reaction was stirred at −10° for 0.5 hour and then quenched with 0.4 ml water. The mixture was reduced in volume (rotoevaporator) and diluted with ether and water. The ether layer was separated, washed with saturated aqueous brine and dried (Na$_2$SO$_4$). The aqueous layers were back-extracted with ether-ethyl acetate (1:1 v/v) and the combined organic extracts evaporated in vacuo to yield 1.80 gm (77%) of the desired product as a pale yellow oil.

Analysis-NMR (CDCl$_3$): δ1.0–2.5 (39H, m), 2.8 (1H, bs), 3.0 (3H, s), 3.3–4.0 (9H, m), 4.2 (3H, m), 4.7 (2H, m), 5.5 (2H, m)

IR (CHCl$_3$): 3600 (sharp), 3550–3300 (broad), 3000, 2920, 2845, 1465, 1450, 1350, 1330, 1165, 1070, 1020, 965 cm$^{-1}$, R$_f$(ether) 0.27 and 0.18.

EXAMPLE LV

Preparation of 1-methanesulfonyloxy-11α,15S-bis(tetrahydropyran-2-yloxy)prost-13E-en-9-ol and 1-Methanesulfonyloxy-16,16-dimethyl-11α,15RS-bis(-tetrahydropyran-2-yloxy)-prost-13E-en-9-ol.

In a similar manner as that previously described in Example LIV, the above-captioned compounds were synthetized from those prepared in Examples LII and LIII respectively.

Analysis-NMR(CDCl$_3$): δ0.9 (3H, t), 1.1–2.2 (37H, m), 3.1 (3H, s), 3.4–4.4 (9H, m), 4.8 (2H, m), 5.6 (2H, m)

IR(CHCl$_3$): 3600 (sharp), 3575–3300 (broad), 3000, 2930, 2850, 1470, 1450, 1440, 1375, 1355, 1335, 1240, 1170, 1120, 1070, 1030, 1015, 965 cm$^{-1}$; R$_f$(ether) 0.31 and 0.20.

Analysis-(16,16-dimethyl analogue) NMR: δ0.9 (9H, bs), 1.1–2.2 (3.4H, m), 2.8 (1H, bs), 3.1 (3H, s), 3.5–4.5 (9H, m), 4.8 (2H, m), 5.5 (2H, m), R$_f$(9:1 chloroform-acetone), 0.51 and 0.36.

EXAMPLE LVI

Preparation of 9αβ-(1-ethoxyethoxy)-16,20-methano-1-methanesulfonyoxy-11α,15S-bis(tetrahydropyran-2-yloxy)prost-13E-ene.

To 1.80 g of 16,20-methano-1-methanesulfonyloxy-11α,15R-bis(tetrahydropyran-2-yloxy)prost-13E-en-9-ol was added 8 ml anhydrous ether, 0.45 ml ethylvinyl ether and 10 mg of p-toluenesulfonic acid monohydrate. The solution was stirred under argon, at ambient temperature for 2.0 hours. To the red-orange solution was added ca. 30 mg of solid sodium bicarbonate and the contents of the flask reduced in volume (rotoevaporator). The residue was diluted with ether and 10% aqueous sodium bicarbonate and the layers separated. The aqueous layer was back-extracted (2X) with ether and the combined ethereal extracts were washed with saturated aqueous brine and dried (Na$_2$SO$_4$). After evaporation of solvents (in vacuo) 1.73 g of the desired product as a maroon viscous oil was obtained. R$_f$(ether) 0.43.

EXAMPLE LVII

Preparation of 9αβ-(1-ethoxyethoxy)-1-methanesulfonyloxy-11α,15S-bis(tetrahydropyran-2-yloxy)prost-13E-ene.

In a manner similar to that previously described for the preparation in Example LVI, the above-captioned material was prepared as an orange viscous oil (R$_f$[ether] 0.59) from 1-methanesulfonyloxy-11α,15S-bis(tetrahydropyran-2-yloxy)prost-13E-en-9-ol as prepared in Example LV.

EXAMPLE LVIII

Preparation of b 1-Acetamido-9αβ-(1-ethoxyethoxy)-16,20-11α,15R-bis(tetrahydropyran-2-yloxy)prost-13E-ene [A] and 1-acetamido-16,20-methano-11α,15R-bis(tetrahydropyran-2-yloxy)prost-13E-en-9-ol [B].

To 780 mg (3.35 mmol) bis-benzenesulfenimide (T. Mukaiyama, et al., Tetrahedron Letters, 3411 [1970]) in 6 ml of anhydrous tetrahydrofuran (THF) at −20°, under argon, was injected dropwise, sec-butyllithium in cyclohexane (1.39 M, 2.4 ml, 3.35 mmol). The solution was stirred for 15 minutes at −20° (solution 1).

To the above solution 1 was added, over a 5 minute period, a solution containing 1.73 gm (2.58 mmol) of the material prepared in Example LVI. The red-black solution was stirred at −20° for 2.0 hours, gradually warmed to ambient temperature over a 0.5 hour period and stirred overnight at ambient temperature. To this solution was injected 0.39 ml of thiophenol and the reaction stirred for 0.5 hours at ambient temperature.

The solution was cooled at 0° and 0.47 ml of absolute ethanol was added, followed, 5 minutes later, by the injection, very fast dropwise, of 1.0 ml acetic anhydride. The red-black solution was stirred at room temperature for 7 minutes diluted with ether and the contents of the flask poured into a slurry of cracked ice and 10% aqueous sodium bicarbonate. The layers were separated and the organic layer washed with 10% aqueous potassium hydroxide, water, saturated aqueous brine and dried (MgSO$_4$). The aqueous solutions were back-extracted (3x) with ether. The combined ethereal extracts were evaporated in vacuo to yield 1.473 of a red-orange oil.

This material was purified by column chromatography (silica gel 60, benzene to ethyl acetate and then ethyl acetate to 96:4 (V/V) ethyl acetate-methanol). In this manner 75 mg of 1-acetamido-9α$\beta$-(1-ethoxyethoxy)-16,20-methano-11α,15S-bis(tetrahydropyran-2-yloxy)prost-13E-ene [A] as an orange oil and 110 mg of 1-acetamido-16,20-methano-11α,15R-bis(tetrahydropyran-2-yloxy)prost-13E-en-9-ol [B] as an orange oil was obtained.

Analysis [A]-NMR(CDCl$_3$): δ0.9–2.2(44H, m), 2.0(3H, s, NHAc), 3.2–4.2(12H, m), 4.7(3H, m), 5.5(3H, m, trans-vinyl+NHAc)

IR(CHCl$_3$): 3450(sharp), 2995, 2925, 2850, 1660, 1520, 1450, 1360, 1255, 1130, 1070, 1015, 965, 900, 860 cm$^{-1}$ Mass Spectrum: no 636(p$^+$), 606(p$^+$-C$_2$H$_6$), 593(p$^+$-Ac), 577(p$^+$-NHAc), 565(p$^+$-C$_4$H$_7$O), 553(p$^+$-C$_6$H$_{11}$), 551.5(p$^+$-C$_2$H$_6$), 523.5, 509, 495.5, 480, 466.5, 461, 451.5, 368, 305, 227, 185, 85, 83, 69, 67, 57, 55(base peak), R$_f$(system II) 0.38 and 0.32.

Analysis [B] - NMR (CDCl$_3$): δ0.9–2.2(39H, m), 2.0(3H, s, NHAc), 3.0–4.1(10H, m), 4.7(2H, m), 5.5(2H, m), 5.85(1H, m)

IR(CHCl$_3$): 360(sharp), 3450(sharp), 3550–3200(broad), 2995, 2930, 2850, 1660, 1520, 1450, 1370, 1260, 1130, 1100, 1070, 1020, 970, 900, 860 cm$^{-1}$ Mass Spectrum: no 563.9(p$^+$), 509, 491(p$^+$-CH$_2$NHAc), 478(p$^+$-C$_5$H$_{10}$O), 461(p$^+$-HOTHP), 396, 394, 389(p$^+$-HOTHPCH$_2$NHAc), 360(p$^+$-2HOTHP), 342(p$^+$-2HOTHP-2H$_2$O), 341, 312(p$^+$-C$_6$H$_{11}$), 306, 305(base peak, p$^+$-[CH$_2$]$_7$N$^+$H$_2$Ac-HOTHP), 304, 394, 276, 227(second base peak, p$^+$-C$_{13}$H$_{25}$N), 212, 121, 114, 95, 85, (third base peak, THP), 83, 73, 67, 57, 55(fourth base peak, C$_3$H$_3$O); R$_f$(system II) 0.25 and 0.21.

EXAMPLE LIX

1-Acetamido-16,20-methano-11α,15S-bis(tetrahydropyran-2-yloxy)prost-13E-en-9α$\beta$-ol.

To 75 mg of the [A] material prepared in Example LVIII was added 1 ml 65:35:10 (V/V) acetic acid-water-THF and the solution was stirred at ambient temperature for 3.4 hours. The reaction mixture was reduced in volume (rotoevaporator) and diluted with ether and 10% aqueous sodium bicarbonate. The ether layer was washed with saturated aqueous brine and dried (MgSO$_4$). The aqueous layers were back-extracted with 1:1 (V/V) ether-ethyl acetate (2x) and the combined organic extract evaporated in vacuo to yield 58 gm of an orange oil. The TLC of this material indicated a mixture of starting material, desired product and over-hydrolyzed product to be present. This material was column chromatographed (silica gel 60, chloroform to 1:1 chloroform-acetone) to yield 34 mg of starting material, 7 mg of the desired product as a colorless oil and 5 mg of mono-protected (i.e. THP at C-11 or C-15, most likely the former) product.

EXAMPLE LX

Preparation of 1-Acetamido-16,20-methano-11α,15R-bis(tetrahydropyran-2yloxy)prost-13E-en-9-one.

Collins Reagent 0.34 M: To 17.0 ml of anhydrous methylene chloride (collected after elution through a column of Brockmann Activity I, basic Alumina) and 1.02 ml anhydrous pyridine, magnetically stirred, under argon, was added, at room temperature, 622 mg anhydrous chromium trioxide (dried overnight at 60° C., in vacuo, in an Abderhalden drying pistle, using phosphorous pentoxide as desicant). The deep burgandy solution was stirred at room temperature for 15 minutes prior to use.

To an oven (105°) dried flask at room temperature, under argon, was added 440 mg dry Celite (a diatomaceous earth; oven dried at 105° for at least 1.0 hour). To this stirred slurry at 0° was injected 2.7 ml of 0.34 M Collins Reagent followed by injection of 83 mg of 1-acetamido-16,20-methano-11α,15R-bis(tetrahydropyran-2-yloxy)prost-13E-en-9-ol prepared in Examples LVIII and LIX in 0.2 ml anhydrous methylene chloride. After 0.5 hour the reaction was quenched with 440 mg sodium hydrogen sulfate dihydrate and the mixture stirred for an additional 10 minutes. The mixture was suction filtered through a sintered glass funnel and the filter cake washed with several portions of ethyl ether. The filtrate was washed with 2% aqueous sulfuric acid, 10% aqueous sodium bicarbonate and dried (MgSO$_4$). After filtration and evaporation of solvents in vacuo 65.7 mg (79%) of the crude product was obtained as a yellow oily solid. R$_f$(system II) 0.35.

EXAMPLE LXI

Preparation of 1-Acetamido-11α,15R-dihydroxy-16,20-methanoprost-13E-en-9-one (TR 4798).

To 80 mg of the crude material prepared in Example LX was added 3.0 ml of 65:35:10 (V/V) acetic acid-water-tetrahydrofuran and the solution stirred at room temperature under argon for 24 hours. After removal of solvents in vacuo, the residue was diluted with 1:1 (V/V) ethyl acetate-ethyl ether and 5% aqueous sodium bicarbonate. The organic extracts were washed with saturated aqueous brine and dried (MgSO$_4$). After evaporation of solvents in vacuo, 63 mg of an orange oily solid was obtained.

Chromatography (silica gel 60) using as eluant 1:1 (V/V) benzene-ethyl acetate to ethyl acetate followed by 500 ml 95:5 (V/V) ethyl acetate-methanol, yielded 12.8 mg of impure product which was repurified by preparative TLC (silica gel PF-254, utilizing 9:1:0.01 [V/V] chloroform-methanol-ammonium hydroxide) to yield 3.6 mg of desired product as an orange solid.

Analysis - NMR(CDCl$_3$): δ1.0–1.99(20H, m), 2.0(3H, s), 2.1–2.9(9H, m), 3.2(2H, bt), 4.0(2H, m), 5.6(2H, m), 5.9(1H, m, NHAc)

IR(CHCl$_3$): 3600(sharp), 3560–3200(broad), 3000, 2930, 2900, 1735, 1660, 1515, 1450, 1365, 1075, 970 cm$^{-1}$; [α]$_D$−45.1° (c 0.37, CHCl$_3$); R$_f$(system II) 0.065

Mass Spectrum (70 eV): no 392.5(p$^+$), 375(p$^+$-H$_2$O), 357(p$^+$-H$_2$O), 310(p$^+$-C$_6$H$_{11}$-c), 292(base peak, p$^+$-C$_6$H$_{11}$-c-H$_2$O), 250, 156, 97, 95, 85, 83, 57, 55.

EXAMPLE LXII

Preparation of
1-Acetamido-11α,15S-dihydroxyprost-13E-en-9-one (TR 4760) and
1-Acetamido-15S-hydroxyprosta-10,13E-dien-9-one (TR 4761).

In a manner similar to that previously described in Example LXI, 112.8 mg of 1-Acetamido-11α,15S-bis(-tetrahydropyran-2-yloxy)prost-13E-en-9-one as prepared in Example XXXX, supra, was hydrolyzed and purified by column chromatography to yield 22.2 mg of TR 4760 as a yellow oily solid and 4.3 mg of TR 4761 (a side product of the acid hydrolysis) as a pale yellow oil.

Analysis (TR 4761) - NMR(CDCl$_3$): δ0.9(3H, t), 1.0–1.9(20H, m), 2.0(3H, s), 2.1–2.8(4H, m), 3.2(2H, bt), 3.7(2H, bs, D$_2$O exchangeable), 4.1(2H, m), 5.6(2H, m), 5.8(1H, m)

IR(CHCl$_3$): 3600(sharp), 3550–3100, 3445(sharp), 3000, 2945, 2855, 1735, 1660, 1525, 1510, 1460, 1435, 1365, 1070, 965 cm$^{-1}$ Mass Spectrum (70 eV): no 381(p$^+$), 363(p$^+$-H$_2$O), 345(p$^+$2H$_2$O), 292(base peak, p$^+$-C$_5$H$_{11}$-H$_2$O), 264, 250, 222, 156, 107, 95, 91, 81, 79, 73, 72, 67, 60, 55; [α]$_D$-51.6° (c 0.77, CHCl$_3$); R$_f$(system II) 0.10.

Analysis (TR 4760) - NMR(CDCl$_3$): δ0.9(3H, bt), 1.1–2.3(24H, m), 2.0(3H, s), 3.2(2H, bt), 4.05(1H, m), 5.6(2H, m), 6.2(1H, d), 7.5(1H, dd)

IR(CHCl$_3$): 3600(sharp), 3540-3200(broad), 3450 (sharp), 3000, 2935, 2850, 1700, 1660, 1595, 1915, 1460, 1440, 1370, 1100, 1070, 965 cm$^{-1}$ Mass Spectrum: 365(p$^+$), 345(p$^+$-H$_2$O), 294, 292(p$^+$-C$_5$H$_{11}$n), 265, 264, 263, 250, 222, 156, 149, 121, 101, 95, 93, 91, 85(base peak, C$_4$H$_7$NO), 81, 79, 69, 67, 57, 55; [α]$_D$ 59.7 (c 0.33, CHCl$_3$); R$_f$(system II) 0.20.

EXAMPLE LXIII

1-Acetamido-prost-13E-ene-9αβ,11α,15S-triol (TR 4762).

To 77 mg of crude 1-Acetamido-11α,15S-bis(tetrahydro-2-yloxy)prost-13E-en-9αβ-ol from Example XXXIX was added 2 ml of 65:35:10 (V/V) acetic acid-water-tetrahydrofuran and stirred overnight at room temperature. After the workup and purification steps as previously described in Example XLI, 12.4 mg of the desired product was obtained as a yellow oil.

Analysis - NMR(CDCl$_3$): δ0.9(3H, bt), 1.1–2.3(24H, m), 2.0(3H, s), 3.0(3H, m, D$_2$O exchangeable), 3.2(2H, bt), 4.1(3H, m), 5.5(2H, m), 5.75(1H, m)

IR(CHCl$_3$): 3600(sharp), 3550-3040(broad), 3440 (sharp), 3000, 2935, 2850, 1660, 1515, 1460, 1430, 1080, 965 cm$^{-1}$ Mass Spectrum (70 eV): 366(p$^+$-OH), 365(p$^+$-H$_2$O), 347(p$^+$-2H$_2$O), 329(p$^+$-3H$_2$O), 312(p$^+$-C$_5$H$_{11}$), 294(p$^+$-H$_2$O-C$_5$H$_{11}$), 293, 276(p$^+$-2H$_2$O-C$_5$H$_{11}$), 258, 235, 234(base peak, p$^+$-C$_5$H$_{11}$-2H$_2$O-C$_2$H$_2$O), 216, 199, 196, 189, 156, 135 and others below 121; R$_f$(1:1 [V/V] chloroform-acetone) 0.04.

EXAMPLE LXIV

Preparation of
1,9β,11α,15R-Tetra-tetrahydropyran-2-yloxy-16-methyl-18,19,20-trisnorprost-13E-ene.

A solution of 608 mg of 16-Methyl-18,19,20-trisnor-PGF$_{1β}$ methyl ester 9,11,15-tris-tetrahydropyranyl ether (from reduction of the 9-keto group of 16-methyl-18,19,20-trisnor-11,15-bis-tetrahydropyranyloxy-PGE$_1$ methyl ester with sodium borohydride in methanol, followed by separation of the 9α- and 9β-isomers by column chromatography and protection of the 9β-hydroxy group as the tetrahydropyranyl ether) in 4.2 ml of dry tetrahydrofuran (THF) was added dropwise to 1.25 ml of Red-Al (70% in benzene) in 1.8 ml of dry THF at −10° C. under argon. The reaction mixture was stirred for 2.75 hours at 0° and for 0.25 hour at 25°, then diluted with ether. The ether solution was washed with 10% aqueous hydrochloric acid, saturated aqueous sodium bicarbonate and brine, then dried (MgSO$_4$), filtered, and ether evaporated in vacuo to afford 461 mg of the desired product as a clear oil; R$_f$(ether) 0.36.

EXAMPLE LXV

Preparation of
1-Iodo-9β,11α,15R-Tris-tetrahydropyran-2-yloxy-16-methyl-18,19,20-trisnorprost-13E-ene.

A solution of 461 mg of the material prepared in Example LXIV in 4.8 ml of THF was stirred under argon at 0° and 0.3 ml of triethylamine added, followed by addition of 0.11 ml of distilled mesylchloride. The reaction mixture was stirred for 1.25 hours at 0° and diluted with ether whereupon the solution was shaken with 10% HCl, saturated aqueous NaHCO$_3$, and brine, then dried (MgSO$_4$), filtered, and ether evaporated in vacuo to yield 502 mg of the crude mesylate as a yellow oil.

The oil was dissolved in 7.2 ml of dry acetone and stirred with 130 mg of anhydrous potassium carbonate and 610 mg of anhydrous lithium iodide for 15 hours at 25°. The acetone was evaporated in vacuo and water was added to the residue. The water was extracted with 5% ether in hexane. The extracts were washed with 10% aqueous sodium thiosulfate and brine, then dried (MgSO$_4$), filtered, and solvents evaporated in vacuo to yield the crude product as a yellow oil (439 mg). Thin layer chromatography indicated some loss of protecting group, so the oil was dissolved in 10 ml of ether and stirred with 0.25 ml of dihydropyran (DHP) and a trace of p-toluenesulfonic acid for 1 hour at 25°. The reaction mixture was diluted with ether whereupon the solution was washed with saturated aqueous NaHCO$_3$ and brine, then dried (MgSO$_4$), filtered and ether removed in vacuo to yield 458 mg of the desired product as a yellow oil; R$_f$(ether) 0.65.

EXAMPLE LXVI

Preparation of
1-Dimethylamino-16-methyl-19,18,20-trisnorprost-13E-en-9β,11α,15R-triol.

A solution of 458 mg of the material prepared in Example LXV was dissolved in 1.2 ml of dry dimethylformamide (DMF) and added to a 50°, stirred solution of 110 mg K$_2$CO$_3$ and 250 mg of diethylamino in 1.7 ml of dry DMF under argon. The reaction mixture was stirred for 30 minutes at 50° then poured into water and the mixture extracted with 1:1 etherhexane. The organic layer was washed with brine, then dried (K$_2$CO$_3$), filtered and solvents evaporated in vacuo to yield 380 mg of an orange oil. The oil was stirred with 19 ml of 65:35:10 acetic acid-water-THF for 18 hours at 35° under argon. Solvents were evaporated in vacuo and 1 N sodium hydroxide added to the residue. The mixture was extracted with ether whereupon the extracts were washed with 10% aqueous NaHCO$_3$ and brine then dried (K₂CO₃), filtered and ether evaporated in vacuo to yield 100 mg of a light yellow oil having the structure:

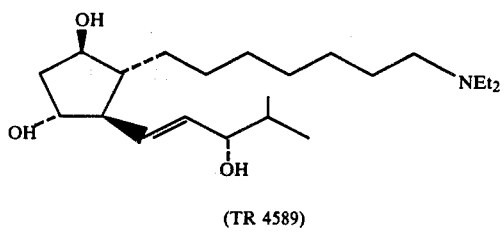

(TR 4589)

The structure of this material was confirmed by nuclear magnetic resonance, infrared and mass spectral analysis.

Analysis - NMR(CDCl₃): δ0.92(overlapping pair of d, 6, Pr-H), 1.03(t, J=7.0Hz, 6, CH₂CH₃)), 2.40(bt, 2, CH₂N), 2.6(q, 4, CH₃CH₂N), 3.1–4.3(broad, 6, CHOH), 5.56(m, 2, CH=CH)

IR(CHCl₃) 2.78, 2.95(broad, 10.4μ Mass Spectrum: m/e 369(p+).

EXAMPLE LXVII

Preparation of dl-1-Triethylamino-16,20-methanoprost-13E-en-9-one bromide.

To 99 mg (0.26 mmol) dl-2-decarboxy-2-bromomethyl-11,15-dideoxy-16,20-methano PGE₁, under argon, at room temperature, was added 0.20 ml triethylamine and the reaction mixture stirred for 80 hours in the dark. The reaction (ca. 20% complete) was then stirred at 80° for 192 hours in the dark. The brown-black residue was taken up in chloroform and purified by preparative TLC (silica gel F-254; 10:10:0.1 (V/V) chloroform-methanol-48% hydrobromic acid as eluent) to yield 37.6 mg (30%) of a brown oily solid having the following structure:

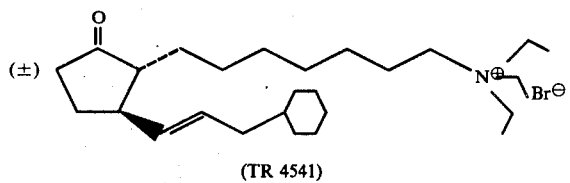

(TR 4541)

The structure of this material was confirmed by nuclear magnetic resonance, infrared and mass spectral analysis.

Analysis - NMR(CDCl₃): δ0.95(9H, t), 1.1–2.7(31H, m), 3.5(8H, bq), 5.5(2H, m)

IR(CHCl₃): 3000, 2920, 2845, 1730, 1480, 1445, 1200, 965 cm⁻¹

Mass Spectrum (5.0 eV): no 484.6(p+), 3.76(p+-Br⁷⁹—C₂H₆), 375(p+-Br⁸¹-C₂H₆N), 374(p+-Br⁸¹-C₂H₆), 362(p+-Br⁷⁹-C₂H₆N), 361(p+-Br⁸¹-C₂H₅N), 360(p+-Br⁸¹-C₂H₅), 358, 348, 347, 346, 344, 334, 333, 332, 330, 321, 320, 319, 318, 317, 280, 278, 277, 206, 205, 163, 137, 135 and other areas below 123; R_f(10:10:0.1 V/V chloroform-methanol-48% hydrobromic acid) 0.69.

EXAMPLE LXVIII

Preparation of 1-(N-Oxido-N-morpholino)-15R-hydroxy-16,20-methanoprost-13E-en-9-one.

TR 4346 was prepared from the reaction of 2-(7-morpholinoheptyl)-2-cyclopentenone (Example XXXXVI) and 1-iodo-3R-(1-ethoxyethoxy)-3-cyclohexyl-1-transpropene (Example XX) using the processes described in Examples XX and LXI.

To a solution containing 365 mg (0.754 mmol) of 1-(N-Morpholino)-15R-hydroxy-16,20-methanoprost-13E-en-9-one having the following structure:

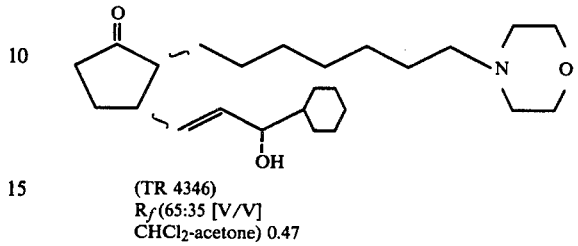

(TR 4346)
R_f(65:35 [V/V] CHCl₂-acetone) 0.47 and whose structure was confirmed as follows:

Analysis - NMR(CDCl₃): δ1.1–2.3(26H, m), 2.5(8H, bt), 3.0(1H, D₂O exchangeable), 3.8(4H, t), 4.2(1H, m), 5.6(2H, m) IR(CHCl₃): 3600(sharp), 3560-3300(broad), 3000, 2935, 2855, 2815, 1735, 1635, 1450, 1440, 1270, 1110, 965 cm⁻¹

Mass Spectrum (70 eV): 405(p+), 387(p+-H₂), 322(p+-C₆H₁₁), 266(p+-C₆H₁₇N), 198, 184, 170, 100(base peak, C₅H₁₁NO); in 2 ml of chloroform at −10°, under argon, was added, dropwise, a solution containing 157 mg of purified m-chloroperbenzoic acid in 4 ml of chloroform. The solution was allowed to warm to room temperature over 3 hours. The reaction mixture was poured onto a column containing 25 mg of base washed (ammonium hydroxide) silica gel and the product eluted with chloroform (1 liter) and 3:1 (V/V) chloroform-methanol (1 liter). In this manner 336 mg (88%) of a pale yellow oil having the structure:

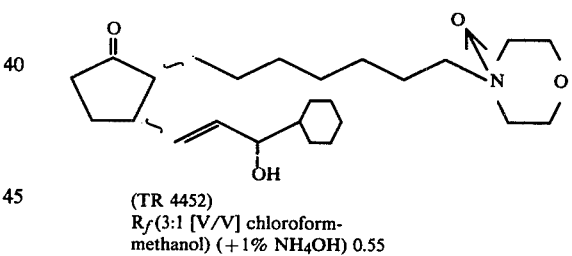

(TR 4452)
R_f(3:1 [V/V] chloroform-methanol) (+1% NH₄OH) 0.55 was obtained. The structure of this material was confirmed by nuclear magentic resonance, infrared and mass spectral analysis.

Analysis-NMR(CDCl₃): δ1.1–2.5(29H, m), 3.2(6H, m), 3.74–4.0(2H, m), 4.5(4H, m), 5.7(2H, m) IR(CHCl₃): 3600(sharp), 3550-3300(broad), 3000, 2935, 2850, 1730, 1450, 1504, 1110, 965 cm⁻¹

Mass Spectrum (70 eV): 405(p+-O¹⁶), 403(p+-H₂O), 332, 318, 300(p+-H₂O-C₄H₉NO₂), 266, 236, 235, 217, 199, 189, 179, 175 and others 161 and below.

Note: The above procedure was adopted from J. C. Craig et al., J. Org. Chem., 35, 1721 (1970).

EXAMPLE LXIX

Preparation of 1-(N-Morpholino)-15S-hydroxyprost-13E-en-9-one.

A solution of 654 mg (2.0 mmol) of 1-iodo-3S-(α-ethoxyethoxy)-trans-1-octene in 10 ml anhydrous ether was stirred in a −78° bath under argon as 4.24 ml (4.0 mmol) of a solution of t-butyllithium in n-pentane (1.06

M) was added via syringe. The resultant mixture was stirred for 2 hours at −78°.

A second solution was prepared by stirring a slurry of 262 mg (2.0 mmol) of copper(I)pentyne in 10 ml of anhydrous ether with 0.45 ml of hexamethylphosphorous triamide under argon until it had become homogeneous. This copper solution was then transferred via syringe to the above alkenyl lithium solution at −78°.

The resultant yellow solution was then stirred at −78° for 10 minutes before a third solution of 504 mg (1.9 mmol) of 2-(7-morpholinoheptyl)-2-cyclopenten-1-one in 5 ml anhydrous toluene was injected via syringe. The resultant orange slurry was stirred at −78° for 15 minutes and gradually warmed to −20° over a 2 hour period. The yellow slurry was quenched with 5 ml of 20% aqueous ammonium chloride solution (pH 8 with added ammonium hydroxide). Hexane (20 ml) was added and the layers separated. The aqueous layer was back-extracted (2×) with 20 ml n-hexane. The combined organic layers were filtered through a pad of Celite and the filtrate evaporated in vacuo. The oily residue was dissolved in 2 ml of tetrahydrofuran, 20 ml of 65:35 (V/V) acetic acid-water was added and the solution stirred overnight at room temperature, under argon. Solvents were evaporated in vacuo and the residue diluted with 5% aqueous sodium bicarbonate and ether. The layers were separated and the aqueous layer (ca. pH 8) was back-extracted (2×) with ether-ethyl acetate (1:1 V/V). The combined organic layers were washed with saturated aqueous brine, dried (MgSO4) and evaporated in vacuo to yield 739 mg of crude products as an orange oil. This product was column chromatographed on silica gel 60 utilizing chloroform to 1:1 (V/V) chloroform-ethyl acetate as eluent. By this process a partial separation of the two diastereomers was obtained. The two compounds were combined to yield 472.9 mg (63%) of a pale yellow oil having the structure:

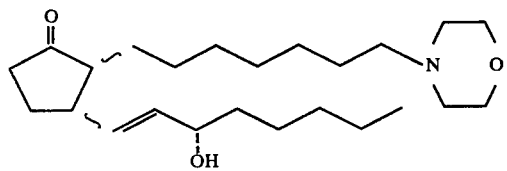

(TR 4396)
$R_f$(1:1 [V/V] CHCl$_3$-acetone)
0.42

The structure of this material was confirmed by nuclear magentic resonance, infrared and mass spectral analysis.

Analysis-NMR(CDCl$_3$): δ0.9(3H, bt), 1.2–2.1(25H, m), 2.5(7H, m), 3.8(4H, t), 4.2(1H, m), 5.7(2H) IR(CHCl$_3$): 3575(sharp), 3550–3300(broad), 3000, 2925, 2850, 2800, 1630, 1590, 1455, 1270, 1110, 1060, 965 cm$^{-1}$ Mass Spectrum: 393(p+), 376(p+-OH or NH$_3$), 375(p+-H$_2$O), 336, 329(p+-C$_4$H$_2$N), 322(p+-C$_5$H$_{11}$), 310, 304(p+-C$_4$H$_{11}$NO), 294(p+-C$_5$H$_9$NO), 292(p+-C$_6$H$_{15}$N or C$_5$H$_{11}$NO).

EXAMPLE LXX

Preparation of 1-(N-Morpholino)-15R-hydroxy-16-methyl-18,19,20-trisnorprost-13E-en-9-one.

In a manner similar to that described in example LXIX a composition having the following structure was prepared:

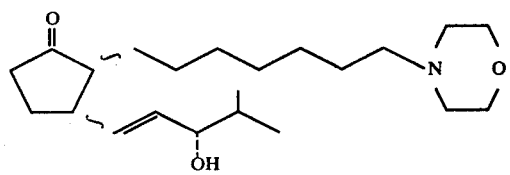

TR 4398
$R_f$(1:1 [V/V] CHCl$_3$-acetone)
0.39

The structure of this material was confirmed by nuclear magnetic resonance, infrared and mass spectral analysis.

Analysis-NMR(CDCl$_3$): δ0.95(6H, d), 1.1–2.3(17H, m), 2.5(6H, bt), 3.8(4H, t), 4.25(1H, m), 5.7(2H, m) IR(CHCl$_3$): 3600, 3560–3300(broad), 3000, 2940, 2850, 2815, 1730, 1455, 1365, 1110, 965 cm$^{-1}$ Mass Spectrum (70 eV): 365(p+), 350(p+-CH$_3$), 348(p+-OH), 347(p+-H$_2$), 323, 322(base peak, p+-C$_3$H$_7$), 308, 294, 282, 267, 266.

The following examples illustrate the utilities of the prostaglandins of the present invention.

EXAMPLE LXXI

Inhibition of Platelet Aggregation By Prostaglandins In Vitro.

The ability of test compounds to inhibit platelet aggregation is determined by a modification of the turbidometric technique of Born (1962). Blood is collected from human volunteers, who have not ingested aspirin or aspirin-containing products within the last two weeks, in heparinized Vacutainers (Becton, Dickinson and Co.) and is allowed to settle for one (1) hour. The platelet rich plasma (PRP) supernates are collected and pooled. Siliconized glassware is used throughout.

In a representative assay, 1.9 ml of PRP and 0.2 ml of test compound at the appropriate concentrations (0.001 to 100 mcgm), or 0.2 ml of distilled water (control procedure) are placed in sample cuvettes. The cuvettes are placed in a 37° incubation block for 15 minutes, and then a Coleman Jr. Spectrophotometer (Model 6C) linked to a strip chart recorder. After 30–60 seconds, 0.2 ml of a solution, prepared by diluting a calf-skin collagen solution (Worthington Biochemical) 1:9 with Tyrodes Solution, is added to each cuvette. Platelet aggregation is evidenced by a decrease in optical density.

Calculation of the degree of inhibition of platelet aggregation, exhibited by each concentration of test compound, is accomplished according to the method of Caprino et al. (1973). An IC$_{50}$ value* is then determined graphically and a value judgement is assigned as follows:

*IC$_{50}$ is the concentration of compound which produces 50% inhibition of the response measured in the absence of the compound.

| Response | Value Judgement |
|---|---|
| $IC_{50} < 0.001$ mcgm | +5 |
| $IC_{50} > 0.001$ mcgm and $<0.01$ mcgm | +4 |
| $IC_{50} > 0.01$ mcgm and $<0.1$ mcgm | +3 |
| $IC_{50} > 0.1$ mcgm and $<1.0$ mcgm | +2 |
| $IC_{50} > 1.0$ mcgm | +1 |
| Compound exhibits no inhibitory (+) or stimulatory (−) activity | 0 |
| Produces <25% increase in aggregation at highest dosage tested | −0 |
| Produces >25% and <50% increase in aggregation at highest dosage tested | −1 |
| Produces >50% and <75% increase in aggregation at highest dosage tested | −2 |
| Produces >75% and <100% increase in aggregation at highest dosage tested | −3 |
| Produces >100% increase in aggregation at highest dosage tested | −4 |

References:
Born, G. V. R., Nature 194, 927 (1962).
Caprino, L., Borrelli, F. and Falchetti, R., Arzneim-Forsch. 23, 1277 (1973).

The foregoing screening technique was used to test the novel prostaglandins of the instant invention for inhibition of platelet aggregation with the following results:

Table I

| Prostaglandin | Example No. | Value Judgement for Inhibition of Platelet Aggregation |
|---|---|---|
| Bromo Analogues | | |
| TR 4353 | XVII | — |
| TR 4343 | XVIII | +1 |
| TR 4341 | XVIII | +1 |
| TR 4351 | XIX | — |
| TR 4352 | XIX | — |
| TR 4360 | XX | +1 |
| TR 4361 | XX | +1 |
| TR 4389 | XXI | +1 |
| TR 4384 | XXI | +1 |
| TR 4473 | XXII | +1 |
| TR 4369 | XXII | +1 |
| TR 4409 | XXIII | −0 |
| Dimethylphosphono Analogues | | |
| TR 4177 | V | +1 |
| TR 4178 | V | +1 |
| TR 4192 | IX | +1 |
| TR 4235 | XIII | +1 |
| TR 4234 | XIV | +1 |
| TR 4191 | IX | +1 |
| Thio Analogues | | |
| TR 4388 | XXVII | +1 |
| TR 4415 | XXX | +1 |
| TR 4447 | XXXII | +1 |
| TR 4448 | XXXIII | +1 |
| TR 4444 | XXXIV | −0 |
| TR 4496 | XXXV | +1 |
| TR 4487 | XXXV | +1 |
| TR 4486 | XXXVI | +1 |
| TR 4414 | XXXXIII | +1 |
| TR 4615 | XXXXIV | +1 |
| Amino Analogues | | |
| TR 4396 | LXIX | — |
| TR 4346 | LXVIII | — |
| TR 4398 | LXX | — |
| TR 4452 | LXVIII | +1 |
| TR 4589 | LXVI | — |
| TR 4798 | LXI | — |
| TR 4761 | LXII | +1 |
| TR 4760 | LXII | — |
| TR 4762 | LXIII | — |

EXAMPLE LXXI

Evaluation of the Effects of Prostaglandin Analogues on the Guinea Pig Trachea In Vitro.

A male guinea pig weighing 200–500 gm is killed by a blow on the head. A 20 mm length of the trachea is dissected from the animal, transferred to a petri dish containing Kreb's solution aerated with 95% $O_2$ and 5% $CO_2$ at 37° and cut longitudinally opposite the tracheal muscle. The tissue is then cut transversely three quarters of the distance across the tissue and this procedure is continued for the whole tissue. The ends of the trachea can be pulled to form a zig-zag shaped strip. The tracheal strip used in the experiment is approximately 30 mm when extended under 0.25–0.5 gm load in the tissue bath. Cotton thread is tied to one end of the tissue, and linen thread to the other. It is attached via the linen thread to a glass hook in a 5 ml isolated tissue bath containing Kreb's solution at 37° and aerated with a mixture of 95% $O_2$ and 5% $CO_2$. The opposite end is attached via cotton to an isotonic Harvard transducer (Model 386 Heart/Smooth Muscle Transducer, Harvard Apparatus). The load on the transducer level is small, usually 0.3 gm, with a range of 0.25–0.5 gm, and the magnification high, 80 fold using an appropriate twin-channel pen recorder. A minimum of thirty minutes is allowed before applying a drug to the tissue. Drugs are then applied (in volumes of 0.5 ml) at thirty minute intervals, being in contact with the tissue for five minutes followed by an overflow washout time of twenty seconds.

Prostaglandin $E_1$, at a bath concentration of 0.1 mcg/ml, is then tested repeatedly on two such strips, obtained from two different animals, until two responses (the values of which are recorded) differing by no more than 25% occur. This concentration of $PGE_1$ should elicit a relaxation expressed as from 10 to 30 mm of recorder pen excursion. A test compound is then added to the same two strips at bath concentrations of 0.01, 0.1, 1.0 and 10.0 mcg/ml and the effects of the compound are recorded. After the test compound has been evaluated at the highest concentration, $PGE_1$ is retested at 0.1 mcg/ml (and the value of the response recorded) to insure that the viability of the strips was retained during the experiment. The mean of the effects of the test compound on the two strips is then calculated for each concentration, and, based on the resulting values, a value judgement is assigned as follows:

| Response | Value Judgement |
|---|---|
| More relaxation at 0.01 mcg/ml than that elicited by $PGE_1$ | R4 |
| More relaxation at 0.1 mcg/ml than that elicited by $PGE_1$ | R3 |
| More relaxation at 1.0 mcg/ml than that elicited by $PGE_1$ | R2 |
| More relaxation at 10.0 mcg/ml than that elicited by $PGE_1$ | R1 |
| More than 0 but less relaxation at any concentration than that elicited by $PGE_1$ | R0 |
| No effect at any concentration | 0 |
| More than 0 but less contraction at any concentration than the degree of relaxation elicited by $PGE_1$ | C0 |
| More contraction at 10.0 mcg/ml than the degree of relaxation elicited by $PGE_1$ | C1 |
| More contraction at 1.0 mcg/ml than the degree of relaxation elicited by | |

| Response | Value Judgement |
|---|---|
| PGE₁ | C2 |
| More contraction at 0.1 mcg/ml than the degree of relaxation elicited by PGE₁ | C3 |
| More contraction at 0.01 mcg/ml than the degree of relaxation elicited by PGE₁ | C4 |

1. If less than 10 mm relaxation is observed, retest PGE₁ at 1.0 mcg/ml; if less than 10 mm relaxation is seen at this concentration prepare new tracheal strips. If more than 30 mm relaxation is observed at 0.1 mcg/ml PGE₁, retest PGE₁ at a concentration of 0.01 mcg/ml; if more than 30 mm relaxation is observed at this concentration also, retest PGE₁ at 0.001 mcg/ml. If it is necessary to use a concentration of PGE₁ other than 0.1 mcg/ml in order to obtain the desired response (i.e., 10 to 30 mm relaxation), adjust the listed concentrations of the test compound up one or down one or two orders of magnitude as appropriate.

The foregoing screening technique was used to test the novel prostaglandins of the instant invention for their effect on the guinea pig trachea with the following results:

Table II

| Prostaglandin | Example No. | Value Judgement for Effect on Guinea Pig Trachea |
|---|---|---|
| Bromo Analogues | | |
| TR 4341 | XVII | R0 |
| TR 4343 | XVIII | — |
| TR 4351 | XIX | C0 |
| TR 4352 | XIX | C0 |
| TR 4353 | XVII | R0 |
| TR 4360 | XX | C0 |
| TR 4361 | XX | R0 |
| TR 4369 | XXI | C0 |
| TR 4384 | XXI | 0 |
| TR 4389 | XXII | C0 |
| TR 4409 | XXII | R0 |
| TR 4473 | XXIII | — |
| Dimethylphosphono Analogues | | |
| TR 4177 | V | — |
| TR 4178 | V | C0 |
| TR 4191 | IX | 0 |
| TR 4192 | IX | 0 |
| TR 4234 | XIV | 0 |
| TR 4235 | XIII | 0 |
| Thio Analogues | | |
| TR 4388 | XXVII | C0 |
| TR 4414 | XXXXIII | R0 |
| TR 4415 | XXX | R0 |
| TR 4444 | XXXIV | 0 |
| TR 4447 | XXXII | 0 |
| TR 4448 | XXXIII | R0 |
| TR 4486 | XXVI | C0 |
| TR 4487 | XXXV | C0 |
| TR 4615 | XXXIV | C0 |
| TR 4496 | XXXV | C0 |
| Amino Analogues | | |
| TR 4396 | LXIX | C0 |
| TR 4346 | LXVIII | C0 |
| TR 4398 | LXX | C0 |
| TR 4452 | LXVIII | C0 |
| TR 4541 | LXVII | C0 |
| TR 4589 | LXVI | R0 |
| TR 4798 | LXI | — |
| TR 4761 | LXII | C0 |
| TR 4760 | LXII | — |
| TR 4762 | LXIII | C0 |

EXAMPLE LXXIII

Evaluation of the Effects of Prostaglandin Analogues on Gastric Secretion of the Rat.

A procedure based on that described by Lipmann (1969) is used to assess the influence of test compound on gastric secretion. Rats of one sex weighing 150 to 200 gm are randomly divided into groups of six animals each and fasted for 48 hours previous to the experiments, water being available ad libitum. The animals are anesthetized with ether, the abdomen opened through a midline incision, and the pylorus ligated. Test compounds are diluted from stock solution so as to administer a dose of 1.5 mg/kg in a volume equivalent to 1 ml/kg. Subcutaneous injections are applied immediately after surgery and again 2 hours later, so that a total dose of 3.0 mg/kg is administered. Dilutions are made with phosphate buffer (pH 7.38) as recommended by Lee et al. (1973), in order to insure adequate stability of drugs at the subcutaneous depot. Each compound is tested in one group of rats; an additional control group receives only one vehicle.

Four hours after pyloric ligation the animals are killed with ether, the cardias ligated and the stomachs removed. The volume of gastric secretion is measured and the contents centrifuged at 5000 rpm for 10 minutes. Total acid in the supernatant is titrated against a 0.1 N sodium hydroxide solution and the amount expressed in mEq.

Volume and total acid values of the treated group are compared with those of the controls by the test. Antisecretory activity is scored according to the following scale:

| % Decrease in Acidity | Value Judgement |
|---|---|
| <26 | 0 |
| 26–50, not significant | 1 |
| 26–50, significant | 2 |
| 51–75 | 3 |
| 76–100 | 4 |

References

Lee, Y. H., Cheng, W. O., Bianchi, R. G., Mollison, K. and Hansen, J., Prostaglandins 3: 29 (1973).

Lipmann, W., J. Pharm. Pharmacol. 21: 335 (1968).

The foregoing screening technique was used to test the novel prostaglandins of the instant invention for the evaluation of their effect on the gastric secretion of the rat with the following results:

Table III

| Prostaglandin | Example No. | Value Judgement for Effect on Gastric Secretion of the Rat |
|---|---|---|
| Bromo Analogues | | |
| TR 4341 | XVII | — |
| TR 4343 | XVIII | 0 |
| TR 4351 | XIX | 0 |
| TR 4352 | XIX | 0 |
| TR 4353 | XVII | 0 |
| TR 4360 | XX | 0 |
| TR 4361 | XX | 0 |
| TR 4369 | XXI | — |
| TR 4384 | XXI | 0 |
| TR 4389 | XXII | 0 |
| TR 4409 | XXII | 0 |
| TR 4473 | XXIII | — |
| Dimethylphosphono Analogues | | |
| TR 4177 | V | — |
| TR 4178 | V | — |
| TR 4191 | IX | 0 |
| TR 4192 | IX | — |
| TR 4234 | XIV | — |
| TR 4235 | XIII | 0 |
| Thio Analogues | | |

Table III-continued

| Prostaglandin | Example No. | Value Judgement for Effect on Gastric Secretion of the Rat |
|---|---|---|
| TR 4388 | XXVII | — |
| TR 4414 | XXXXIII | 0 |
| TR 4415 | XXX | — |
| TR 4444 | XXXIV | 0 |
| TR 4447 | XXXII | — |
| TR 4448 | XXXIII | — |
| TR 4486 | XXXVI | 1 |
| TR 4487 | XXXV | 0 |
| TR 4615 | XXXXIV | 0 |
| TR 4496 | XXXV | 0 |
| Amino Analogues | | |
| TR 4396 | LXIX | 1 |
| TR 4346 | LXVIII | 0 |
| TR 4398 | LXX | — |
| TR 4452 | LXVIII | 0 |
| TR 4541 | LXVII | 1 |
| TR 4589 | LXVI | 1 |
| TR 4798 | LXI | — |
| TR 4761 | LXII | — |
| TR 4760 | LXII | — |
| TR 4762 | LXIII | 2 |

EXAMPLE LXXIV

Evaluation of the Antagonist Effects of Prostaglandin Analogues on the Guinea Pig Ileum.

The degree and specificity of antagonism of test compounds to the smooth muscle stimulant effects of PG's are assessed in segments of terminal guinea pig ileum. Preparations are placed in tissue chambers filled with Ringer-Tyrode solution at 37°, bubbled with a mixture of 95% $O_2$ and 5% $CO_2$, and arranged for isometric recording with force displacement transducers. The segments are stretched to an initial tension of 1 g, and responses to a test concentration of acetylcholine (0.1 mcg/ml) are obtained every 5 minutes until two similar responses are observed (usually after four administrations). Responses to acetylcholine (0.1 mcg/ml), $PGE_1$ (0.1 mcg/ml), $BaCl_2$ (100 mcg/ml) and $PGF_{2\alpha}$ (1.0 mcg/ml) are obtained (and recorded) in that order at 5 minute intervals before and after 100 seconds of incubation with 0.1 and 1.0 mcg/ml of the test compound. Any direct contractile effect of the test compound is recorded and evaluated in terms of mean values in grams of tension developed at each concentration. Responses to the different agonists observed after incubation with the test compound are expressed as percent of control responses. All drugs are administered in a volume of 0.1 ml.

Antagonism of PG's is scored indepedently for $PGE_1$ and $PGF_{2\alpha}$ according to the following criteria:

| | Value Judgement |
|---|---|
| Less than 50% blockade of PG response. | 0 |
| More than 50% blockade of PG responses and more than 10% antagonism of Ach and/or $BaCl_2$, or production of direct contraction. | 1 |
| More than 50% blockade of PG responses at 1 mcg/ml with less than 11% antagonism of Ach and $BaCl_2$ without production of direct contraction. | 2 |
| More than 50% blockade of PG responses at 0.1 mcg/ml with less than 11% antagonism of Ach and $BaCl_2$ without production of direct contraction. | 3 |
| More than 50% blockade of PG response at 0.1 and 1.0 mcg/ml with less than 11% blockade of Ach and $BaCl_2$ responses without production of direct contraction at either concentration. | 4 |

The foregoing screening technique was used to test the novel prostaglandins of the instant invention for the evaluation of their antagonistic effect on the guinea pig ileum with the following results:

Table IV

| Prostaglandin | Example No. | Value Judgement for Antagonistic Effect on the Guinea Pig Ileum | |
|---|---|---|---|
| | | $PGE_1$ | $PGF_{2\alpha}$ |
| Bromo Analogues | | | |
| TR 4341 | XVII | 0 | 0 |
| TR 4343 | XVIII | — | — |
| TR 4351 | XIX | 0 | 0 |
| TR 4352 | XIX | 0 | 0 |
| TR 4353 | XVII | 0 | 0 |
| TR 4360 | XX | 0 | 0 |
| TR 4361 | XX | 0 | 0 |
| TR 4369 | XXI | 0 | 0 |
| TR 4384 | XXI | 0 | 2 |
| TR 4389 | XXII | 0 | 0 |
| TR 4409 | XXII | 0 | 0 |
| TR 4473 | XXIII | — | — |
| Dimethylphosphono Analogues | | | |
| TR 4177 | V | 0 | 0 |
| TR 4178 | V | 0 | 0 |
| TR 4191 | IX | 0 | 0 |
| TR 4192 | IX | 0 | 0 |
| TR 4234 | XIV | 0 | 0 |
| TR 4235 | XIII | 0 | 0 |
| Thio Analogues | | | |
| TR 4388 | XXVII | 0 | 0 |
| TR 4414 | XXXXIII | 0 | 0 |
| TR 4415 | XXX | 0 | 0 |
| TR 4444 | XXXIV | 0 | 0 |
| TR 4447 | XXXII | 0 | 0 |
| TR 4448 | XXXIII | 0 | 0 |
| TR 4486 | XXXII | 1 | 0 |
| TR 4487 | XXXV | 0 | 0 |
| TR 4615 | XXXXIV | 0 | 0 |
| TR 4496 | XXXV | 0 | 0 |
| Amino Analogues | | | |
| TR 4396 | LXIX | 0 | 0 |
| TR 4346 | LXVIII | 0 | 0 |
| TR 4398 | LXX | 1 | 1 |
| TR 4452 | LXVIII | 0 | 0 |
| TR 4541 | LXVII | 0 | 0 |
| TR 4589 | LXVI | 0 | 0 |
| TR 4798 | LXI | 1 | 0 |
| TR 4761 | LXII | 0 | 0 |
| TR 4760 | LXII | — | — |
| TR 4762 | LXIII | 0 | 0 |

EXAMPLE LXXV

Evaluation of the Effects of Prostaglandin Analogues on Blood Pressure in the Hypertensive Rat.

The acute antihypertensive activity of test compounds is determined in rats made hypertensive by the procedure of Grollman (1944). Female rats weighing between 60 and 100 g are anesthetized with ether, the right kidney approached through a flank retroperitoneal incision, decapsulated and tied with a figure-of-eight ligature. The animals are left to recover and two weeks later are again anesthetized and the contralateral kidney removed. Four weeks after the second operation the rats are subjected to indirect blood pressure measurements and those showing systolic pressure values greater than 160 mmHg are selected for drug testing.

Blood pressure is measured in the tail with an inflatable occluding cuff placed at the base of the extremity and a pulse detector located distally. The cuff is inflated to approximately 300 mmHg and is slowly deflated until pulsations appear, indicating the level of systolic pressure; diastolic pressure is not recorded by this procedure. All measurements are carried out in unanesthetized, unsedated animals maintained in a warm environment during the recording procedure and for at least 6 hours before. In all cases, three pressure readings are obtained in succession and mean values are calculated thereof.

Experiments are carried out in groups of five hypertensive rats in which systolic pressure is determined immediately before and 2, 4, 6 and 8 hours after the intraperitoneal administration of the test compound at a dose of 1 mc/kg. Drugs are diluted from stock solutions with phosphate buffer (Lee et al., 1973), so as to inject this quantity in a volume of 1 ml/kg. Changes from control blood pressure values are calculated for each interval both in mmHg and in percent and evaluated for significance by means of Wilcoxon's signed rank test (Wilcoxon and Wilcox, 1964). Activity of the compound is scored as follows:

| Blood Pressure Decrease | Value Judgement |
|---|---|
| Not significant at any time interval | 0 |
| Significant at one time interval | 1 |
| Significant at two time intervals | 2 |
| Significant at three time intervals | 3 |
| Significant at all four time intervals | 4 |

References

Grollman, A., Proc. Soc. Exper. Biol. Med., 57: 102 (1944).

Lee, Y. H., Cheng, W. O., Bianchi, R. G., Mollison, K. and Hansen, J., Prostanglandins 3: 29 (1973).

Wilcoxon, F. and Wilcox, R. A., Some Rapid Approximate Statistical Procedures, Lederle Laboratories, Pearl River (1964).

The foregoing screening technique was used to test the novel prostaglandins of the instant invention for the evaluation of their effects on the blood pressure in the hypertensive rat with the following results:

Table V

| Prostaglandin | Example No. | Value Judgement for Effect on Blood Pressure in the Hypertensive Rate |
|---|---|---|
| Bromo Analogues | | |
| TR 4341 | XVII | 0 |
| TR 4343 | XVIII | — |
| TR 4351 | XIX | 0 |
| Tr 4352 | XIX | 0 |
| TR 4353 | XVII | 0 |
| TR 4360 | XX | 0 |
| TR 4361 | XX | 0 |
| TR 4369 | XXI | 0 |
| TR 4384 | XXI | 0 |
| TR 4389 | XXII | 0 |
| TR 4409 | XXII | 0 |

Table V-continued

| Prostaglandin | Example No. | Value Judgement for Effect on Blood Pressure in the Hypertensive Rate |
|---|---|---|
| TR 4473 Dimethylphosphono Analogue | XXIII | — |
| TR 4177 | V | — |
| TR 4178 | V | — |
| TR 4191 | IX | 0 |
| TR 4192 | IX | 0 |
| TR 4234 | XIV | 0 |
| TR 4235 | XIII | 0 |
| Thio Analogues | | |
| TR 4388 | XXVII | 0 |
| TR 4414 | XXXXIII | 0 |
| TR 4415 | XXX | — |
| TR 4444 | XXXIV | — |
| TR 4447 | XXXII | — |
| TR 4448 | XXXIII | — |
| TR 4486 | XXXVI | — |
| TR 4487 | XXXV | 0 |
| TR 4615 | XXXXIV | — |
| TR 4496 | XXXV | 0 |
| Amino Analogues | | |
| TR 4396 | LXIX | 0 |
| TR 4346 | LXVIII | 0 |
| TR 4398 | LXX | 0 |
| TR 4452 | LXVIII | — |
| TR 4541 | LXVII | — |
| TR 4589 | LXVI | 1 |
| TR 4798 | LXI | — |
| TR 4761 | LXII | — |
| TR 4760 | LXII | — |
| TR 4762 | LXIII | — |

Referring to the foregoing tables (I-V), it can be determined that compounds active in the platelet aggregation assay as inhibitors (Table I) would be expected to be useful as potential antithrombotic agents. However, based on the value judgements, the examples listed in Table I might not be particularly potent in this respect.

Compounds active in the quinea-pig trachea assay as relaxants (Table II) are useful as potential bronchodilators and hence would be of value as anti-asthmatic agents. Prostaglandins have the advantage over the $\beta$-adrenoceptor stimulants, such as isoproterenol and salbutanol, in that they would not be expected to have any cardiac side effects. However, like $\beta$-adrenoceptor stimulants, such prostaglandins would have therapeutic (i.e. post asthmatic attack) effectiveness and hence have an advantage over the chromone anti-allergic drugs (e.g. Intal) which are only effective when taken prophylactically.

Compounds which inhibit gastric acid secretion, e.g. TR 4762 (Table III) would be expected to have utility in the treatment of gastric hyperacidity and so aid the healing of peptic ulcers. These compounds may have advantages over the synthetic anti-secretory agents (i.e. $H_2$-receptor antagonists) by being less toxic.

Although prostaglandin antagonists have been little, if at all, used clinically, they have many potential therapeutic uses. For instances, TR 4384, which antagonizes $PGF_{2\alpha}$, would be expected to inhibit anaphylactic bronchoconstriction in which $PGF_{2\alpha}$ is thought to play an aetiologic role. Furthermore, since TR 4384 does not inhibit $PGE_1$, it might be expected that the bronchodilator action of $PGE_1$ would be enhanced by blockade of the opposing action of $PGF_{2\alpha}$. Antagonists of $PGE_1$, e.g. TR 4486 and TR4798 might be expected to be useful in the treatment of inflammation or as contraceptives, indications in which E-type prostaglandins are thought to play a positive role.

Compounds having activity in the hypertensive rat screen would have potential utility as antihypertensive agents, their action resulting from their vasodilator activity.

What is claimed is:

1. Trans, 1&2-di(loweralkyl)phosphono analogues of $E_1$, $A_1$, $F_{1\alpha}$, $F_{1\beta}$, 11-deoxy-$E_1$, 11-deoxy-$F_{1\alpha}$, and 11-deoxy $F_{1\beta}$ prostaglandins represented by the structural formula:

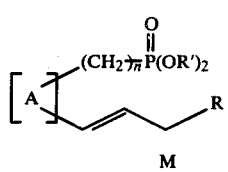

wherein n is 6 or 7, M is H or OH; A is

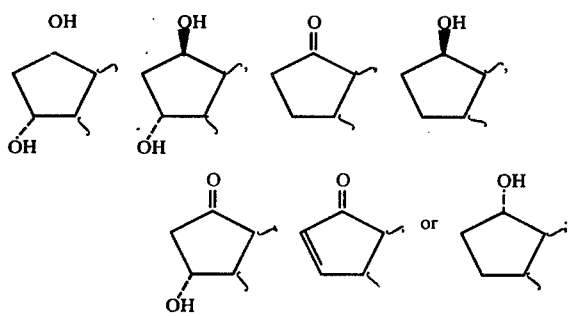

R' is methyl, ethyl, propyl or butyl; and R is $(CH_2)_3CH_3$, $(CH_2)_4CH_3$, $CH_3$, cyclohexyl,

$(CH_2)_2CH_3$ or $(CH_2)CH_3$.

2. The prostaglandins of claim 1 wherein Y is

3. The prostaglandins of claim 2 wherein n is 6, A is

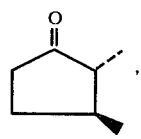

M is OH and R is $(CH_2)_4CH_3$.

4. The prostaglandins of claim 2 wherein n is 6, A is

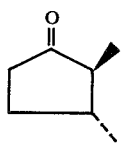

M is OH and R is $(CH_2)_4CH_3$.

5. The prostaglandins of claim 2 wherein n is 7, A is

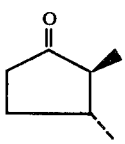

M is OH and R is $(CH_2)_4CH_3$.

6. The prostaglandins of claim 2 wherein n is 7, A is

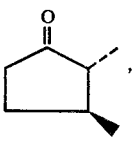

M is OH and R is $(CH_2)_4CH_3$.

7. The prostaglandins of claim 2 wherein n is 7, A is

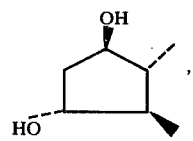

M is OH and R is $(CH_2)_4CH_3$.

8. The prostanglandins of claim 2 wherein n is 7, A is

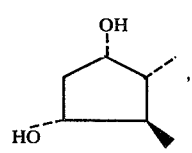

M is OH and R is $(CH_2)_4CH_3$.

* * * * *

UNITED STATES PATENT AND TRADEMARK OFFICE
CERTIFICATE OF CORRECTION

PATENT NO. : 4,171,331
DATED : October 16, 1979
INVENTOR(S) : Harold Clinton Kluender et al.

It is certified that error appears in the above-identified patent and that said Letters Patent are hereby corrected as shown below:

Column 1, Line 42, Change " 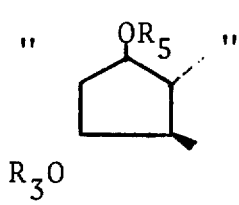 " to -- 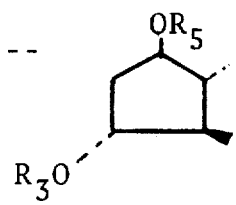 -- .

Column 1, Line 68, Change "natisomer " to -- nat-isomer -- .

Column 2, Line 2, Change " entisomer " to -- ent-isomer -- .

Column 7, Lines 18-22, Change " 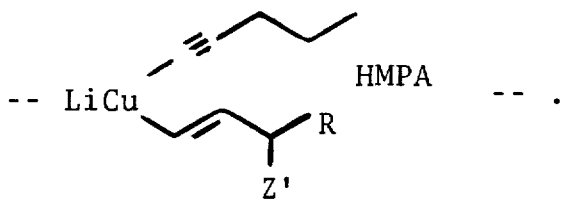 " to -- 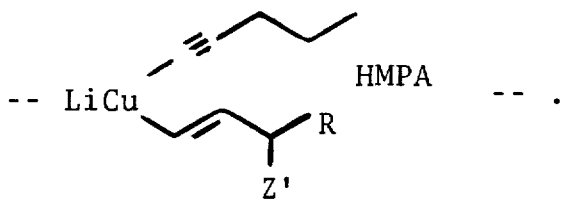 -- .

Column 7, Line 48, Change " a " to -- A -- .

Column 11, Line 15, Change " abmient " to -- ambient -- .

Column 17, Lines 5-9, Delete the formula and insert :

-- LiCu ⋯ HMPA -- .

UNITED STATES PATENT AND TRADEMARK OFFICE
CERTIFICATE OF CORRECTION

PATENT NO. : 4,171,331
DATED : October 16, 1979
INVENTOR(S) : Harold Clinton Kluender et al.

It is certified that error appears in the above-identified patent and that said Letters Patent are hereby corrected as shown below:

Column 29, Line 31, Change " $CH_2Br$ " to -- $\underline{CH}_2Br$ -- .

Column 29, Line 31, Change " $(C\underline{H}Cl_3)$ " to -- $(CHCl_3)$ -- .

Column 32, Line 13, Change " $(CH_3)$ " to -- $(C\underline{H}_3)$ -- .

Column 34, Line 1, Change "(X)" to -- (XI) -- .

Column 34, Line 51, Change " hour " to -- hours -- .

Column 36, Line 22, Change " hexaneether " to -- hexane-ether -- .

Column 41, Line 15, Change " acetateether " to --acetate-ether-- .

Column 44, Line 28, Change " 1α " to -- 11α -- .

Column 44, Lines 43-48, Delete the formula and insert

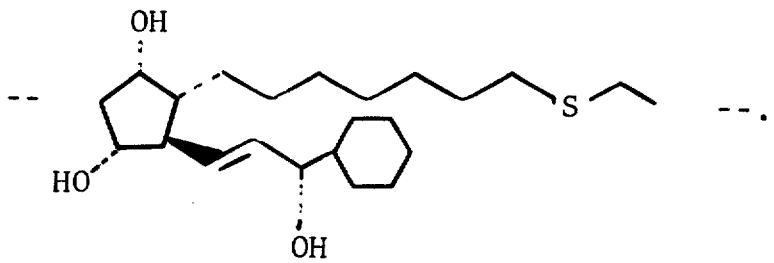

UNITED STATES PATENT AND TRADEMARK OFFICE
CERTIFICATE OF CORRECTION

PATENT NO. : 4,171,331

DATED : October 16, 1979

INVENTOR(S) : Harold Clinton Kluender et al.

It is certified that error appears in the above-identified patent and that said Letters Patent are hereby corrected as shown below:

Column 48, Line 28, Change " etherethyl " to -- ether-ethyl --.

Column 51, Line 53, Change " $CO_2CH_3$) " to $CO_2\underline{C}H_3$) --.

Column 55, Line 52, Change " O$\underline{H}$, $CH_2SH$ " to -- O$\underline{H}$, $\underline{C}H_2S\underline{H}$ --.

Column 55, Line 53, Change " CHOH " to -- C$\underline{H}$OH -- and " CH " to -- C$\underline{H}$ --.

Column 64, Line 60, Change " etherhexane " to -- ether-hexane --.

Column 77, Lines 18-24, Delete the formula and insert:

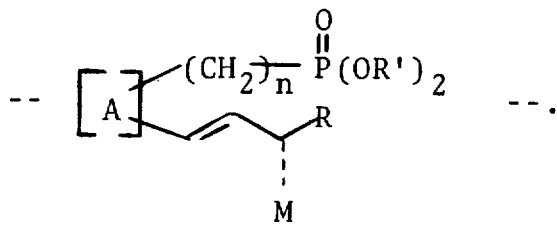

UNITED STATES PATENT AND TRADEMARK OFFICE
CERTIFICATE OF CORRECTION

PATENT NO. : 4,171,331

DATED : October 16, 1979

INVENTOR(S) : Harold Clinton Kluender

It is certified that error appears in the above-identified patent and that said Letters Patent are hereby corrected as shown below:

Column 77, Lines 29-34, Delete the first formula and insert:

-- 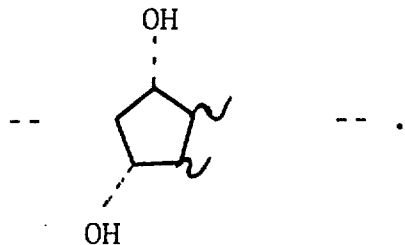 -- .

Signed and Sealed this

Twenty-ninth Day of January 1980

[SEAL]

Attest:

Attesting Officer

SIDNEY A. DIAMOND

Commissioner of Patents and Trademarks